US007880049B2

(12) United States Patent
Dumesic et al.

(10) Patent No.: US 7,880,049 B2
(45) Date of Patent: Feb. 1, 2011

(54) PRODUCTION OF LIQUID ALKANES IN THE JET FUEL RANGE (C8-C15) FROM BIOMASS-DERIVED CARBOHYDRATES

(75) Inventors: James A. Dumesic, Verona, WI (US); Yuriy Roman-Leshkov, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 869 days.

(21) Appl. No.: 11/758,963

(22) Filed: Jun. 6, 2007

(65) Prior Publication Data

US 2009/0124839 A1    May 14, 2009

Related U.S. Application Data

(63) Continuation-in-part of application No. 11/757,461, filed on Jun. 4, 2007, now Pat. No. 7,572,925.

(60) Provisional application No. 60/811,343, filed on Jun. 6, 2006.

(51) Int. Cl.
C07C 1/22    (2006.01)
C07C 1/207    (2006.01)
(52) U.S. Cl. .................................................... 585/733
(58) Field of Classification Search .................. 585/733
See application file for complete search history.

(56) References Cited

U.S. PATENT DOCUMENTS

| 2,750,394 | A | 6/1956 | Peniston |
| 2,917,520 | A | 12/1959 | Cope |
| 2,929,823 | A | 3/1960 | Garber et al. |
| 2,994,645 | A | 8/1961 | Jones et al. |
| 3,118,912 | A | 1/1964 | Smith |
| 3,201,331 | A | 8/1965 | Hunter |
| 4,339,387 | A | 7/1982 | Fléche et al. |
| 4,549,031 | A | 10/1985 | Chen et al. |
| 4,740,605 | A | 4/1988 | Rapp |
| 4,971,657 | A | 11/1990 | Avignon et al. |
| 6,603,026 | B2 | 8/2003 | Lightner |
| 2003/0032819 | A1 | 2/2003 | Lightner |

FOREIGN PATENT DOCUMENTS

| EP | 0 082 689 | 6/1983 |
| FR | 2663933 | 1/1992 |
| FR | 2664273 | 1/1992 |
| FR | 2669635 | 5/1992 |
| GB | 591858 | 5/1944 |
| GB | 600871 | 4/1948 |
| GB | 876463 | 2/1962 |
| GB | 2 131 014 A | 6/1984 |
| WO | WO 9210486 | 6/1992 |

| WO | WO 2005018799 | 3/2005 |

OTHER PUBLICATIONS

Brown, D.W. et al., Dehydration Reactions of Fructose in Non-aqueous Media, *Journal of Chemical Technology and Biotechnology* 32, 920 (1982).
Chheda, et al., "An overview of dehydration, aldol condensation and hydrogenation processes for production of liquid alkanes from biomass-derived carbohydrates," *Catalysis Today*, 2007, vol. 123, pp. 59-70.
Cottier, L. et al., 5-Hydroxymethylfurfural syntheses and chemical transformations, *Trends Heterocycl. Chem.*, vol. 2, 233-248 (1991).
Dadgar et al., The Production of Hydroxymethyl Furfural from Sawdust, *Biotechnology and Bioengineering Symp.*, No. 13, 41-52 (1983).
Dias, A.S. et al., Dehydration of xylose into furfural over micro-mesoporous sulfonic acid catalysts, *Journal of Catalysis* 229, 414 (2005).
Harris, J.F. et al., Preparation and Properties of Hydroxymethylfurfural, *Forest Products Journal* 10, 125 (1960).
Kuster, B.M.F., 5-Hydroxymethylfurfural (HMF). A Review Focusing on its Manufacture, *Starch* 42, 314 (1990).
Lewkowski, J., Synthesis, Chemistry and Applications of 5-Hydroxymethyl-furfural And Its Derivatices, *Arkivoc* Available electronically at www.arkat-usa.org/ark/journal/2001/I01_General/403/0113.pdf 17 (2001).
Mercadier, D. et al., Synthesis of 5-Hydroxymethyl-2-furancarboxaldehyde Catalysed by Cationic Exchange Resins. Part 1. Choice of the Catalyst and the Characteristics of the Reaction Medium, *J. Chem. Tech. Biotechnol.* 31:489-496 (1981).
Moreau, C. et al., Recent catalytic advances in the chemistry of substituted furans from carbohydrates and in the ensuing polymers, *Topics in Catalysis* 27, 11 (2004).
Moye, C.J., 5-Hydroxymethylfurfural, *Rev. Pure and Appl. Chem.*, 14:161-170 (1964).

(Continued)

*Primary Examiner*—Bernard Dentz
(74) *Attorney, Agent, or Firm*—Joseph T. Leone, Esq.; DeWitt Ross & Stevens S.C.

(57) ABSTRACT

Described is a method for making a composition comprising alkanes. The composition is suitable for use as a liquid transportation fuel in general, and jet fuel in particular. The method includes dehydrating a feedstock solution comprising a carbohydrate, in the presence of an acid catalyst, to yield at least one furan derivative compound, in a reaction vessel containing a biphasic reaction medium: an aqueous reaction solution and a substantially immiscible organic extraction solution. The furan derivative compound is then subjected to a self-aldol condensation reaction or a crossed-aldol condensation reaction with another carbonyl compound to yield a beta-hydroxy carbonyl compound and/or an alpha-beta unsaturated carbonyl compound. The beta-hydroxy carbonyl and/or alpha-beta unsaturated compounds are then hydrogenated to yield a saturated or partially saturated compound, followed by hydrodeoxygenation (e.g., dehydrating and hydrogenating) of the saturated or partially saturated compound to yield a composition of matter comprising alkanes.

53 Claims, 12 Drawing Sheets

OTHER PUBLICATIONS

Musau, R. et al., the Preparation of 5-Hydroxymethyl-2-Furaldehyde (HMF) from D-Fructose in the Presence of DMSO, *Biomass* 13:67-74 (1987).

Szmant, H.H. et al., the Preparation of 5-Hydroxymethylfurfuraldehyde from High Fructose Corn Syrup and Other Carbohydrates, *Journal of Chemical Technology and Biotechnology* 31, 135 (1981).

Van Dam, H.E. et al., The Conversion of Fructose and Glucose in Acidic Media: Formation of Hydroxymethylfurfural, *Starch* 38, 95 (1986).

Werpy, T. et al., *Top Value Added Chemicals From Biomass* Available electronically at http://www.osti.gov/bridge (2004).

Antal, M.J.J. et al., Mechanism of formation of 5-(hydroxymethyl(-2-furaldehyde from D-fructose and sucrose, *Carbohydrate Research* 199, 91 (1990).

Benvenuti, F. et al., Heterogeneous zirconium and titanium catalysts for the selective synthesis of 5-hydroxymethyl-2-furaldehyde from carbohydrates, *Applied Catalysis A: General* 193, 147 (2000).

Bicker, M. et al., Dehydration of fructose to 5-hydroxymethylfurfural in sub- and supercritical acetone, *Green Chemistry* 5, 280 (2003).

Carlini, C. et al., Selective saccharides dehydration to 5-hydroxymethyl-2-furaldehyde by heterogenous niobium catalysts *Applied Catalysis A: General* 183, 295 (1999).

Carlini, C. et al., Heterogeous catalysts based on vanadyl phosphate for fructose dehydration to 5-hydroxymethy1-2-furaldehyde, *Applied Catalysis A: General* 275, 111 (2004).

El Hajj, T. et al., Synthèse de hydroxyméthyl-5 furanne carboxaldehyde-2 et de ses dérivés par traitement acide de sucres sur résines échangeuses d'ions, *Bulletin de la Societe Chimique de France* 5, 855 (1987).

Gaset, A. et al.,procédés d'obtention de l'hydroxyméthyl-5 furannecarboxyaldéhyde-2, *Informations Chimie* 212, 179 (1981).

Huber, G.W. et al., Production of Liquid Alkanes by Aqueous-Phase Processing of Biomass-DErived Carbohydrates, *Science* 308, 1446 (2005).

Nakamura, Y. et al., The Dehydratioin of D-Fructose to 5-Hydroxymethyl-2-furaldehyde, *Bulletin of the Chemical Society of Japan* 53, 3705 (1980).

Rigal, L. et al., Selective Conversion of D-Fructose to 5-Hydroxymethyl-2-furancarboxadehyde Using a Water-Solvent-Ion-Exchange Resin Triphasic System, *Industrial Engineering and Chemical Product Research Development* 20, 719 (1981).

Rivalier, P. et al., Development of a continuous catalytic heterogeneous column reactor with simultaneous extraction of an intermediate product by an organic solvent circulating in countercurrent manner with the aqueous phase, *Catalysis Today* 24, 165 (1995).

Seri, K. et al., Catalytic Activity of Lanthanide(III) Ions for the Dehydration of Hexose to 5-Hydroxymethyl-2-furaldehyde in Water, *Bulletin of the Chemical Society of Japan* 74, 1145 (2001).

Roman-Leshkov et al., "Phase Modifiers Promote Efficient Production of Hydroxymethylfurfural from Fructose," *Science*, vol. 312, No. 5782 (2006), 1993-1997.

US 7,880,049 B2

PRODUCTION OF LIQUID ALKANES IN THE JET FUEL RANGE (C8-C15) FROM BIOMASS-DERIVED CARBOHYDRATES

CROSS-REFERENCE TO RELATED APPLICATIONS

This is a continuation-in-part of application Ser. No. 11/757,461, filed Jun. 4, 2007 now U.S. Pat. No. 7,572,925, which claims priority to provisional application Ser. No. 60/811,343, filed Jun. 6, 2006, both of which are incorporated herein.

FIELD OF THE INVENTION

The invention is directed to a process for selectively dehydrating carbohydrates, (preferably sugars, e.g., fructose, glucose, xylose) to yield furan derivatives (such as hydroxymethylfurfural, HMF) and then converting the furan derivatives into a mixture comprising alkanes. The alkane mixture is useful as a transportation in fuel in general and a jet fuel in particular. Particularly advantageous is that the process operates at high sugar concentrations in the reactant feed (preferably from about 10 to about 50 wt %), achieves high yields (>80% HMF selectivity at 90% sugar conversion when using fructose as the reactant), and delivers the furan derivative in a separation-friendly solvent. The conversion of the furan derivatives to an alkane mixture is essentially quantitative. The process uses several two-phase reactors wherein the sugar is dehydrated in an aqueous phase (preferably using an acid catalyst such as HCl or an acidic ion-exchange resin). The furan derivative product is continuously extracted into an organic phase (preferably THF or butanol) thus reducing side reactions.

BACKGROUND

Rising oil prices caused by increasing demand and diminishing supply of crude oil call for the development of alternative ways to supply sustainable fuels and chemicals. In addition, an ever-increasing reliance on foreign oil coupled with political instability in oil-rich countries may jeopardize the fulfillment of domestic energy demands. The effect of high crude oil prices on different sectors of national economies is profound, especially in the transportation sector, which relies heavily on petroleum-derived fuels. Simply put, at present there is no practical alternative to fossil fuels. The aviation industry has recently seen drastic changes in its operating costs. Recently (early 2007), U.S. airline officials noted that jet fuel makes up 30% of long-haul operating costs for airlines, compared with 12-15% two years ago. Indeed, although turbine engines are much more fuel tolerant than gasoline and diesel engines, the engine and fuel systems in jets are more sensitive to the physical and chemical properties of the fuel. Therefore, jet fuel quality is critical to safety, and strict specifications are used to limit the range of fuel properties to insure proper performance during all stages of flight. The large number of physical and chemical properties that must be controlled to produce a fuel that will perform consistently make jet fuel the most rigidly controlled product produced by oil refiners, thereby also making it much more sensitive to price fluctuations.

Many of the stringent requirements of jet fuel are achieved by controlling the fuel composition. Freezing point, combustion properties, thermal oxidation stability, viscosity, and gum formation are significantly influenced by the types and amounts of hydrocarbons in the fuel. Aliphatic hydrocarbons are the primary hydrocarbon components (81%) of jet fuels, and exhibit a range of carbon chain lengths primarily between $C_8$ and $C_{17}$ (9% $C_8$-$C_9$, 65% $C_{10}$-$C_{14}$, and 7% $C_{15}$-$C_{17}$). Therefore, one of the main challenges for non-petroleum jet fuel alternatives is efficiently to attain a hydrocarbon composition in this range. For the mandated specifications for jet fuel, see, for example, Yan et al. (2005) "Aviation Turbine Fuel Specifications and Test Methods," *Energy & Fuels* 19: 1804-1811.

Biomass, an abundant renewable resource that can substitute for a significant fraction of the energy used worldwide, represents the only sustainable source of carbon for renewable liquid fuels. However, obtaining liquid fuels from biomass not only requires the development of novel processing techniques to selectively break down its highly oxygen-functionalized molecules, but it also requires converting them into molecules with the necessary physical and chemical properties. For example, the *Roadmap for Biomass Technologies in the United States* (U.S. Department of Energy, Accession No. ADA436527, December 2002), authored by 26 leading experts, has predicted a gradual shift from a petroleum-based economy to a more carbohydrate dependent economy. This official document predicts that by 2030, 20% of transportation fuel and 25% of chemicals consumed in the United States will be produced from biomass. Such a shift away from petroleum-based technologies requires developing innovative, low-cost separation and depolymerization processing technologies to break down the highly oxygen-functionalized, polysaccharide molecules found in raw biomass, to yield useful bio-derived materials and fuels. In short, abundant biomass resources can provide alternative routes for a sustainable supply of both transportation fuels and valuable intermediates (e.g., alcohols, aldehydes, ketones, carboxylic acid, esters) for production of drugs and polymeric materials. However, unless these alternative routes can be implemented at a production cost roughly comparable to the corresponding production cost when using petroleum feedstocks, the transition will inevitably be accompanied by severe economic dislocations. It is not enough that the transition can be accomplished; to avoid economic upheaval, the transition must be accomplished in an economically feasible fashion.

The present invention provides an economically feasible process for producing transportation fuels from biomass-derived oxygenated hydrocarbons.

SUMMARY OF THE INVENTION

The invention is directed to a method for making a composition comprising alkanes. In the preferred embodiment, the composition is adapted, dimensioned, and configured for use as a liquid transportation fuel in general and a jet fuel in particular. The method comprises first dehydrating a feedstock solution comprising a carbohydrate, in the presence of an acid catalyst, to yield at least one furan derivative compound, in a reaction vessel containing a biphasic reaction medium comprising an aqueous reaction solution and a substantially immiscible organic extraction solution, wherein the aqueous reaction solution, the organic extraction solution, or both the aqueous reaction solution and the organic extraction solution contain at least one modifier to improve selectivity of the dehydration to yield the furan derivative compound. The furan derivative compound is then subjected to at least one self-aldol condensation reaction or a crossed-aldol condensation reaction with another carbonyl compound to yield a beta-hydroxy carbonyl compound and/or an alpha-beta unsaturated carbonyl compound. The beta-hydroxy carbonyl and/or alpha-beta unsaturated compounds are then hydrogenated to yield a saturated or partially saturated compound. Lastly, the saturated or partially saturated compound undergoes hydrodeoxygenation (for example, dehydrated and hydrogenated) to yield a composition of matter comprising a $C_8$ to $C_{15}$ alkane.

In preferred versions of the invention, the self-aldol condensation reaction or the crossed-aldol condensation reaction is run in a monophasic or a biphasic reactor system in the presence of a mineral base catalyst (such as NaOH) or a solid base catalyst comprising magnesium, zirconium, and oxygen. It is also preferred (although not required) that the aqueous reaction solution further comprises at least one salt, thereby yielding a saline aqueous reaction solution. If a salt is present in the aqueous reaction solution, the salt preferably comprises a cation and an anion selected from the group consisting of acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate, and bis-trifluorsulfonimide. This list is exemplary only and non-limiting.

The acid catalyst can be selected from a wide range of acids, including mineral acids, zeolites, silica-, silica-alumina, and titania-based supports functionalized by acid groups, cation exchange resins, Lewis acids, etc. The preferred acid catalysts are selected from the group consisting of heteropolyacids, HCl, $HNO_3$, $H_2SO_4$, $H_3PO_4$, $H_3BO_3$, oxalic acid, levulinic acid, citric acid, $NbOPO_4$, and vanadium phosphate.

In other versions of the invention, the aqueous reaction solution contains the modifier, and the modifier comprises a dipolar, aprotic additive. The modifier may also be selected from the group consisting of water-miscible alcohols, water-miscible ketones, and water-soluble polymers. The modifier may also be present in the organic extraction solution, in which case it is preferred that the modifier is selected from the group consisting of a primary, secondary, linear, branched, or cyclic $C_1$- to $C_{12}$-alcohols.

The organic extraction solution itself comprises any suitable organic solvent (or mixtures thereof) that is substantially immiscible with water. A non-limiting list of suitable organic solvents include water-immiscible, linear, branched, or cyclic alcohols, ethers, and ketones. The organic extraction solution may also comprise a solvent selected from the group consisting of unsubstituted aliphatic and aromatic hydrocarbons and halo-substituted aliphatic and aromatic hydrocarbons.

Another version of the invention comprises first converting a carbohydrate reactant to yield at least one carbonyl compound having an alpha-position hydrogen, in the presence of an acid catalyst, in a reaction vessel containing a biphasic reaction medium comprising an aqueous reaction solution and a substantially immiscible organic extraction solution, wherein the aqueous reaction solution, the organic extraction solution, or both the aqueous reaction solution and the organic extraction solution contain at least one modifier to improve selectivity of the process to yield the carbonyl compound having an alpha-position hydrogen. The carbonyl compound is then subjected to at least one self-aldol condensation reaction or a crossed-aldol condensation reaction with another carbonyl compound in a monophasic or a biphasic reactor system to yield a beta-hydroxy carbonyl compound and/or an alpha-beta unsaturated carbonyl compound. The beta-hydroxy carbonyl and/or the alpha-beta unsaturated carbonyl compounds are then hydrogenated to yield a saturated or partially saturated compound. Lastly, the saturated or partially saturated compound is hydrodeoxygenated (such as dehydrated and hydrogenated) to yield an alkane.

Still another version of the inventive method comprises dehydrating a $C_6$ sugar to yield hydroxymethylfurfural, in the presence of an acid catalyst, in a reaction vessel containing a biphasic reaction medium comprising an aqueous reaction solution and a substantially immiscible organic extraction solution, wherein the aqueous reaction solution, the organic extraction solution, or both the aqueous reaction solution and the organic extraction solution contain at least one modifier to improve selectivity of the dehydration to yield hydroxymethylfurfural. Then, the hydroxymethylfurfural is subjected to at least one crossed-aldol condensation reaction in a monophasic or a biphasic reactor system with an aldehyde or a ketone to yield a beta-hydroxy carbonyl and/or an alpha-beta unsaturated carbonyl having at least seven (7) carbon atoms. The beta-hydroxy carbonyl and/or alpha-beta unsaturated carbonyl is then hydrogenated to yield a saturated or partially saturated compound. Lastly, the saturated or partially saturated compound is hydrodeoxygenated (such as dehydrated and hydrogenated) to yield an alkane having at least seven (7) carbon atoms.

Yet another version of the invention is a method for making a liquid transportation fuel, preferably a jet fuel. Here, the method comprises dehydrating a feedstock solution comprising a carbohydrate, in the presence of an acid catalyst, to yield at least one carbonyl compound, in a reaction vessel containing a biphasic reaction medium comprising an aqueous reaction solution and a substantially immiscible organic extraction solution, wherein the aqueous reaction solution, the organic extraction solution, or both the aqueous reaction solution and the organic extraction solution contain at least one modifier to improve selectivity of the dehydration to yield the carbonyl compound. The carbonyl compound is then subjected to at least one self-aldol condensation reaction or a crossed-aldol condensation reaction in a monophasic or a biphasic reactor system with another carbonyl compound to yield a beta-hydroxy carbonyl compound and/or an alpha-beta unsaturated carbonyl compound. The beta-hydroxy carbonyl and/or alpha-beta unsaturated compounds are then hydrogenated to yield a saturated or partially saturated compound. Then the saturated or partially saturated compound is hydrodeoxygenated (such as dehydrated and hydrogenated) to yield a composition of matter comprising alkanes, wherein the composition of matter is dimensioned and configured for use as a liquid transportation fuel.

The invention is useful for making liquid transportation fuels from renewable biomass reactants. One notable benefit of the invention is that it can be used to make jet fuels from renewable resources without the need for extensive refining. The inventive method can be optimized to yield a composition of matter comprising alkanes that satisfies the mandates specifications for various types of jet fuel (and other types of transportation fuels).

DETAILED DESCRIPTION

Abbreviations and Definitions: The following abbreviations and definitions are used throughout the specification and claims. Words and phrases not explicitly defined herein are to be afforded their standard definition in the art of chemical engineering.

1B=1-butanol.

2B=2-butanol.

Biomass=any plant material, vegetation, or agricultural waste, from any source, that can be used to supply carbohydrates to be used as reactants in the process disclosed herein.

Carbohydrates=Any of a group of organic compounds that includes (without limitation) sugars, starches, celluloses, and gums and serves as a major energy source in the diet of animals. Carbohydrates are produced by photosynthetic plants and contain only carbon, hydrogen, and oxygen atoms.

DCM=dichloromethane.

Dipolar, aprotic additive=a water-soluble compound that: (a) cannot donate labile hydrogen atoms to form strong hydrogen bonds; (b) has a dielectric constant greater than about 15; and (c) has a permanent dipole moment. dimethylformamide, DMSO, NMP, pyrrolidinone, and PVP are examples of dipolar, aprotic additives.

DMF=dimethylfuran.

DMSO=dimethylsulfoxide.

FDCA=2,5-furandicarboxylic acid.

Fur=furfural.

Furan derivative compounds: A compound having the structure:

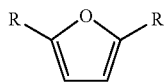

wherein each R is independently selected from the group consisting of hydrogen, $C_1$-$C_6$-alkyl, hydroxy-$C_1$-$C_6$-alkyl, acyl-$C_1$-$C_6$-alkyl, $C_1$-$C_6$-alkylcarbonyl-$C_1$-$C_6$-alkyl, and carboxy-$C_1$-$C_6$-alkyl, and provided the both R's are not simultaneously hydrogen. (Furan itself is the compound where both R groups are hydrogen.) Explicitly included within the phrase "furan derivative" are 5-hydroxymethylfurfural and furfural.

Group VIIIB metal: a metal selected from the group consisting of Fe, Co, Ni, Ru, Rh, Pd, Os, Ir, and Pt.

HMF=5-hydroxymethylfurfural.

MeTHF=methyltetrahydrofuran.

MIBK=methylisobutylketone.

MCM=mobile crystalline materials.

NaCl=sodium chloride

NMP=1-methyl-2-pyrrolidinone.

PBT=polybutyleneterephthalate.

PEG=polyethyleneglycol.

PET=polyethyleneterephthalate.

PVP=poly(1-vinyl-2-pyrrolidinone).

TMF=tetrahydrofuran.

Figure 1:
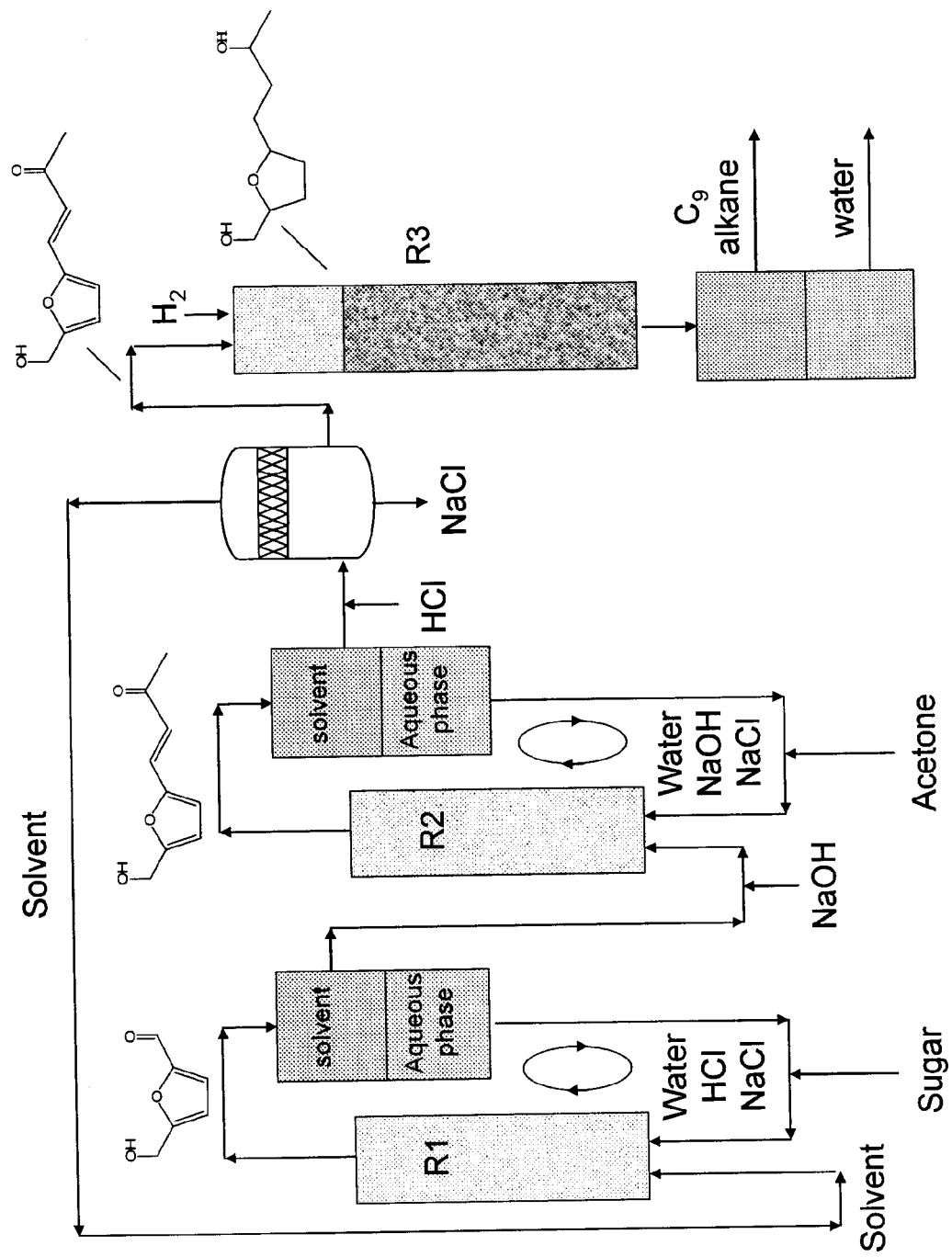
FIG. 1 is a schematic representation showing a first version of the present invention for producing liquid alkanes with targeted chain lengths from biomass-derived carbohydrates.
Figure 2:
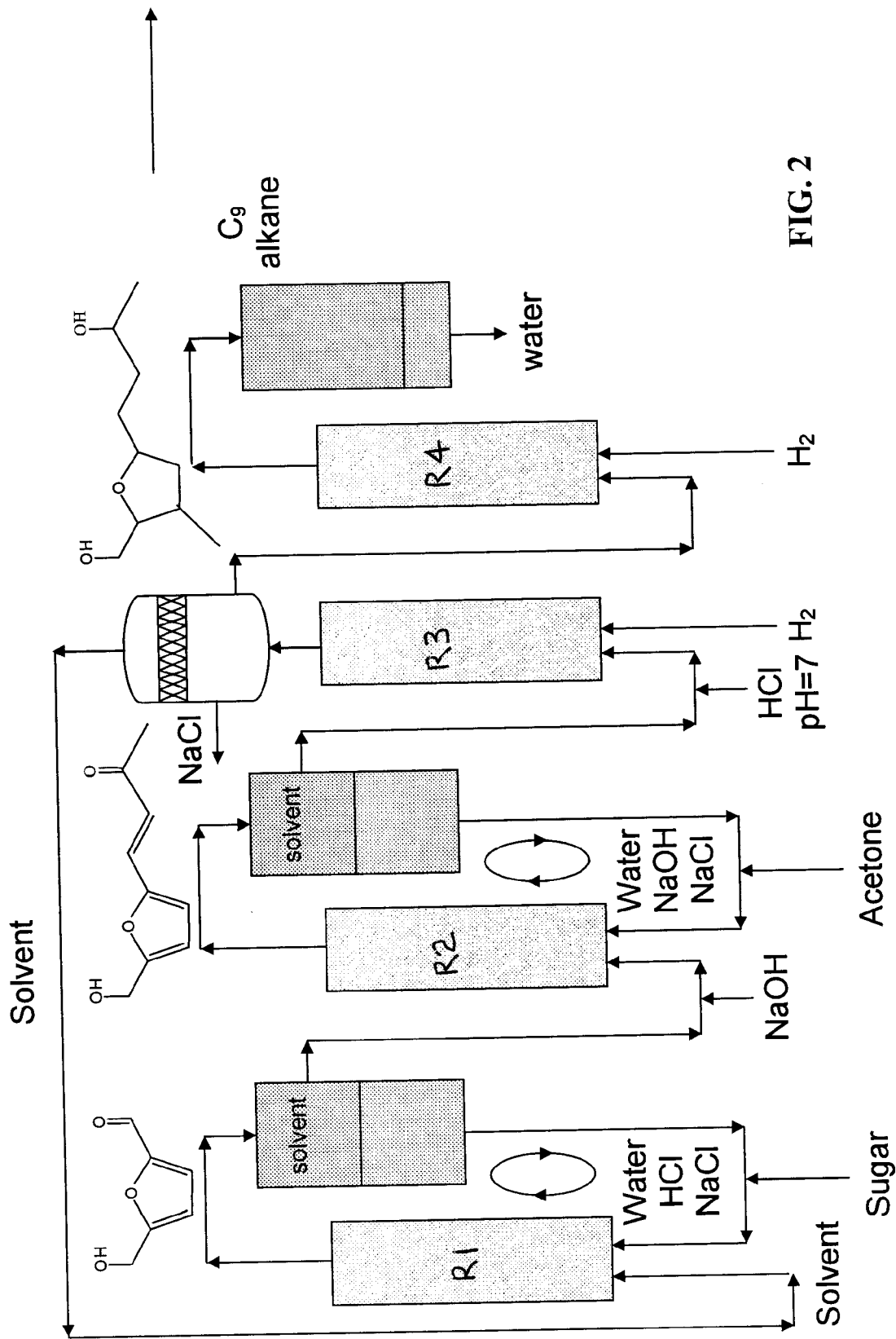
FIG. 2 is a schematic representation showing an alternative version of the present invention for producing liquid alkanes with targeted chain lengths from biomass-derived carbohydrates.

The invention is a process for the catalytic production of liquid alkanes with targeted carbon chain-lengths ranging from $C_8$ to $C_{15}$ from biomass-derived carbohydrates for jet fuel applications. A schematic representation of the process to obtain liquid alkanes is shown in FIGS. 1 and 2. Biomass-derived $C_6$-carbohydrates undergo acid-catalyzed dehydration to produce 5-hydroxymethylfurfural (HMF) in a biphasic system (FIGS. 1 and 2, R1). Next, HMF is upgraded to a $C_9$ monomer and/or a $C_{15}$ dimer via aldol condensation reactions with acetone (FIGS. 1 and 2, R2). (The acetone introduced into R2 can be obtained by fermentation of carbohydrates.) Subsequently, both monomer and dimer components undergo a hydrogenation step followed by a hydrodeoxygenation (such as dehydration/hydrogenation) step to obtain liquid alkanes (FIG. 1, R3; FIG. 2, R3 and R4). The hydrogenation step and the hydrodeoxygenation step can take place in a single reactor, as shown in FIG. 1 (R3), or the two reactions can be performed in sequential reactions in two distinct reactors, as shown in FIG. 2 (R3 and R4).

This catalytic strategy can also be used with $C_5$-carbohydrates to produce analogous $C_8$ and $C_{13}$ compounds. Importantly, the chemistry illustrated in FIGS. 1 and 2 is representative of a large class of biomass-derived compounds containing carbonyl compounds, such as aldehydes, ketones, lactones, and even sugars themselves. Thus, it must be stressed that the chemical structures for HMF and $C_9$ monomer intermediates as depicted in FIGS. 1 and 2 are shown as examples to illustrate the reaction chemistry. Other carbohydrate feedstocks may be used to produce liquid alkanes with targeted carbon chain-lengths ranging from $C_8$ to $C_{15}$.

Thus, the first step in the invention comprises producing a $C_5$ (for example, furfural) or $C_6$ (for example, HMF) furan derivatives by way of acid catalyzed dehydration of pentoses or hexoses, respectively.

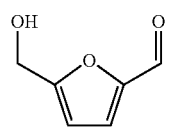

HMF

Furfural

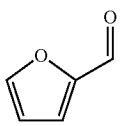

The dehydration reaction is performed in a biphasic reactor comprising a reactive aqueous phase containing an acid catalyst and a sugar, and an extracting phase containing a partially miscible organic solvent (e.g., butanol or THF) that continuously extracts the furan-based product. (See the Examples for full details.) Importantly, the addition of a salt to the aqueous phase provides crucial advantages: first, it improves the partitioning of the furan derivative into the extracting phase, leading to increased yields; and second, it creates biphasic conditions with solvents that in the absence of salt would create monophasic systems (e.g., THF, ethanol, etc.). This effect is known as the salting-out effect, whereby electrolytes alter the intermolecular bonding interactions between liquid components, decreasing the mutual solubility of aqueous and organic components. The dehydration of a 30 wt % fructose solution (on a salt-free basis) using HCl as the acid catalyst and THF as the extracting solvent generates 55 g of 5-hydroxymethylfurfural (HMF) per liter of THF, which corresponds to an 80% reaction yield (defined as moles of HMF produced/initial moles of fructose). Similarly, the dehydration of 30 wt % xylose under the same conditions generates 60 g of furfural per liter of THF, which corresponds to a 82% reaction yield.

Reaction Scheme 1: Condensation of furfural with acetone to form the furfural monomer (F-mon).

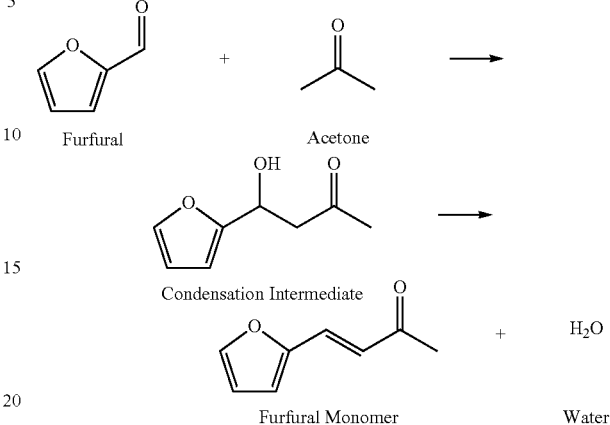

Furfural and acetone first react to form a condensation intermediate, which loses a molecule of water to form a furfural monomer (referred to herein as "F-mon"). The furfural monomer can undergo a second condensation with furfural to create a second condensation intermediate, which also loses a water molecule to form a furfural dimer (referred to herein as "F-dim"). See Reaction Scheme 2. The functionalized groups in HMF react with acetone in a nearly identical matter to those in furfural, and the $C_9$-monomers and $C_{15}$-dimers obtained from HMF follow an analogous chemical pathway.

Reaction Scheme 2: Aldol condensation of furfural monomer with furfural to form the furfural dimer (F-dim).

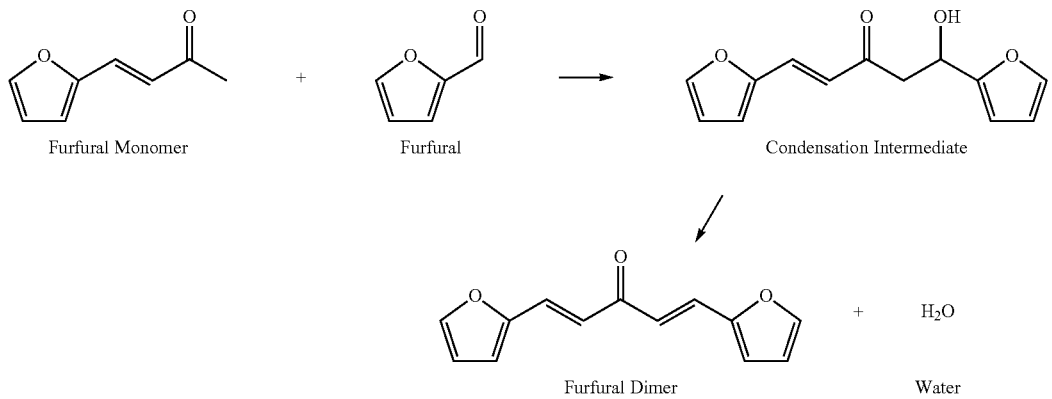

Once separated, the organic solvent containing the furan derivative is next upgraded by means of aldol condensation in reactor R2. (See FIGS. 1 and 2.) Aldol condensation is a reaction that involves carbon-carbon (C—C) bond coupling between two carbonyl-containing compounds to form larger organic molecules. This reaction is generally carried out in the presence of base catalyst at low temperatures (298-353 K). Reaction Scheme 1 depicts the chemical pathways followed to produce $C_8$-monomers and $C_{13}$-dimers from furfural and acetone.

In the present invention, the aldol condensation is carried out in a novel biphasic system. In a typical (and preferred) furfural-based experiment, acetone is added to a solution of furfural in THF, which is then combined with a salt-saturated water solution (preferably NaCl) containing a homogeneous base catalyst (preferably NaOH). The mixture spontaneously separates into two phases, a THF-rich organic phase and a water-rich aqueous phase, with furfural and acetone partitioning between both phases. As the reaction proceeds in the aqueous phase, the organic phase extracts the monomer and dimer units as they are formed. If the organic phase were absent, the monomer and dimer units would precipitate out of solution due to their limited solubility in water, thereby complicating further processing. Therefore, the use of a biphasic system not only eliminates solubility problems in the reaction system, but also leads to high concentrations of reaction intermediates in the organic extracting solvent, which leads in turn to the production of a concentrated liquid effluent stream of alkanes.

Figure 3:
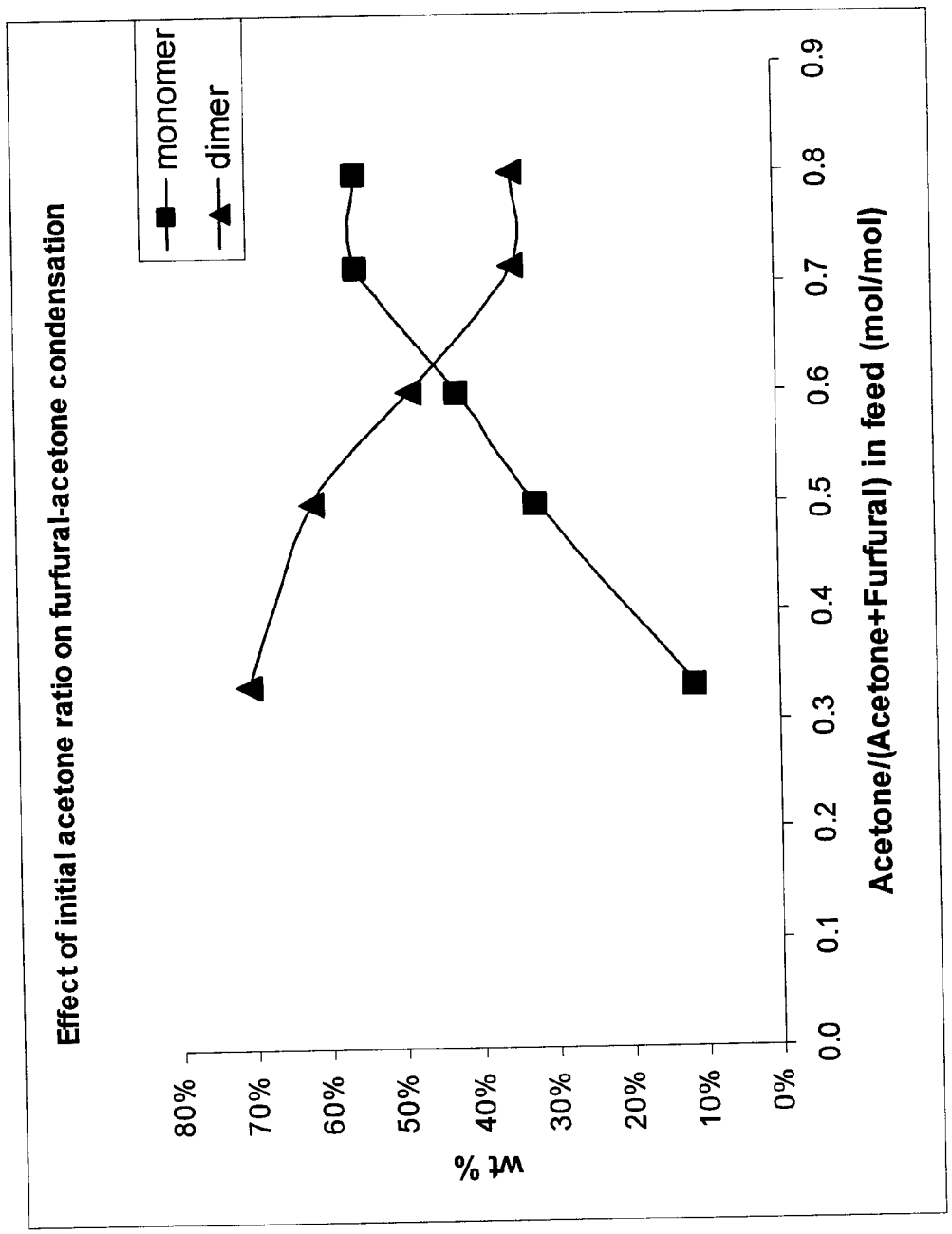
FIG. 3 is a graph depicting the effect of adjusting the molar ratio of acetone-to-furfural on the composition of the final condensation product.
Figure 4:
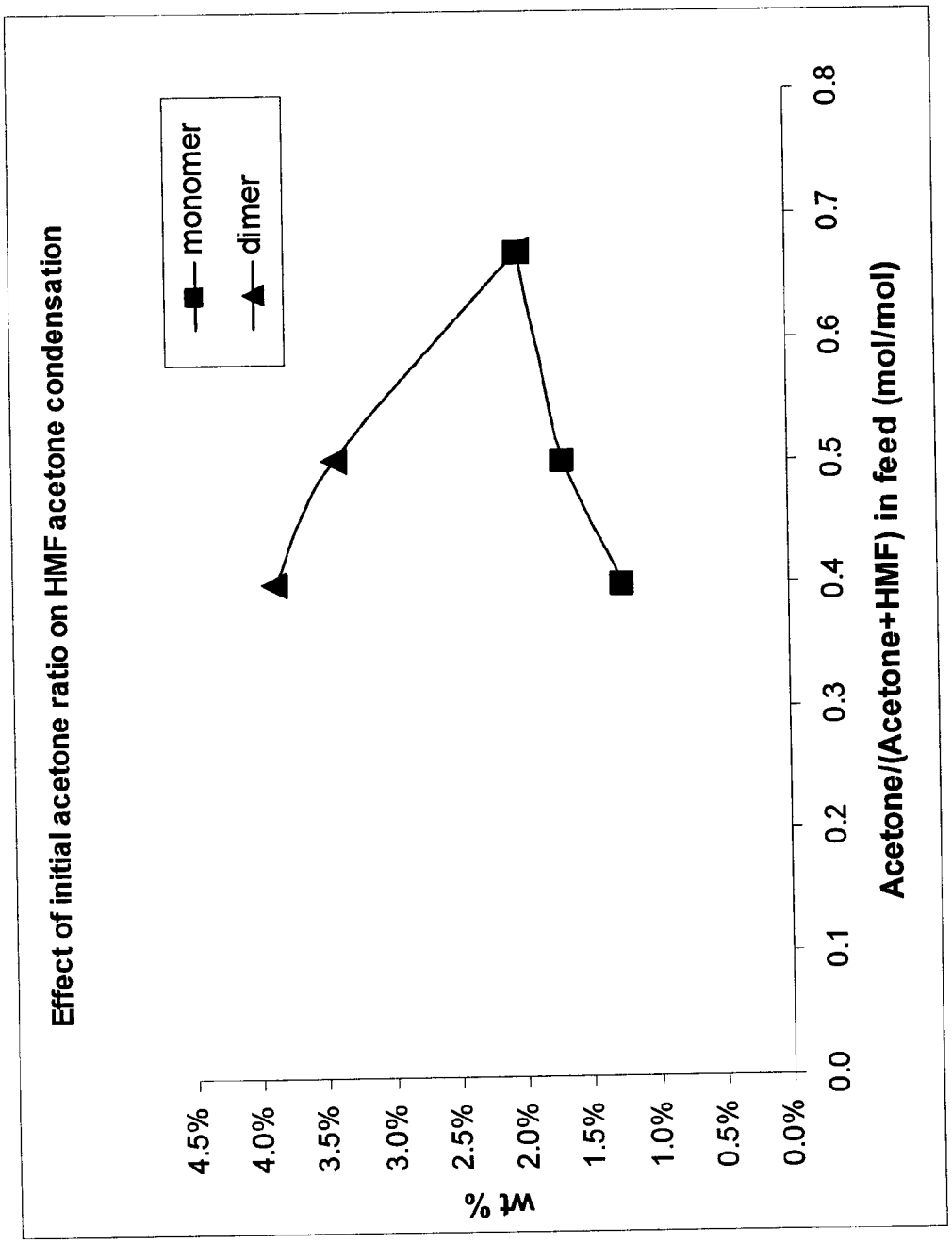
FIG. 4 is a graph depicting the effect of adjusting the molar ratio of acetone-to-HMF on the composition of the final condensation product.

Several factors affect the relative distribution of monomer and dimer units. The amount of monomer formed relative to the amount of dimer can be controlled by adjusting the ratio of acetone to furfural/HMF (A/F or A/H). As shown in FIGS. 3 and 4, when the ratio increases, the distribution shifts toward more monomer units, while decreasing the ratio shifts the distribution toward more dimer units. Other factors that influence the monomer/dimer distribution include the relative partitioning of acetone, HMF, and furfural between both phases at different temperatures, as well as transport limitations dictated by the interfacial surface area formed upon stirring. The material balance of this step shows a recovery of feed as products of approximately 85%.

Figure 5:
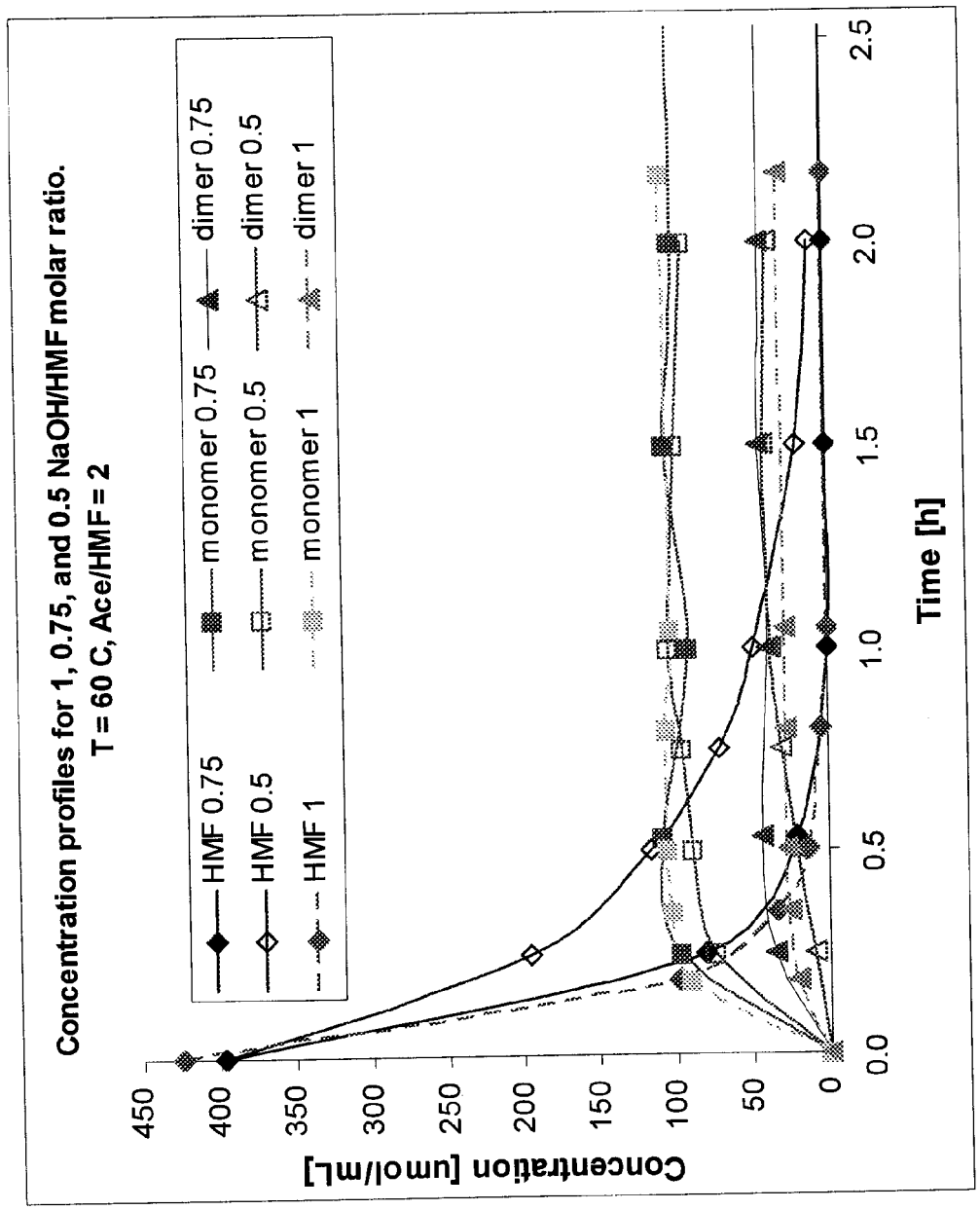
FIG. 5 is a graph depicting the effect of adjusting the molar ratio of NaOH-to-HMF at constant temperature and constant molar ratio of acetone-to-HMF

The amount of catalyst affects the rate of reaction but does not change the relative distribution of monomer and dimer. See FIG. 5. When the molar ratio of NaOH/HMF is decreased from 1 to 0.75, the rate of HMF disappearance does not change significantly. However, when the level is lowered to 0.5, the rate of HMF disappearance decreases considerably, as does the formation of monomer and dimer. When the reaction reaches high conversion, for all NaOH/HMF molar ratios, the same product distribution is obtained. These results suggest that at this temperature (60° C.), a 0.75 ratio is preferred for fast HMF conversion.

Figure 6:
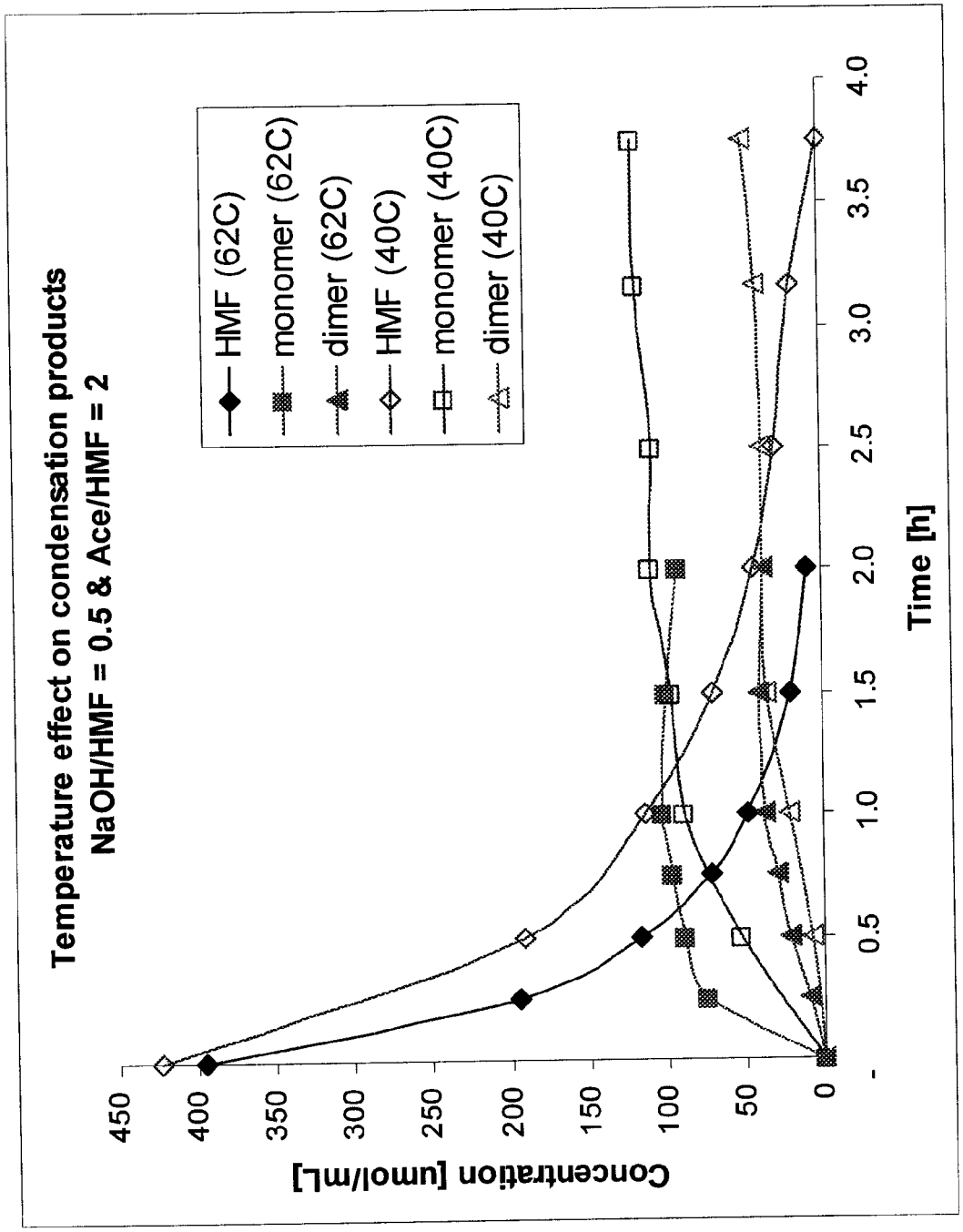
FIG. 6 is a graph depicting the effect of changing temperature at constant acetone-to-HMF and NaOH-to-HMF molar ratios.

In a similar fashion, the proportions of monomer and dimer are not affected by changes in temperature when the acetone: HMF and the NaOH:HMF ratios are constant. See FIG. 6. An increase in temperature from 40° C. to 62° C., however, increases the rates of formation of monomer and dimer species. These results suggest that higher temperatures are preferred to obtain faster conversion without jeopardizing selectivity. In combination with the results presented in FIG. 5, these results also suggest that at higher temperatures and lower catalyst levels, the same product distribution can be obtained.

The next step in the invention comprises hydrogenation of the monomer and dimer species over a metal catalyst in the presence of hydrogen. This step is employed to hydrogenate some of the double bonds present in both monomer and dimer species, thereby suppressing the rates of undesirable side reactions between these double bonds to form carbonaceous deposits in the subsequent processing step in which alkanes are formed. When using furfural, three species that can be hydrogenated are present after performing aldol condensation: furfural, F-mon and F-dim. Furfural contains three double bonds, while F-mon and F-dim contain four and seven double bonds, respectively. When a molecule is hydrogenated, the various double bonds are hydrogenated sequentially and/or at different rates. The following orders of hydrogenation were deduced from gas chromatography mass spectroscopy (GCMS) analysis. For furfural the first bond hydrogenated is the aldehyde group (the carbon-oxygen bond). The two double bonds in the ring are hydrogenated next in rapid succession. The first bonds to be hydrogenated in F-mon and F-dim are the carbon-carbon bonds not found within a ring. F-mon contains one bond of this nature and F-dim contains two. For F-mon, the two double bonds in the ring are hydrogenated next. For F-dim, it is known that the four double bond in the two rings are next to react. The last bond to be hydrogenated in both F-mon and F-dim is the ketone species (the carbon-oxygen bond). All these reactions and the nomenclature for the intermediates are given in Reaction Scheme 3:

Reaction Scheme 3: Reactive pathways for the hydrogenation of furfural, F-mon, and F-dim.

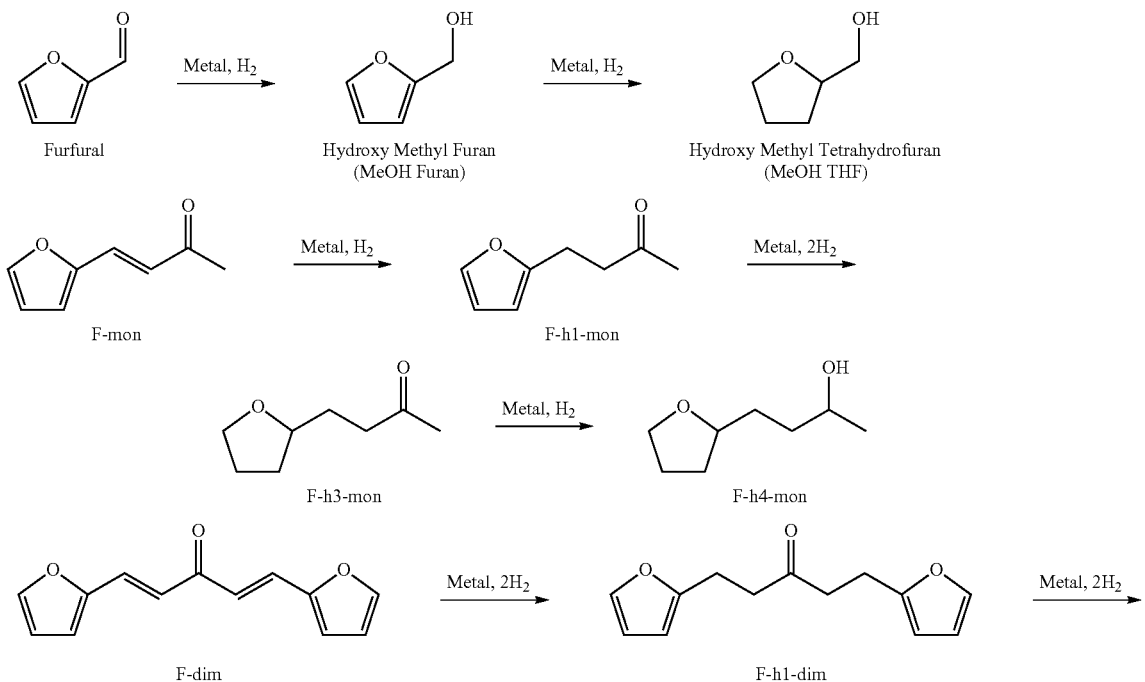

-continued

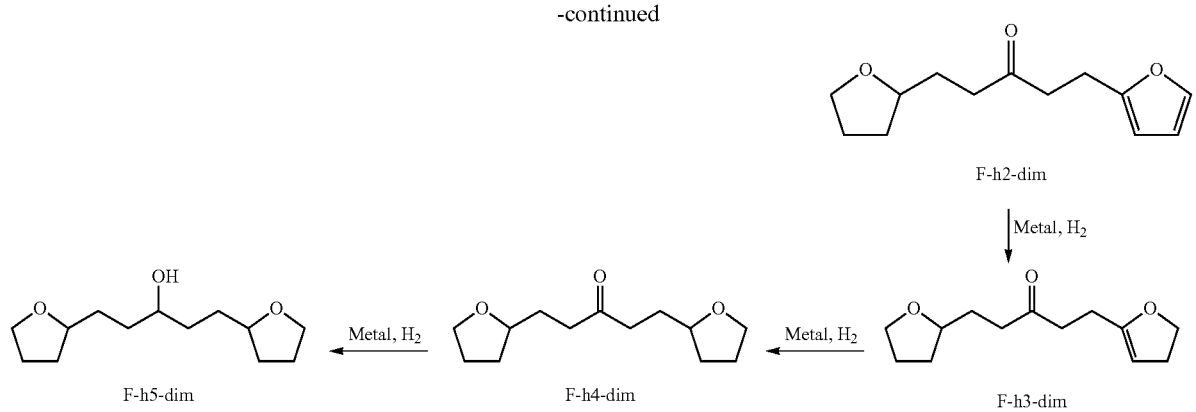

Figure 7:
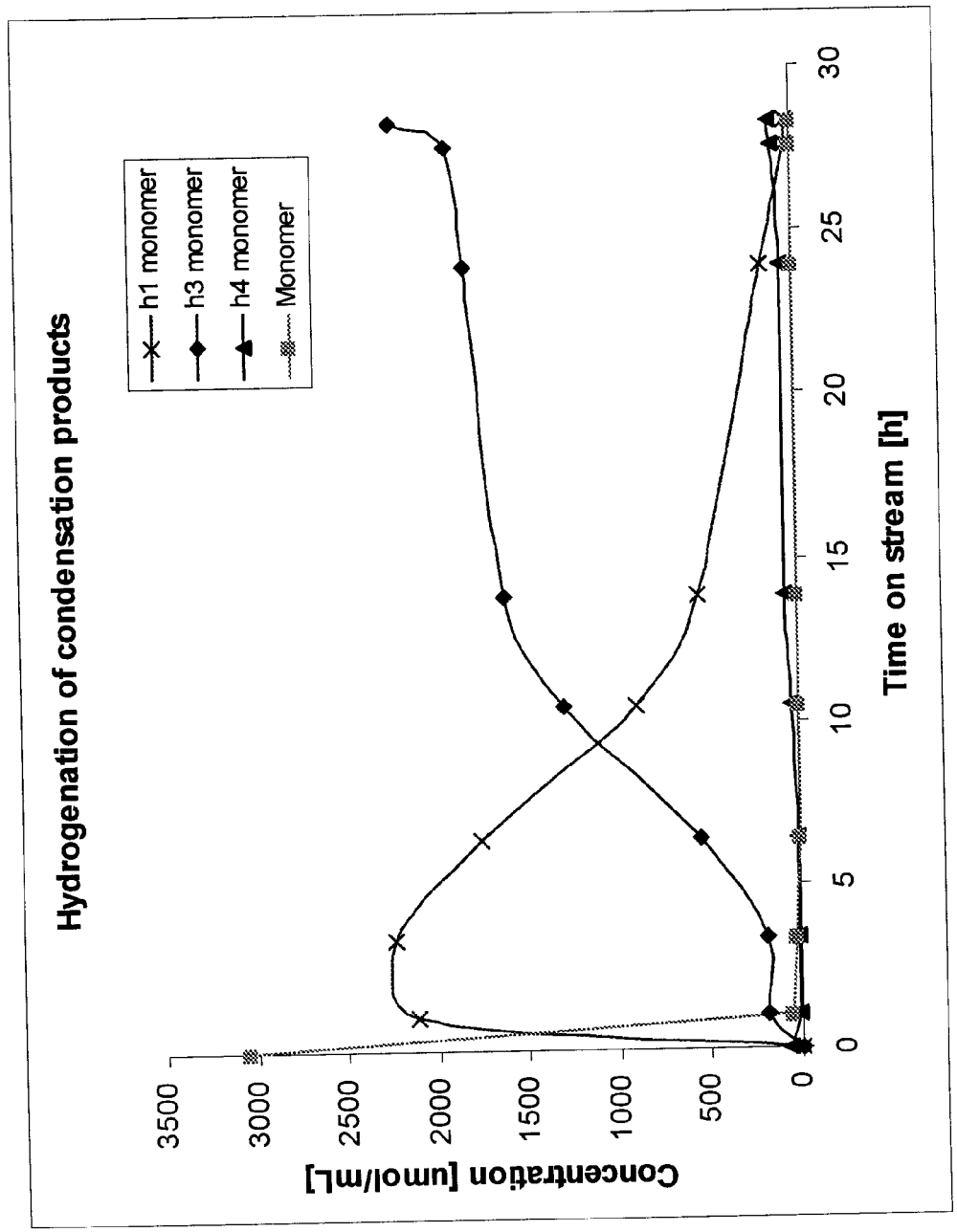
FIG. 7 is a graph depicting the hydrogenation of furfural monomer in a batch reactor using a Pd—$Al_2O_3$ catalyst under high-pressure hydrogen.
Figure 8:
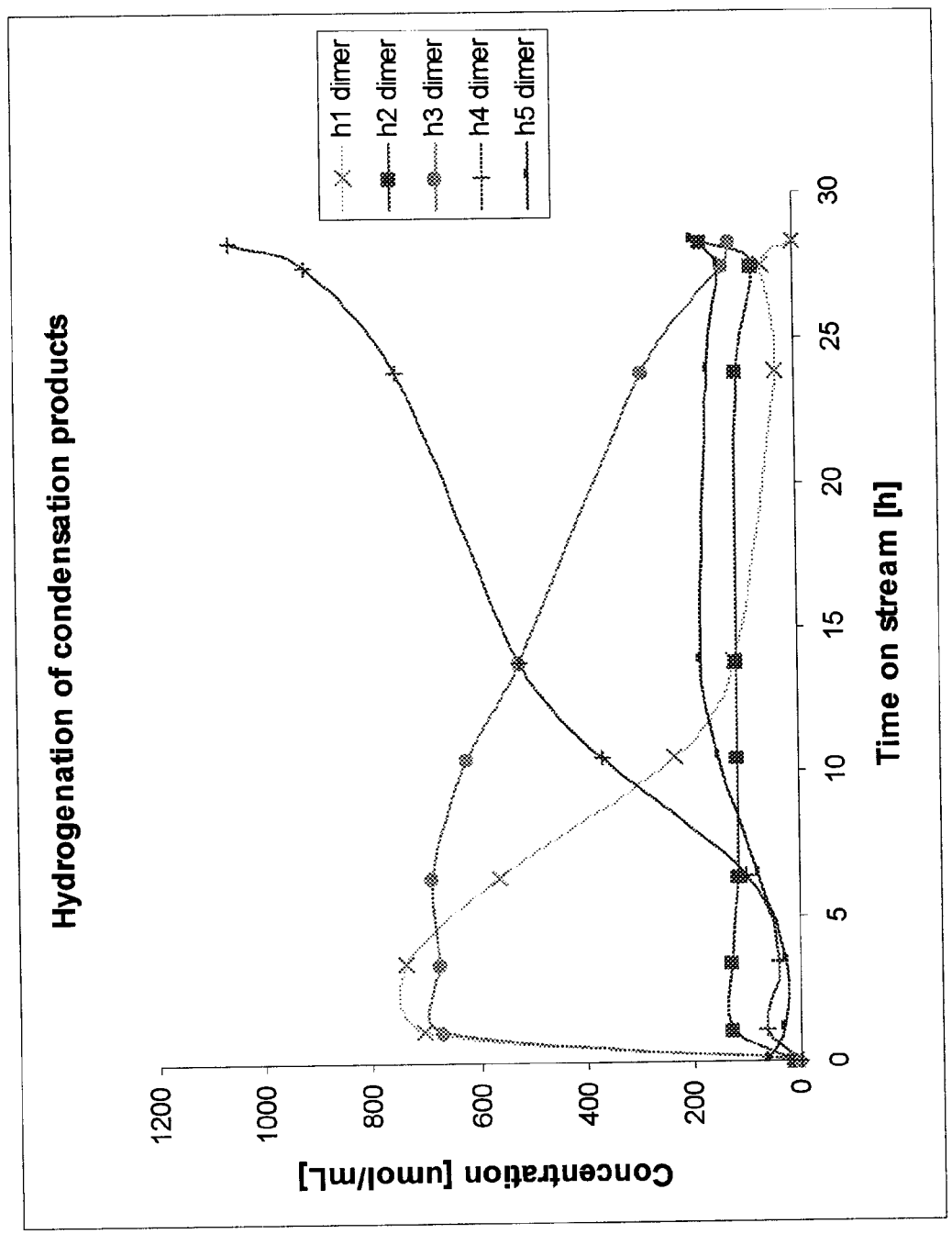
FIG. 8 is a graph depicting the hydrogenation of furfural dimer in a batch reactor using a Pd—$Al_2O_3$ catalyst under high-pressure hydrogen.

The hydrogenation steps of the above reactive pathways were studied in a batch reactor, without the use of a solvent. In particular, the organic solvent was removed by evaporation and a highly concentrated feed was then used. FIGS. 7 and 8 show a representative example of one of these runs using Pd/Al$_2$O$_3$ as the hydrogenation catalyst at a temperature of 140° C. The concentrations of F-dim and F-mon decrease to zero rapidly. The first hydrogenated species then increases in concentration. After a short period, the concentration of this first species reaches a maximum and then begins to decline as it is hydrogenated further to the next species. This same trend continues for all the species until they reach begin to reach the ketone form (F-h4-dim, F-h3-mon). The final hydrogenation step to the alcohol form (especially F-h5-dim but also F-h4-mon) is generally the slowest. Increasing the temperature up to 160° C. slightly increased the rate of hydrogenation without any visible negative effects. With this information, the hydrogenation was next performed in a flow reactor under similar reaction conditions.

Figure 9:
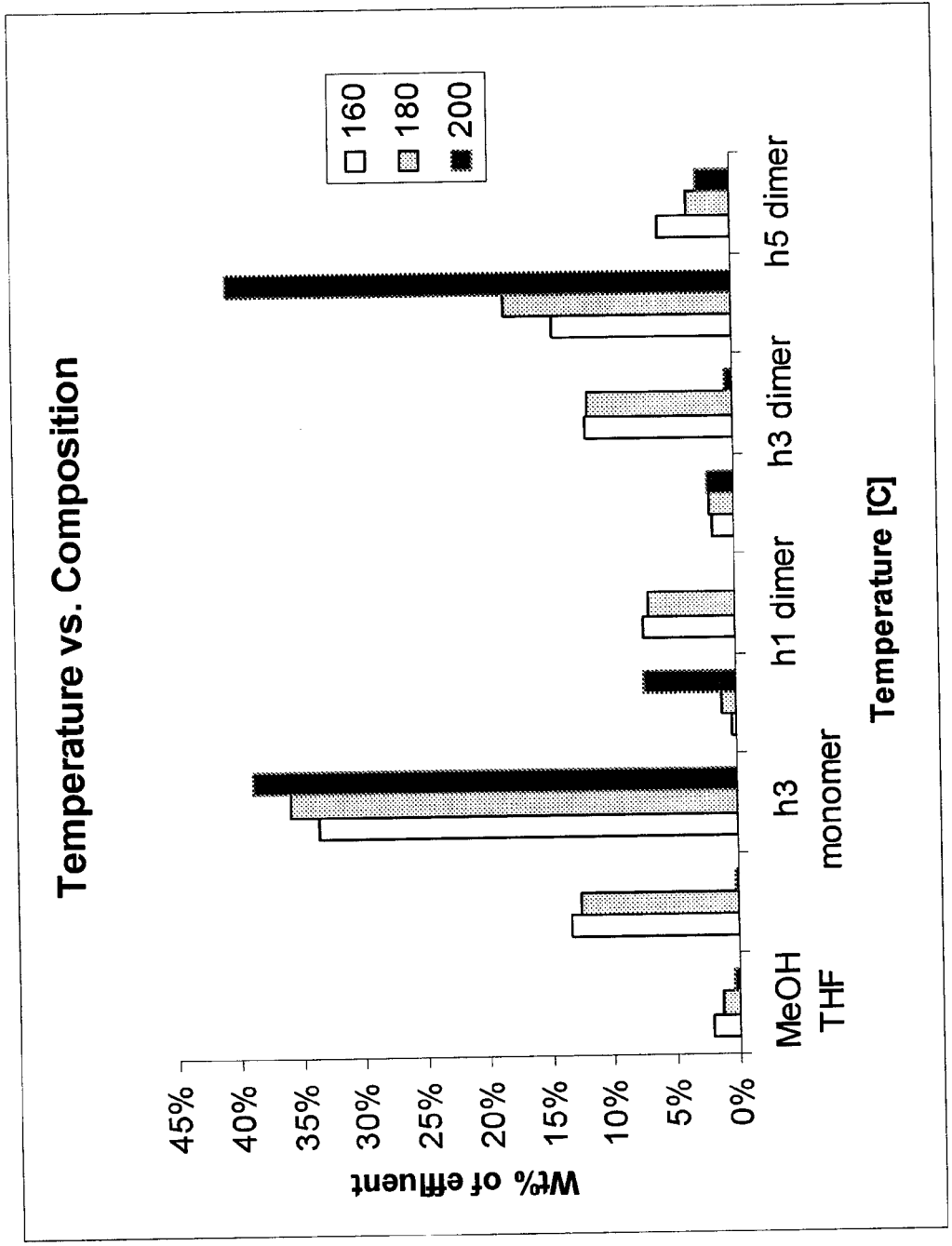
FIG. 9 is a histogram depicting the effect of temperature on the effluent steady-state concentration of furfural, furfural monomer, and fufural dimer hydrogenation over a Pd—$Al_2O_3$ catalyst in flow mode.

The Pd/Al$_2$O$_3$ catalyst was used in a flow reactor to carry out the hydrogenation of furfural, F-mon and F-dim species at steady state reaction conditions. FIG. 9 shows the steady state outlet concentrations at three different temperatures. At a temperature of 160° C. the F-mon is hydrogenated to the F-h1-mon and F-h3-mon forms. Likewise the F-dim is converted to the F-h1-dim, F-h3-dim, and F-h4 dim forms. Increasing the temperature to 180° C. increased the steady state concentrations of the more hydrogenated forms. Increasing the temperature to 200° C. further increased the rate of hydrogenation. The effluent at this temperature consisted of mostly the ketone forms of the monomer and dimer, F-h3-mon and F-h4 dim.

The Pd/Al$_2$O$_3$ catalyst showed good stability and reactivity while on stream, as no major deactivation of the catalyst was observed over a period of one (1) week. Also total material balances show that the carbon balance of the hydrogenation reactions are close to 100%. The effluents from this hydrogenation were subsequently reacted in a final step to form a mixture comprising alkanes (e.g., transportation fuel in general, jet fuel in particular).

Once the hydrogenation step is completed, the formation of liquid alkanes is accomplished with a bifunctional catalyst comprising an acidic support and a metal catalyst. The acidic support causes dehydration of the reacting species to form a carbon-carbon double bond and water. The double bond is then hydrogenated over the metal site. This process is repeated until the fully-saturated alkane is formed as shown for the F-h5-dim species in Reaction Scheme 4:

Reaction Scheme 4: Dehydration/hydrogenation over a bifunctional catalyst (formation of tridecane, C$_{13}$H$_{28}$ from the fully hydrogenated form of furfural dimer is shown).

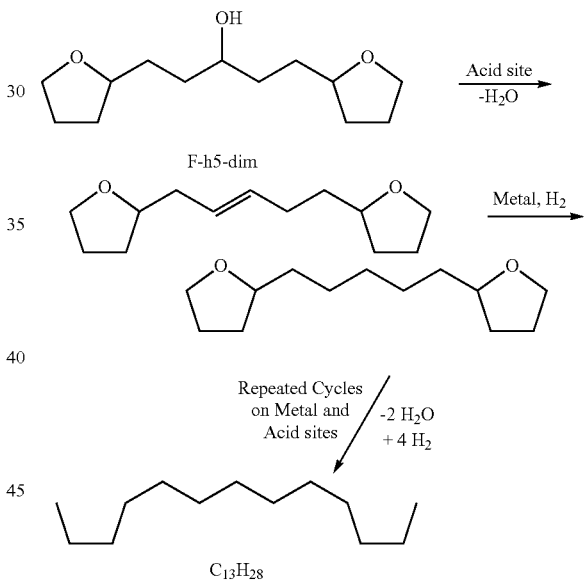

If the feed to this final step is not fully hydrogenated (i.e., if the effluent from the hydrogenation is not solely in the F-h-4-mon and F-h5-dim forms), the metal in this step will hydrogenate these species. However, if the feed contains too many double bonds, the final step cannot accomplished with high yields due to the formation of undesirable carbonaceous deposits on the catalyst.

A bifunctional catalyst comprising Pt on an acidic support is effective for cleavage of C—O bonds and ultimately for the formation of alkanes. However, this catalyst can also lead to the cleavage of C—C bonds (at a lower rate). Because of this latter reactivity, the final step in making alkanes does not solely yield C$_{13}$, C$_8$, and C$_5$ alkanes (from F-dim, F-mon, and furfural, respectively). Instead it primarily yields these three alkane species, along with lesser amounts of smaller alkanes that have lost one or two carbon atoms (C$_{12}$ and C$_{11}$, C$_7$ and C$_6$, and C$_4$ and C$_3$), accompanied by the formation of CO$_2$ or light alkanes such as methane ($CH_4$) or ethane ($C_2H_6$). The lighter species do not remain in the liquid phase, rather they are swept into the gas phase where they are analyzed.

The preferred solid acid supports include niobium phosphate ($NbOPO_4$, most preferred) as well as silca/alumina-based supports. The niobium phosphate support is most preferred because it has shown higher activity than amorphous silica/alumina and better water tolerability than zeolites (data not shown). Other catalysts for hydrodeoxygenation include Ni, Co, and/or Mo deposited onto acidic supports, such as alumina, and these catalysts could be used in their reduced or sulfided forms.

As in the hydrogenation step, the final hydrodeoxygenation step in performed without the use of a solvent. If the feed is completely reacted to alkanes; the only species that should be present in the effluent are the product alkanes and the water from dehydration. Because these two liquids are immiscible, they will spontaneously separate giving two layers. Even if the species are not fully reacted to alkanes, the outlet liquid will still spontaneously separate into an organic layer and a water layer.

Figure 10:
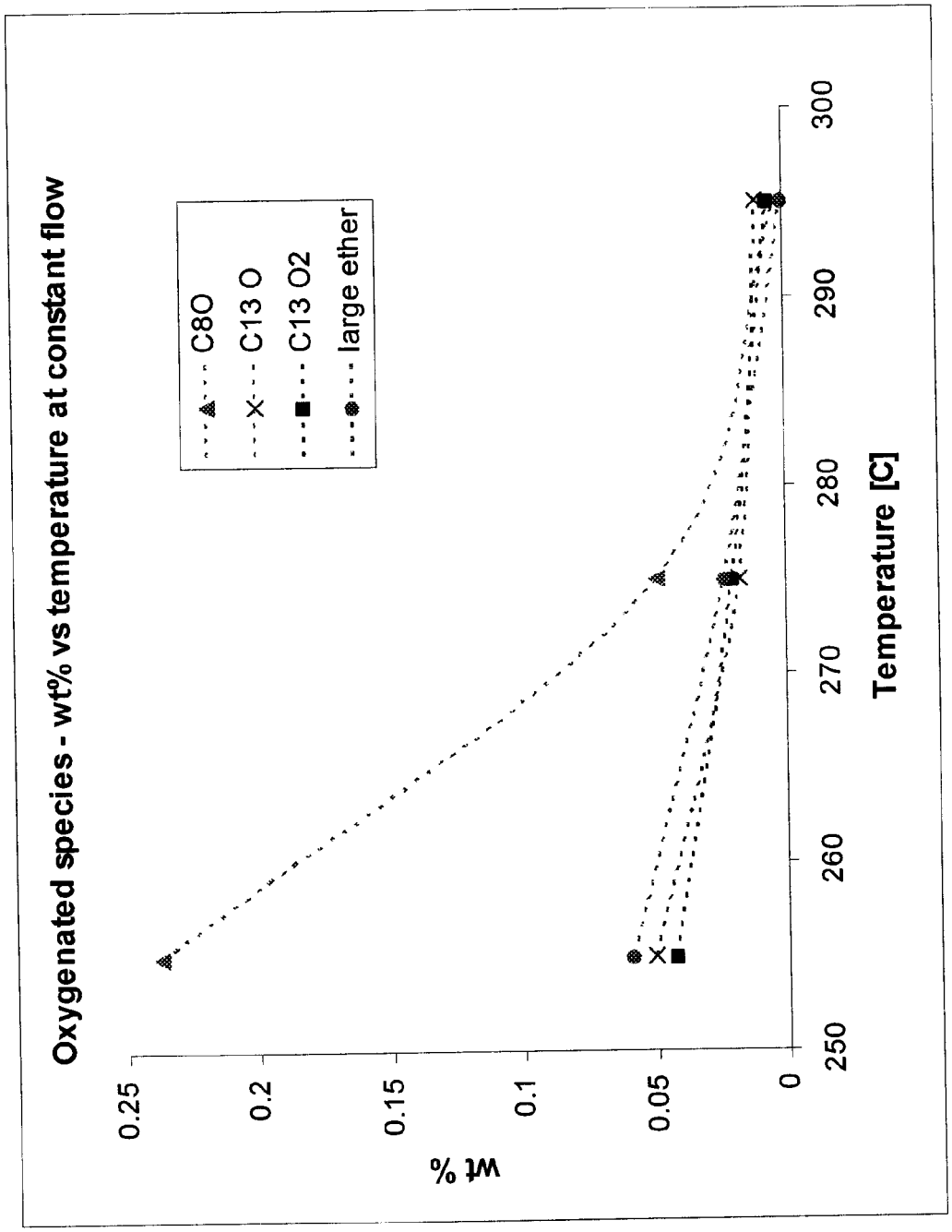
FIG. 10 is a graph depicting the effect of temperature on the concentration (wt %) of oxygen-containing species at a constant flow rate.
Figure 11:
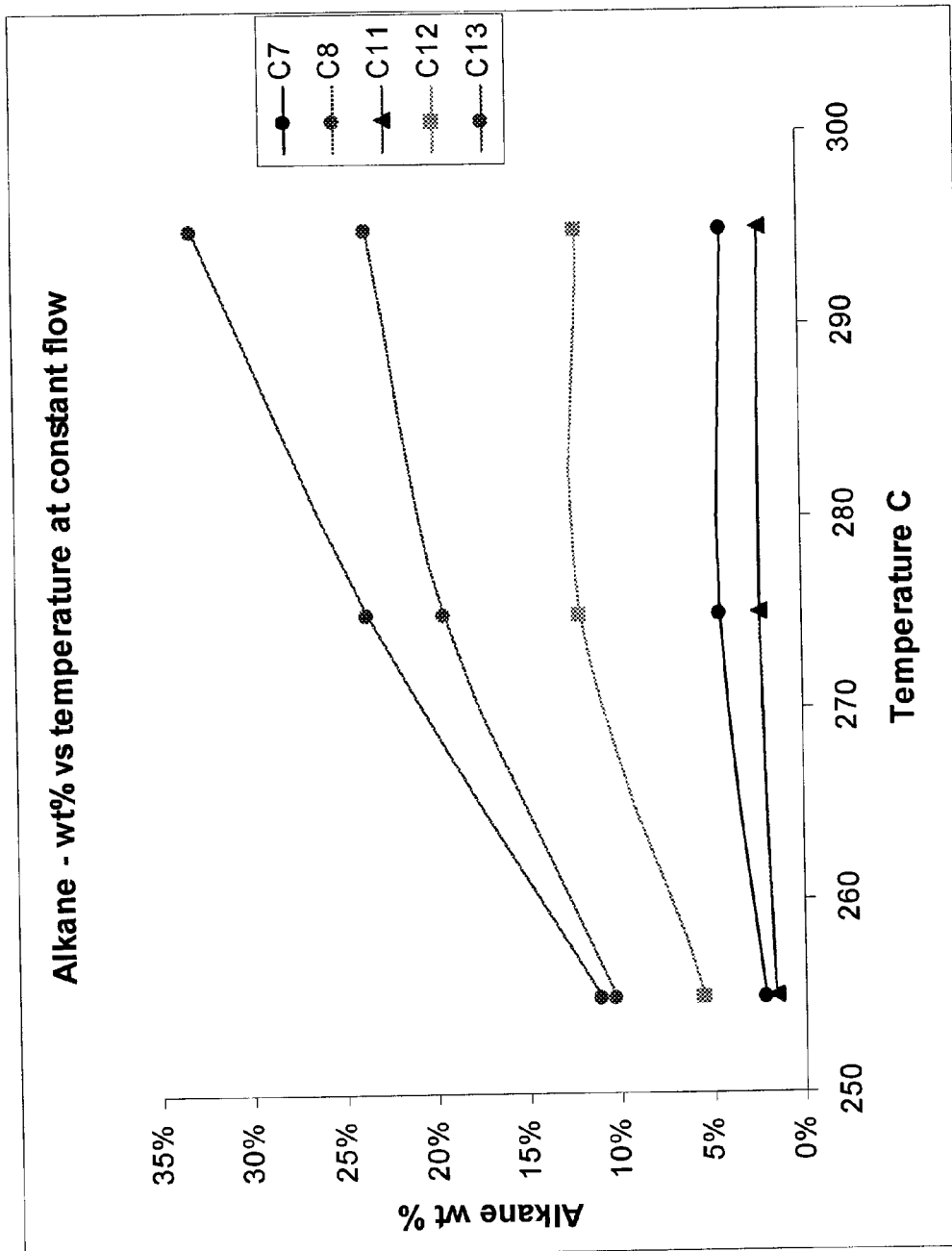
FIG. 11 is a graph depicting the effect of temperature on the concentration (wt %) of alkanes in the organic phase at a constant flow rate.

Under the correct operating conditions, the reaction can be run to completion. The extent of reaction was found to be a function of temperature. FIGS. 10 and 11 show how the alkane and oxygenated species change as a function of temperature. At lower temperatures (255° C. and 275° C.), the organic layer was comprised of both alkanes and oxygen containing species. These oxygen-containing species were identified as intermediates in the formation of alkanes. For simplicity, the oxygen-containing compounds are labeled with the number of carbon and oxygen atoms they contain. From FIG. 10 it is clear that as the temperature is increased, the concentration of the oxygen-containing compounds decreases significantly. At 295° C., the oxygenated species account for less than 2 wt % of the total alkane layer. The remaining 98 wt % of this layer comprises pure alkanes.

FIG. 11 shows how the alkane concentration changes with temperature at the same points as FIG. 10. While the concentration of oxygenated compounds decreases, the concentrations of tridecane ($C_{13}H_{28}$) and n-octane ($C_8H_{10}$) steadily increase. The concentrations of the other shorter alkanes (those that have lost one or two carbons from C—C bond cleavage) increase as reaction temperature rises from 255° C. to 275° C., and they remain constant between 275° C. and 295° C.

Figure 12:
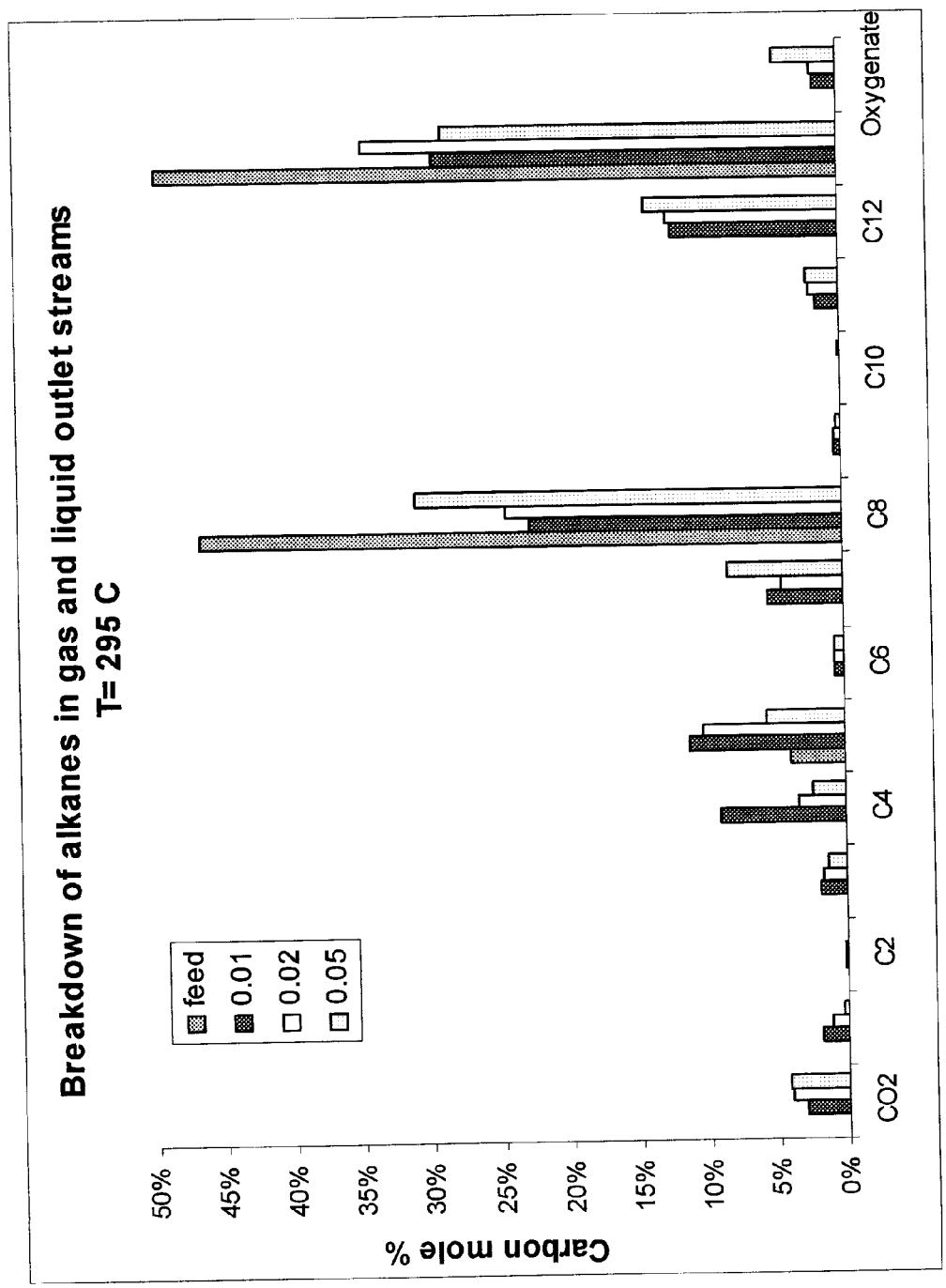
FIG. 12 is a histogram depicting the molar carbon breakdown of the feed and effluent streams at various inlet flow rates at a temperature of 295° C.

At the higher temperature, the effect of flow rate through the reactor was studied. FIG. 12 contains the final distribution in the products of all the inlet carbon (given as mole % C) at 295° C. as a function of flow rate (0.01, 0.02, and 0.05 mL/min). Several trends are apparent. First as the flow increased, the amount of lighter alkane products decreased. This behavior is most clearly seen by observing the decrease in molar carbon concentration of $C_3$, $C_4$ and $C_5$ as the flow rate is increased. This same trend can be seen by examining the increase in molar carbon concentration with the increase in flow rate in $C_7$, $C_8$, $C_{11}$ and $C_{12}$. The second trend is that as the flow rate is increased, the amount of oxygen-containing species also increases. However, even at a flow rate of 0.05 mL/min, the concentration of oxygenates is still less than 5%.

All of these feeds processed at 295° C. led to the formation of an effluent stream that is predominantly comprised of alkanes. The small amount of oxygenates remaining are chemically similar to alkanes and would not need to be separated if this effluent were to be used as a fuel. As with the hydrogenation step, the material balances are close to 100% for this final reaction step.

The present invention thus demonstrates that liquid alkanes in a targeted range from $C_8$-$C_{15}$ can be produced from biomass-derived carbohydrates. The invention not only provides a route for using renewable biomass resources to diminish the reliance on petroleum-based liquid fuels, but it also produces a fuel with a specific range of carbon-atom chain lengths without the use of refining techniques. This latter feature makes the invention especially attractive for producing alkane mixtures having defined characteristics, such as jet fuel, where specific physical properties are required (e.g., high energy density with narrow molecular weight distribution), but are unattainable with current biofuels.

Going into greater detail, in the first step of the present invention, a carbohydrate, preferably a simple sugar such as glucose, fructose, xylose, and the like, or more complex carbohydrates such as starch, cellobiose, sucrose, inulin, xylan, and the like, is dehydrated, optionally in the presence of an acid catalyst, to produce furan derivatives, such as HMF and various byproducts. Although evidence exists supporting both open-chain and cyclic fructofuransyl intermediate pathways, it is clear that the reaction intermediates and the furan derivative products degrade via processes such as fragmentation, condensation, rehydration, reversion, and/or additional dehydration reactions The present invention yields alkane mixtures via an intermediate composition comprising furan derivative compounds. The method addresses the key furan derivative production limitations using a modified biphasic reaction system. In short, the method of the present invention maximizes production of the desired furan derivative compounds, using any type of carbohydrate (but most preferably simple sugars) as the reactant. Specifically, the present invention includes a process that vastly improves the selectivity for furan derivatives such as HMF (defined as the moles of HMF produced divided by the moles of carbohydrate reacted) of an acid-catalyzed dehydration of concentrated (10-50 wt %) carbohydrate feeds by adding modifiers to one or both phases in a biphasic reaction solution (an aqueous reaction phase and a non-aqueous extraction phase). When using specific two-phase systems (described herein below), most notably when the organic phase is dichloromethane and the aqueous reaction phase is a mixture of water and DMSO, the acid catalyst can be omitted entirely. In this particular biphasic system, furan derivative compounds can be produced at high selectivities and conversion rates without adding an acid catalyst.

In the preferred embodiment, the reactive aqueous phase containing the acid catalyst and the carbohydrate reactant (preferably a sugar) is optionally modified with one or more modifiers consisting of metal salts (preferably NaCl) and/or dipolar, aprotic additives (preferably DMSO and/or 1-methyl-2-pyrrolidinone (NMP)) and/or a hydrophilic polymer (preferably poly(1-vinyl-2-pyrrolidinone) (PVP)). The aqueous-phase-immiscible organic phase (preferably THF, butanol or MIBK) used during the reaction (to extract the furan derivative product) is preferably modified with a $C_1$- to $C_{12}$-alcohol, more preferably a primary or secondary, linear, branched, or cyclic $C_3$- to $C_8$-alkanol, and most preferably 2-butanol. The ratio of relative volumes of the organic and aqueous phases in the reactor ($V_{org}/V_{aq}$), as well as the ratio of the product concentration in the organic layer to that in the aqueous layer (defined as the extraction ratio, R) proved to be important variables in the process (as described below). Upon completion of the dehydration reaction, both phases can be separated for efficient product isolation. Although various acid catalysts can be used to perform the dehydration reaction, HCl is preferred because it showed the highest HMF selectivity of the common mineral acid catalysts.

The Reactor: Reactor systems suitable for carrying out the present invention are illustrated schematically in FIGS. 1 and 2. The reactor system includes one or more biphasic reactor vessel circuits, R1, R2, etc. each including a reactor section and a solvent separator. These components (as well as the other components described later) are connected by conventional conduits, which are depicted as arrows in FIGS. 1 and 2. Any number of conventional valves, pumps, sampling ports, injection ports, etc., explicitly not shown in FIGS. 1 and 2 for purposes of clarity, may be included in the reactor system to control the flow of feed, reactants, aqueous solvents and additives, organic solvents and additives, and product.

In operation, the reaction of the carbohydrate feed stock takes place in the aqueous phase, at elevated temperatures. The furan derivative products formed (exemplary structures of which are shown in FIGS. 1 and 2) are far more soluble in the organic phase than in the aqueous phase and thus are mostly extracted into the organic phase in each reactor circuit. The small amount of furan derivative compounds remaining in the aqueous phase is extracted by contacting the aqueous phase with fresh organic solvent. The aqueous phase and solvent are recycled back to the reaction vessels in a circuit, as shown by the oval symbols to the right of R1 and R2 of FIGS. 1 and 2. The organic fraction from each reaction circuit is then passed on to the next reactor in the system. Ultimately, the solvent is removed (thereby leaving a product mixture that comprises alkanes and which is suitable for use as a jet fuel). The evaporated organic solvent is recycled back into the organic portion of the reactor vessel.

Using the inventive method disclosed herein, HMF can be produced in high yields by the acid-catalyzed dehydration of fructose in a biphasic reactor using low boiling point solvents that themselves are excellent fuel components, thereby eliminating the need for expensive separation steps to produce the final liquid fuel mixture. The present method does not require using high boiling point solvents, such as DMSO or mixed solvents containing DMSO, which must be removed from the final product. The reactive aqueous phase in the biphasic reactor contains an acid catalyst and a sugar, and the extracting phase contains a partially miscible organic solvent (e.g., butanol) that continuously extracts the HMF product. Importantly, the addition of a salt to the aqueous phase improves the partitioning of HMF into the extracting phase and leads to increased HMF yields without the use of high boiling point solvents.

Still referring to FIGS. 1 and 2, in the aqueous phase within reactors R1, a carbohydrate feed (fructose is shown for illustrative purpose only) is dehydrated in the presence of an acid to yield HMF. Salt is preferably added to the aqueous phase to "salt-out" the resulting HMF into the extracting organic phase. The extracting phase within reactor R1 uses an organic solvent that has the following characteristics: (1) favors extraction of HMF from the aqueous phase; (2) is inert in the subsequent reactions of the product. An evaporator, shown to the right of R1 in FIGS. 1 and 2, removes and recycles a fraction of the organic solvent, trace levels of water, and the acid (HCl is shown for illustrative purposes only). Removal of the water yields to precipitation of small amounts of salt that are dissolved in the extracting phase. The precipitate is returned to the aqueous phase of the reactor R1.

Feedstock: The feedstocks for use in the present method can comprise any carbohydrate. Thus, for example, suitable feedstocks include hexoses (such as glucose, fructose, mannose, galactose, sorbose, etc.), pentoses (such as xylose, ribose, arabinose, etc.), as well as other mono-, di-, oligo-, and polysaccharides (such as sucrose, inulin, starch, etc.), and lignocellulosic material (such as cellulose, cellobiose, hemicellulose, xylan, etc.).

Aqueous Phase and Aqueous Phase Modifiers: The aqueous layer comprises water or a combination of water and one or more aqueous phase modifiers. The aqueous phase modifiers improve the selectivity and/or reactivity of the reaction toward furan derivatives. Preferably, the aqueous phase modifiers stay in the aqueous phase upon contact with the immiscible extracting layer (or are taken-up only in limited quantities into the extracting layer). The aqueous phase modifiers are generally selected from water-miscible inorganic salts selected from the group consisting of halides, sulfates, sulfides, phosphates, nitrates, acetates, carbonates, and ionic liquids (e.g., 1-butyl-3-methylimidazolium tetrafluoroborate); and/or dipolar, aprotic compounds such as such as sulfoxides (e.g., DMSO), amides (e.g., dimethylformamide), pyrrolidinones (e.g., NMP), nitriles (e.g., acetonitrile), pyrones, lactones (e.g., butyrolactone), water-miscible alcohols or ketones (methanol, ethanol, acetone) and dioxane, and water-soluble polymers such as PVP and PEG. The volume percentage of the aqueous modifier ranges from about 0.1 vol % to saturation for the salts, and from about 5 vol % to about 90 vol % for the aprotic additives so as to create a biphasic system with the organic phase.

Organic Phase and Organic Phase Modifiers: The preferred extractive organic phase for use in the present invention comprises an organic solvent that is immiscible with the chemically modified aqueous phase and (optionally) one or more organic phase modifiers. The preferred organic solvents are TBF, 1-butanol, MIBK, and dichloromethane (DCM). Other organic phases, especially other alcohols, ketones, and halogenated alkanes, may also be utilized. Thus, for example, organic solvents such as straight or branched alcohols (e.g. pentanol, tertbutyl alcohol, etc.), straight or branched alkanones (e.g. butanone (i.e., methylethyl ketone), pentanone, hexanone, heptanone, diisobutylketone, 3-methyl-2-butanone, 5-methyl-3-heptanone, etc.), and cycloalkanones (e.g., cyclobutanone, cyclopentanone, cyclohexanone, etc.) may be used in the present invention. Nitriles (such as benzonitrile), aliphatic and cycloaliphatic ethers (e.g., dichloroethylether, dimethyl ether), saturated and unsaturated aliphatic or aromatic hydrocarbons (decane, toluene, benzene), oxygenated hydrocarbons (e.g., THF, furan, etc.), and nitroalkanes (e.g., nitromethane, nitropropane, etc.) may also be used. Likewise, halogenated derivatives of the above-noted compounds, as well as other halogenated alkanes may also be used as the organic phase (e.g., chloromethane, trichloromethane, trichloroethane, and the like).

The organic phase modifiers are compounds that increase the extracting capability and/or selectivity toward furan derivative compounds. Because they are mostly immiscible in water (at least in the presence of a third component), they partition into the extracting layer and remain mostly in the extracting layer upon contact with the aqueous layer. Suitable organic phase modifiers are selected from the group consisting of $C_1$- to $C_8$-aliphatic alcohols, the most preferred being 2-butanol. The volume percentage of organic phase modifier ranges from about 5 to about 90% so as to create a biphasic system with aqueous phase.

Acid Catalysts: In the preferred embodiment using THF, butanol or MIBK as the extracting solvent, an acid catalyst should be used. The acid catalyst is preferably an inorganic acid, most preferably a mineral acid such as HCl, $HNO_3$, $H_2SO_4$, $H_3PO_4$, $H_3BO_3$, etc. Organic acids (e.g., oxalic acid, levulinic acid, citric acid, etc.), zeolites (Si/Al from 1 to 100), acid and super-acid resins (e.g., cation exchange resin), phosphates (NbOPO$_4$, vanadium phosphate), solid silica-, silica-alumina, and titania-based supports functionalized by acid groups, and other Lewis acids may also be used.

Illustrative Protocols: Experiments with different aqueous- and organic-phase modifiers demonstrate the utility and functionality of the inventive method (see Tables 1 and 2). Separate sets of experiments were carried out for different aqueous-phase modifiers (salt-based vs. aprotic-solvent-based) in order to independently demonstrate the utility of each type.

Experiments with the salt-based modifiers demonstrate that adding salt to the reactive aqueous phase increases the extracting ratio R (the ratio of the HMF concentration in the organic layer to that in the aqueous layer) by means of the salting-out effect. The salting-out effect is a phenomenon wherein electrolytes alter the intermolecular bonding interactions between liquid components, thereby decreasing the mutual solubility of the aqueous and organic phases. This results in an increased two-phase envelope. The capacity of the organic phase to extract HMF from the reactive aqueous phase, as measured by R, directly affects HMF selectivity. HMF selectivity increases as the value of R increases, irrespective of the extracting solvent utilized. Also, efficiently removing HMF from the aqueous phase prevents undesired side reactions arising from extended HMF residence in the reactive aqueous phase. Thus, the value of R for a specific extracting solvent depends not only on the affinity of the solvent for HMF, but also on the ability of the salt to increase the two-phase envelope of the specific system. For example, as compared to experiments without salt, a 30 wt % fructose solution saturated with NaCl (35 g of NaCl/100 g of H$_2$O) using 2-butanol as the extracting solvent (with initial ratio of organic and aqueous phase volumes $V_{org}/V_{aq}$=1.6) results in an increase in R from 1.6 to 3.3, leading to an improvement in HMF selectivity from 66% to 79% (Table 1, Runs 1 and 6). Notably, the presence of NaCl has the additional benefit of allowing higher values of $V_{org}/V_{aq}$ to be utilized, thus leading to higher HMF selectivities, while maintaining biphasic reaction conditions. Specifically, when the ratio $V_{org}/V_{aq}$ is doubled, the 2-butanol system without salt becomes monophasic, while the system saturated with NaCl remains biphasic, with an R of 3.6 and an HMF selectivity of 89% (Table 1, Run 5). The primary role of NaCl is to alter the solvent properties (i.e., to increase R and to widen the two-phase envelope) while otherwise remaining inert. In other words, the dehydration of fructose in the presence of NaCl, but in the absence of an extracting solvent, leads to the same HMF selectivity as in the absence of NaCl (see Table 1, Runs 19 and 20).

Experiments with aprotic, solvent-based modifiers demonstrate that these additives increase the reaction selectivity toward HMF. For 30 wt % fructose feeds, adding the aprotic solvent DMSO increases the HMF selectivity from 60% to 67% when MIBK is used as the extracting solvent. Other aprotic solvents, such as NMP, also have positive effects on HMF selectivity during the dehydration reaction. The dehydration of 10 wt % fructose in 7:3 Water:NMP using MIBK as the extracting solvent and an acidic ion-exchange resin catalyst generated 68% HMF selectivity at 80% conversion. Similarities in the properties of DMSO and NMP seem to indicate that NMP acts via similar mechanisms as DMSO to enhance HMF selectivity in the fructose dehydration reaction. However, while the carryover of DMSO from the aqueous phase into the organic phase is small (<0.8 wt % DMSO in MIBK after contacting an 8:2 water:DMSO aqueous solution as measured by HPLC), the carryover of NMP into the organic phase is considerably higher (~5 wt % NMP in MIBK after contacting a 7:3 water:NMP aqueous solution as measured by HPLC). The relatively large amount of NMP in the organic phase is a factor that must be taken into account in the subsequent separation of HMF from the organic phase by evaporation. Importantly, it was found that replacing NMP with PVP, a stable hydrophilic polymer that has NMP moieties along the polyethylene chain, preserves the benefits on selectivity produced by NMP, but eliminates organic phase contamination due to the low solubility of PVP in the extracting solvent. While aprotic, solvent-based additives increase the specificity of the reaction toward HMF, they also tend to decrease the R value. In short, on the one hand, they primarily increase the rate of fructose conversion into HMF. To some extent, aprotic, solvent-based additives also decrease the rates of undesirable parallel reactions occurring in the aqueous phase; on the other hand, unlike salt-based additives, aprotic, solvent-based additives increase the solubility of HMF in the aqueous phase. That is, these aprotic additives tend to lower the R value.

Adding 2-butanol to MIBK as an organic phase modifier helped counter this effect by improving the partitioning of the HMF product into the organic phase. Starting with a 30 wt % aqueous fructose solution and a $V_{org}/V_{aq}$=3.2, the optimal results using all modifiers (DMSO, PVP, and 2-butanol) yielded 0.065 g/ml of HMF in the organic layer, with 83% HMF selectivity at 82% conversion (see Table 2, run 3).

Increasing the extraction ratio R by using suitable modifiers in the aqueous and organic phases (e.g., metal salts and/or 2-butanol), and/or increasing $V_{org}/V_{aq}$, counteract the faster rate of HMF degradation in the presence of fructose. This undesirable reaction between fructose and HMF is reflected in lower HMF selectivities at 50 wt % fructose as compared to 30 wt % (see Table 2). It has been observed directly that lower selectivities are obtained when controlled amounts of HMF are added initially to the fructose reaction system. In addition, separating HMF from the aqueous medium lowers the rate of HMF rehydration into levulinic and formic acids. Analyses by GC-MS of the aqueous and organic phases after conversion of 30 wt % fructose showed that the general composition of the byproducts corresponds (typically) to 10% rehydration, 5% dehydration, 5% fragmentation, and 80% condensation compounds.

Simulations were performed for selected experiments from Table 1 to estimate the HMF concentrations that would be obtained by combining the batch reactor experiments described here with a counter-current extractor to remove the HMF remaining in the aqueous layer. The final amount of HMF obtained by combining the organic streams from the reactor and the extractor (i.e., the stream entering the evaporator) is used to calculate the energetic yield (Yη) as a measure of the overall efficiency of the present process for obtaining HMF by solvent evaporation. The energetic yield is the product of the HMF yield (Y), defined as the moles of HMF in the stream entering the evaporator divided by the total moles of fructose fed to the batch reactor, and an energy efficiency (η), defined as the heat of combustion of the HMF product ($\Delta H_{C,HMF}$) minus the energy necessary to evaporate the solvent ($\Delta H_{vap,org}$), normalized by the energy content of the product (i.e., $\eta=(\Delta H_{C,HMF}-\Delta H_{vap,org})/\Delta H_{C,HMF}$). To model a countercurrent extractor operating with equal volumes of aqueous and organic streams, the simulations used: (a) the experimental selectivity for each system (from Tables 1 and 2) (which were assumed to remain constant at 90% conversion); (b) the experimental value of $V_{org}/V_{aq}$ for the batch reactor; and (c) the experimental value of R. It is seen in Table 3 that aqueous and organic phase modifiers improve the value of Yη, thus reducing energy expenditures required to obtain the HMF product when compared to the water/MIBK system.

The value of Yη alone does not address the difficulties of using high-boiling organic systems. For example, although a theoretical value of Yη>75% can be obtained using pure DMSO, the HMF product cannot be separated from DMSO by simple evaporation. (Because of the reactive nature of concentrated HNF at high temperatures, distillation of HMF from DMSO leads to significant carbonization of the product.) Low temperature separation processes such as vacuum evaporation and vacuum distillation have been used to separate various solvents and byproducts from HMF mixtures, but no experimental data have been reported for DMSO.

Accordingly, in the present work, Aspen Plus simulation software (Version. 12.1, AspenTech, Inc.) was used to compare energy requirements for the separating HMF from a low-boiling solvent (pure MIBK) and from a high-boiling solvent (pure DMSO) for vacuum evaporation and vacuum distillation processes (for HWF levels of 0.1 w/w). Vacuum evaporation simulations predicted that 99.5% of the MIBK solvent can be evaporated at 13 mbar and 343 K with a 2.5% loss of HMF, whereas evaporating DMSO at 1.3 mbar and the same temperature resulted in a 30% loss of HMF (data not shown). Consequently, HMF separation from DMSO with minimal losses requires the more expensive vacuum distillation process (e.g., 0.66 mbar and a bottoms temperature of 386 K). When comparing both solvents using vacuum distillation, simulations predicted that an efficient separation of HMF from pure DMSO requires 40% more energy as compared to pure MIBK, clearly showing the advantages of using a low-boiling solvent system.

TABLE 1

Dehydration results for 30 wt % fructose solutions.

| Run | Salt % | Organic phase | Conversion (%) | Selectivity (%) | [HMF]aq (g/L) | [HMF]org (g/L) | R | [Salt]org (g/L) | [H$_2$O]org (wt %) |
|---|---|---|---|---|---|---|---|---|---|
| 1 | 0%[†] | 2-butanol | 58% | 66% | 28.6 | 46.0 | 1.6 | 0.0 | 31.4% |
| 2 | 5% | | 65% | 77% | 16.8 | 34.1 | 2.0 | 0.9 | 16.4% |
| 3 | 15% | | 65% | 85% | 12.7 | 34.4 | 2.7 | 1.1 | 9.6% |
| 4 | 25% | | 75% | 88% | 11.6 | 37.9 | 3.3 | 1.2 | 6.8% |
| 5 | 35% | | 74% | 89% | 10.6 | 38.1 | 3.6 | 1.6 | 6.5% |
| 6 | 35%[†] | | 71% | 79% | 18.0 | 60.0 | 3.3 | 1.6 | 7.4% |
| 7 | 0% | 1-butanol | 52% | 71% | 15.1 | 26.0 | 1.7 | 0.0 | 23.1% |
| 8 | 35% | | 85% | 82% | 13.2 | 39.2 | 3.0 | 1.6 | 6.1% |
| 9 | 35%[a] | | 80% | 83% | 12.0 | 39.0 | 3.3 | 1.6 | 6.1% |
| 10 | 35%[a] | | 88% | 82% | 12.9 | 43.1 | 3.3 | 1.6 | 6.1% |
| 11 | 35%[a] | | 77% | 84% | 12.4 | 37.8 | 3.0 | 1.6 | 6.1% |
| 12 | 35%[a] | | 64% | 84% | 10.2 | 32.4 | 3.2 | 1.6 | 6.1% |
| 13 | 0% | 1-hexanol | 50% | 64% | 21.1 | 18.4 | 0.9 | 0.0 | 7.9% |
| 14 | 35% | | 78% | 72% | 19.5 | 29.9 | 1.5 | 0.9 | 2.2% |
| 15 | 0% | MIBK | 50% | 71% | 20.0 | 21.8 | 1.1 | 0.0 | 0.9% |
| 16 | 35% | | 72% | 77% | 18.3 | 29.3 | 1.6 | 0.2 | 0.0% |
| 17 | 0% | 5:5 | 64% | 78% | 27.7 | 31.7 | 1.2 | 0 | 6.7% |
| 18 | 35% | Toluene:2-butanol | 74% | 88% | 13.8 | 37.4 | 2.7 | 0.8 | 1.9% |
| 19 | 0% | None | 44% | 55% | 53.5 | 0.0 | 0.0 | 0.0 | — |
| 20 | 35% | | 59% | 57% | 70.8 | 0.0 | 0.0 | 35.0 | — |
| 21 | 5%[††] | 2-butanol | 30% | 36% | 1.2 | 2.3 | 1.9 | 0.9 | 16.4% |
| 22 | 35%[††] | | 56% | 48% | 1.1 | 3.9 | 3.6 | 1.6 | 6.5% |

Fructose weight percent calculated on a salt-free basis.

Standard reaction conditions: T = 453 K and $V_{org}/V_{aq}$ = 3.2 with 0.25 M HCl catalyst (mol HCl/L of aqueous phase).

[a]Runs 9-12 used 0.12, 0.06, 0.03, and 0.01 M HCl, respectively. Error analysis of dehydration experiments based on the 1-butanol and 2-butanol systems saturated with NaCl showed standard deviations in selectivity of ±1.3% and ±1.5%, respectively (5 replicates).

Symbol [†] indicates runs that used $V_{org}/V_{aq}$ = 1.6.

Symbol [††] indicates a run that used a 10 wt % glucose (salt-free basis) feed.

Salt % is expressed as grams of salt divided by grams of water × 100.

TABLE 2

Results for acid-catalyzed dehydration of fructose.

| Run # | Aqueous Phase Composition | Organic Phase Composition | Conversion (%) | Selectivity (%) | $[HMF]_{aq}$ (g/ml) | $[HMF]_{org}$ (g/ml) | R | $V_{org}/V_{aq}$ |
|---|---|---|---|---|---|---|---|---|
| \multicolumn{9}{c}{30 wt % fructose with HCl catalyst} | | | | | | | | |
| 1 | Water | none | 50 | 51 | 0.060 | — | 0.00 | 0.00 |
| 2 | Water | MIBK | 91 | 60 | 0.056 | 0.050 | 0.90 | 1.51 |
| 3* | Water | MIBK | 75 | 73 | 0.035 | 0.033 | 0.96 | 3.13 |
| 4 | Water | 7:3 MIBK:2-butanol | 68 | 70 | 0.033 | 0.054 | 1.65 | 1.56 |
| 5* | Water | 7:3 MIBK:2-butanol | 86 | 80 | 0.026 | 0.045 | 1.73 | 3.68 |
| 6 | 8:2 Water:DMSO | MIBK | 94 | 67 | 0.077 | 0.050 | 0.66 | 1.41 |
| 7 | 8:2 Water:DMSO | 7:3 MIBK:2-butanol | 80 | 75 | 0.050 | 0.064 | 1.30 | 1.49 |
| 8* | 8:2 Water:DMSO | 7:3 MIBK:2-butanol | 87 | 82 | 0.034 | 0.046 | 1.39 | 3.65 |
| 9 | 7:3 Water:PVP | MIBK | 74 | 66 | 0.055 | 0.041 | 0.81 | 1.56 |
| 10 | 7:3 Water:PVP | 7:3 MIBK:2-butanol | 62 | 76 | 0.042 | 0.047 | 1.25 | 1.57 |
| 11* | 7:3 Water:PVP | 7:3 MIBK:2-butanol | 79 | 82 | 0.030 | 0.041 | 1.44 | 3.83 |
| 12 | 7:3(8:2 Water:DMSO):PVP | MIBK | 79 | 75 | 0.071 | 0.047 | 0.71 | 1.52 |
| 13 | 7:3(8:2 Water:DMSO):PVP | 7:3 MIBK:2-butanol | 82 | 83 | 0.063 | 0.065 | 1.12 | 1.62 |
| 14* | 7:3(8:2 Water:DMSO):PVP | 7:3 MIBK:2-butanol | 89 | 85 | 0.043 | 0.046 | 1.17 | 3.99 |
| \multicolumn{9}{c}{50 wt % fructose with HCl catalyst} | | | | | | | | |
| 15 | Water | none | 51 | 28 | 0.064 | — | 0.00 | 0.00 |
| 16 | Water | MIBK | 65 | 47 | 0.049 | 0.051 | 1.11 | 1.80 |
| 17 | Water | 7:3 MIBK:2-butanol | 71 | 59 | 0.049 | 0.079 | 1.73 | 1.91 |
| 18* | Water | 7:3 MIBK:2-butanol | 88 | 72 | 0.045 | 0.069 | 1.55 | 4.66 |
| 19 | 8:2 Water:DMSO | MIBK | 71 | 57 | 0.076 | 0.060 | 0.86 | 1.69 |
| 20 | 8:2 Water:DMSO | 7:3 MIBK:2-butanol | 80 | 63 | 0.077 | 0.085 | 1.19 | 1.87 |
| 21* | 8:2 Water:DMSO | 7:3 MIBK:2-butanol | 91 | 74 | 0.059 | 0.072 | 1.30 | 4.87 |
| 22 | 7:3 Water:PVP | MIBK | 85 | 56 | 0.074 | 0.060 | 0.80 | 1.72 |
| 23 | 7:3 Water:PVP | 7:3 MIBK:2-butanol | 77 | 61 | 0.076 | 0.081 | 1.19 | 1.85 |
| 24* | 7:3 Water:PVP | 7:3 MIBK:2-butanol | 90 | 77 | 0.062 | 0.070 | 1.22 | 5.15 |
| 25 | 7:3(8:2 Water:DMSO):PVP | MIBK | 77 | 61 | 0.095 | 0.066 | 0.77 | 1.85 |
| 26 | 7:3(8:2 Water:DMSO):PVP | 7:3 MIBK:2-butanol | 72 | 62 | 0.068 | 0.074 | 1.25 | 1.89 |
| 27* | 7:3(8:2 Water:DMSO):PVP | 7:3 MIBK:2-butanol | 92 | 77 | 0.076 | 0.070 | 1.03 | 5.11 |
| \multicolumn{9}{c}{10 wt % fructose with ion-exchange resin catalyst} | | | | | | | | |
| 28 | Water | MIBK | 75 | 44 | 0.010 | 0.011 | 1.02 | 1.32 |
| 29 | Water | MIBK | 17 | 43 | 0.002 | 0.002 | 1.15 | 1.29 |
| 30 | Water | 7:3 MIBK:2-butanol | 61 | 60 | 0.009 | 0.014 | 1.61 | 1.31 |
| 31 | 8:2 Water:DMSO | MIBK | 84 | 47 | 0.015 | 0.012 | 0.79 | 1.26 |
| 32 | 8:2 Water:DMSO | MIBK | 19 | 80 | 0.005 | 0.004 | 0.87 | 1.24 |
| 33 | 8:2 Water:DMSO | 7:3 MIBK:2-butanol | 74 | 68 | 0.015 | 0.017 | 1.18 | 1.24 |
| 34 | 7:3 Water:PVP | MIBK | 74 | 63 | 0.018 | 0.013 | 0.79 | 1.43 |
| 35 | 7:3 Water:PVP | 7:3 MIBK:2-butanol | 70 | 65 | 0.015 | 0.015 | 1.04 | 1.46 |
| 36 | 7:3(8:2 Water:DMSO):PVP | MIBK | 80 | 71 | 0.026 | 0.013 | 0.54 | 1.38 |
| 37 | 7:3(8:2 Water:DMSO):PVP | 7:3 MIBK:2-butanol | 76 | 77 | 0.020 | 0.019 | 1.03 | 1.43 |
| \multicolumn{9}{c}{30 wt % fructose with ion-exchange resin catalyst} | | | | | | | | |
| 38 | 7:3(8:2 Water:DMSO):PVP | MIBK | 89 | 60 | 0.066 | 0.041 | 0.66 | 1.65 |
| 39 | 7:3(8:2 Water:DMSO):PVP | 7:3 MIBK:2-butanol | 83 | 65 | 0.053 | 0.051 | 1.07 | 1.74 |
| \multicolumn{9}{c}{30 wt % fructose with $H_2SO_4$ catalyst} | | | | | | | | |
| 40* | Water | 7:3 MIBK:2-butanol | 80 | 66 | 0.022 | 0.035 | 1.63 | 3.54 |
| 41* | 8:2 Water:DMSO | 7:3 MIBK:2-butanol | 85 | 71 | 0.029 | 0.040 | 1.35 | 3.59 |
| \multicolumn{9}{c}{30 wt % fructose with $H_3PO_4$ catalyst} | | | | | | | | |

TABLE 2-continued

Results for acid-catalyzed dehydration of fructose.

| Run # | Aqueous Phase Composition | Organic Phase Composition | Conversion (%) | Selectivity (%) | $[HMF]_{aq}$ (g/ml) | $[HMF]_{org}$ (g/ml) | R | $V_{org}/V_{aq}$ |
|---|---|---|---|---|---|---|---|---|
| 42* | Water | 7:3 MIBK:2-butanol | 65 | 65 | 0.016 | 0.029 | 1.89 | 3.47 |
| 43* | 8:2 Water:DMSO | 7:3 MIBK:2-butanol | 51 | 76 | 0.016 | 0.025 | 1.58 | 2.95 |

Runs 1-27 were carried out at 453 K for 2.5-3 minutes using 0.25 M HCl aqueous phase solutions; runs 28-39 were carried out at 363 K for 8-16 hours using an acidic ion-exchange resin at a 1:1 w/w fructose:resin ratio.
Aqueous phase and organic phase compositions are reported as w/w ratios.
Conversion is defined as the ratio of fructose consumed to fructose added initially.
R = $[HMF]_{org}/[HMF]_{aq}$.
Standard runs for HCl, $H_2SO_4$ and $H_3PO_4$ catalysts used 1.5 g of aqueous phase and 1.5 g of extracting solvent.
Runs marked with * used 3 g of extracting solvent.
Runs for resin catalyst used 5.0 g of aqueous phase and 5.0 g of extracting solvent.
$V_{org}/V_{aq}$ measured upon completion of reaction.

TABLE 3

Simulation of HMF yield (Y) and energetic yield (Yη) for selected dehydration systems.

| Run* # | Aqueous Phase Composition | Organic Phase Composition | Selectivity† (%) | $[HMF]_{aq}$ (g/ml) | $[HMF]_{org}$ (g/ml) | Y‡ (%) | Yη (%) |
|---|---|---|---|---|---|---|---|
| | | 30 wt % fructose | | | | | |
| 2 | Water | MIBK | 60 | 0.007 | 0.045 | 48 | 34 |
| 4 | Water | 7:3 MIBK:2-butanol | 70 | 0.0001 | 0.057 | 61 | 43 |
| 6 | 8:2 Water:DMSO | MIBK | 67 | 0.025 | 0.048 | 48 | 35 |
| 7 | 8:2 Water:DMSO | 7:3 MIBK:2-butanol | 75 | 0.001 | 0.063 | 66 | 48 |
| 12 | 7:3(8:2 Water:DMSO):PVP | MIBK | 75 | 0.024 | 0.057 | 56 | 44 |
| 13 | 7:3(8:2 Water:DMSO):PVP | 7:3 MIBK:2-butanol | 83 | 0.003 | 0.071 | 73 | 56 |
| | | 50 wt % fructose | | | | | |
| 16 | Water | MIBK | 47 | 0.00260 | 0.05381 | 39 | 27 |
| 26 | 7:3(8:2 Water:DMSO):PVP | 7:3 MIBK:2-butanol | 62 | 0.00186 | 0.09079 | 53 | 43 |
| 27 | 7:3(8:2 Water:DMSO):PVP | 7:3 MIBK:2-butanol | 77 | 0.00552 | 0.07102 | 67 | 51 |

*Based on runs in Table 2.
†Selectivity set to the value obtained experimentally, and conversion assumed to be 90%.
‡Yield calculated based on HMF present in the organic stream sent to the evaporator.
$[HMF]_{aq}$ corresponds to the HMF concentration in the aqueous phase leaving the extractor, and $[HMF]_{org}$ corresponds to the HMF concentration entering the evaporator in FIG. 3.

In the present invention, the long-chain alkanes are formed by linking carbohydrate-derived moieties via new C—C bonds. In essence, the chain-length of the carbohydrate feed stocks (preferably derived from biomass) are increased to lengths suitable for long-chain alkanes. As discussed previously, the resulting long-chain β-hydroxy carbonyl compounds are then reacted further to reduce the carbonyl groups, either to yield useful feedstocks for making organic chemicals or to yield alkanes, ethers, and the like, suitable for combustion as transportation fuel, preferably jet fuel. The carbon-carbon bonds are created via one or more aldol condensation reactions in a monophasic or a biphasic reactor system, preferably using a mineral base catalyst (such as NaOH) or a solid base catalyst comprising a combination of magnesium, zirconium, and oxygen.

Thus, the present invention is directed to a catalytic process for converting carbohydrates in general, and biomass-derived carbohydrates in particular, to liquid, long-chain alkanes in the higher mass ranges (i.e., from $C_8$ to $C_{15}$) that can be used as sulfur-free fuel components. The C—O—C linkages (as found in disaccharides) are broken by acid or enzymatic hydrolysis to form monocarbohydrates. New carbon-carbon bonds are then formed between carbohydrate-derived moieties via a dehydration step (preferably acid catalyzed) coupled with one or more aldol condensation (base catalyzed) steps.

The solid base catalysts used in the aldol reactions, as well as the hydrogenation reactions, are stable, mixed-oxide base catalysts. The preferred solid base catalyst comprises a combination of magnesium, zirconium, and oxygen. Other catalysts, including mixtures of catalysts can be used, including, without limitation: Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O or combinations thereof. If an impregnated catalyst is desired or expedient, various supports, may be used, including, without limitation: $ZrO_2$, $TiO_2$, carbon, carbon nanotubes, nanoporous support, ceria, SiO-AlO, silica nitride, boron nitride, trimethylethoxysilane on $SiO_2$, or mixtures of thereof.

Different atomic ratios of Mg/Zr or the combinations of various other elements constituting the mixed oxide catalyst may be used ranging from about 0.01 to about 50. In case of hydrogenation reactions, metals or alloys of Pd, Pt, Ni, Fe, Cu, Ru, Co, Ir, Rh, with promoters such as Au, Ag, Cr, Zn, Mn, Sn, Bi, Pb may be used in various loadings ranging from about 0.01 to about 20 wt %. The catalysts may be used neat or impregnated on/in a support. The catalysts are preferably made by the sol-gel technique, which allows for control of pH, ageing time, temperature, and drying. Catalysts are preferably calcined at a temperature of from about 200 to about 700° C.

Different water-soluble mineral bases can also be used for aldol condensation. The preferred catalysts comprise the hydroxides of alkali metals and alkaline earth metals such as sodium hydroxide (NaOH) and potassium hydroxide (KOH). Other possibilities include salts of carbanions, amides, phosphates, carbonates, and hydrides, among others.

The aldol reactions described herein in monophasic or biphasic reactor systems may be carried out in any reactor of suitable design, including continuous, batch, and semi-batch reactors, as well as continuous flow reactors, without limitation as to design, size, geometry, flow rates, etc. (e.g., plug-flow reactors, continuous stirred-tank reactors, and the like). Preferred reaction parameters are given below and in the Examples. Generally, reaction pressures run from atmospheric to about 100 atm, with temperatures ranging roughly from about 0° C. to about 300° C.

The biphasic solvent systems described previously are the preferred solvent combinations. The aqueous phase may comprise miscible two-part solvent systems comprising water and another water-miscible solvent (such as dimethylformamide, dimethylsulfoxide, 1-methyl-2 pyrrolidinone (NMP), polyvinylpyrrolidone, acetonitrile, polyethylene glycerol, butyl acetate, methanol, acetone, ethanol, etc.). In the biphasic solvent system, water is the first solvent, and the second solvent is immiscible in water, such as $CH_2Cl_2$, methyl-isobutyl ketone, toluene, benzene, furan, benzonitrile, etc. Similarly, a three-component, two-phase system comprised of water/solvent 2/solvent 3 may also be used. In this solvent system, both solvent 2 and solvent 3 are immiscible in the water.

In the preferred embodiment, the hydrodeoxygenation reactions are carried out in a four-phase reactor system. The reactor system comprises: (i) an aqueous inlet stream containing the large water-soluble organic reactant; a long-chain alkane (e.g., hexadecane) inlet stream (iii) a hydrogen inlet gas stream; and (iv) a solid catalyst ($Pt/SiO_2$—$Al_2O_3$) disposed within a furnace. The reactor also includes a heat exchanger, a liquid drain, and a gas-liquid separator. The product gas is removed from the gas-liquid separator at an outlet. The organic phase and the aqueous phase separate spontaneously within the gas-liquid separator. As dehydration/hydrogenation takes place, the aqueous organic reactant becomes more hydrophobic, and the long-chain alkane stream (e.g., hexadecane) removes hydrophobic species from the catalyst before they go on further to form coke.

Reaction kinetics experiments conducted with pure water as the aqueous feed showed that only a small amount of hexadecane was converted to lighter alkanes in the four-phase dehydration/hydrogenation reactor (four-phase D/H reactor) (0.007 $\mu mol\ min^{-1}\ g_{cat}^{-1}$). (In the Examples that follow, this low reactivity was subtracted from all of subsequent experimental data.)

To benchmark the performance of the four-phase D/H reactor, a test reaction was utilized: a 5 wt % aqueous solution of sorbitol was converted at differing feed rates of the hexadecane alkane stream. Results for these measurements showed that increasing the hexadecane flow rate decreased the conversion of sorbitol. Importantly, no major differences were observed in the selectivity of the reaction when the hexadecane-to-water flow rate ratio was increased.

By way of an initial experiment, furoin, furfural-acetone (1:1), and furfural-acetone (2:1) were hydrogenated in methanol in a stainless steel batch reactor (Parr Instrument Company, Moline, Ill.) at 55 bar $H_2$ pressure and 393 K, in the presence of a $Pd/Al_2O_3$ catalyst. The furoin was purchased from Aldrich Chemical, Milwaukee, Wis., and prepared from furfural by the Pinnacol coupling reaction, Zhang & Li (1998) *J. Chem. Soc., Perkin Trans.* 1:3131. The furfural acetone (1:1) was purchased from Aldrich and prepared by aldol condensation of furfural and acetone. The furfural-acetone (2:1) was prepared by aldol condensation of furfural-acetone with furfural and NaOH.) This hydrogenation step was carried out to minimize possible coking reactions that may take place from unsaturated molecules on the $Pt/SiO_2$—$Al_2O_3$ catalyst in the four-phase D/H reactor, and to increase the solubility of the condensed products in water.

The hydrogenated compounds were then dissolved in water and converted to alkanes in the four-phase D/H reactor. The main products of the hydrogenated furoin were n-$C_9$ and $C_{10}$ alkanes.

The hydrogenated furfural-acetone (1:1) was added to both water and hexadecane, and both feeds produced mainly n-$C_7$ and $C_8$ alkanes in the four-phase D/H process (see Table 4, entries 2 and 3). Hydrogenated furfural-acetone (2:1) produced primarily n-$C_{11}$ to $C_{13}$ alkanes from the four-phase D/H reactor.

Furfural-acetone (1:1) could also be hydrogenated in water without using methanol as a solvent (Tables 4 and 5, entry 4). In this step, the furfural-acetone (1:1) adduct, $Pd/Al_2O_3$ and water were introduced into a Parr reactor, which was subsequently pressurized with $H_2$ (55 bar) and heated to 393 K. As shown in entry 4 of Tables 4 and 5, this reaction yielded an aqueous solution of 12.5 wt % hydrogenated furfural-acetone (1:1), and this feed produced primarily n-$C_7$ and $C_8$ alkanes in the four-phase D/H reactor. The results from these experiments indicate that the present invention for producing liquid alkanes from biomass-derived resources does not require the use of alcohol solvents, and it is not limited to dilute aqueous feeds. (Note that whereas the solubility of furfural-acetone (1:1) is relatively low in water, hydrogenation of the furan ring in the adduct increases the solubility in water to levels higher than 35 wt %.)

Aldol condensation reactions are particularly relevant for producing large organic compounds from biomass because various carbonyl compounds can be formed from carbohydrates, including furfurals, dihydroxyacetone, and acetone. For example, glucose and xylose do not undergo aldol condensation reactions because the carbonyl group undergoes intramolecular reactions to form ring structures. See Collins & Ferrier, "Monosaccharides," Wiley, West Sussex, England, © 1995, and Gutsche et al. (1967), *J. Amer. Chem. Soc.* 89:1235. But dehydrating glucose and xylose (using mineral or solid acid catalysts) yields 5-hydroxymethylfurfural (HMF) and furfural, respectively. See Moreau, Durand, Peyron, Duhamet & Rivalier (1998) *Ind Crop. Prod.* 7:95; Moreau et al. (1996) *Appl. Catal. A* 145:211; Lourvanij & Rorrer (1993) *Ind. Eng Chem. Res.* 32:11; and J. Lewkowski (2001) *ARKIVOC* 2001, vol. 17.

Both HMF and furfural have an aldehyde group, and while they cannot undergo self condensation (because they do not have an alpha-position hydrogen atom) they can condense with other molecules that can form carbanion species, such as acetone, dihydroxyacetone or glyceraldehyde. Acetone can be produced from the fermentation of glucose (see Klass, supra), and dihydroxyacetone and glyceraldehyde can be produced from the retro-aldol condensation of glucose. See Kabyemela et al. (1999) *Ind. Eng. Chem. Res.* 38:2888. In the present invention, dehydration, hydrogenation, and aldol condensation reactions are linked to yield long-chain alkanes. See Reaction Schemes 5 and 6:

Reaction Scheme 5

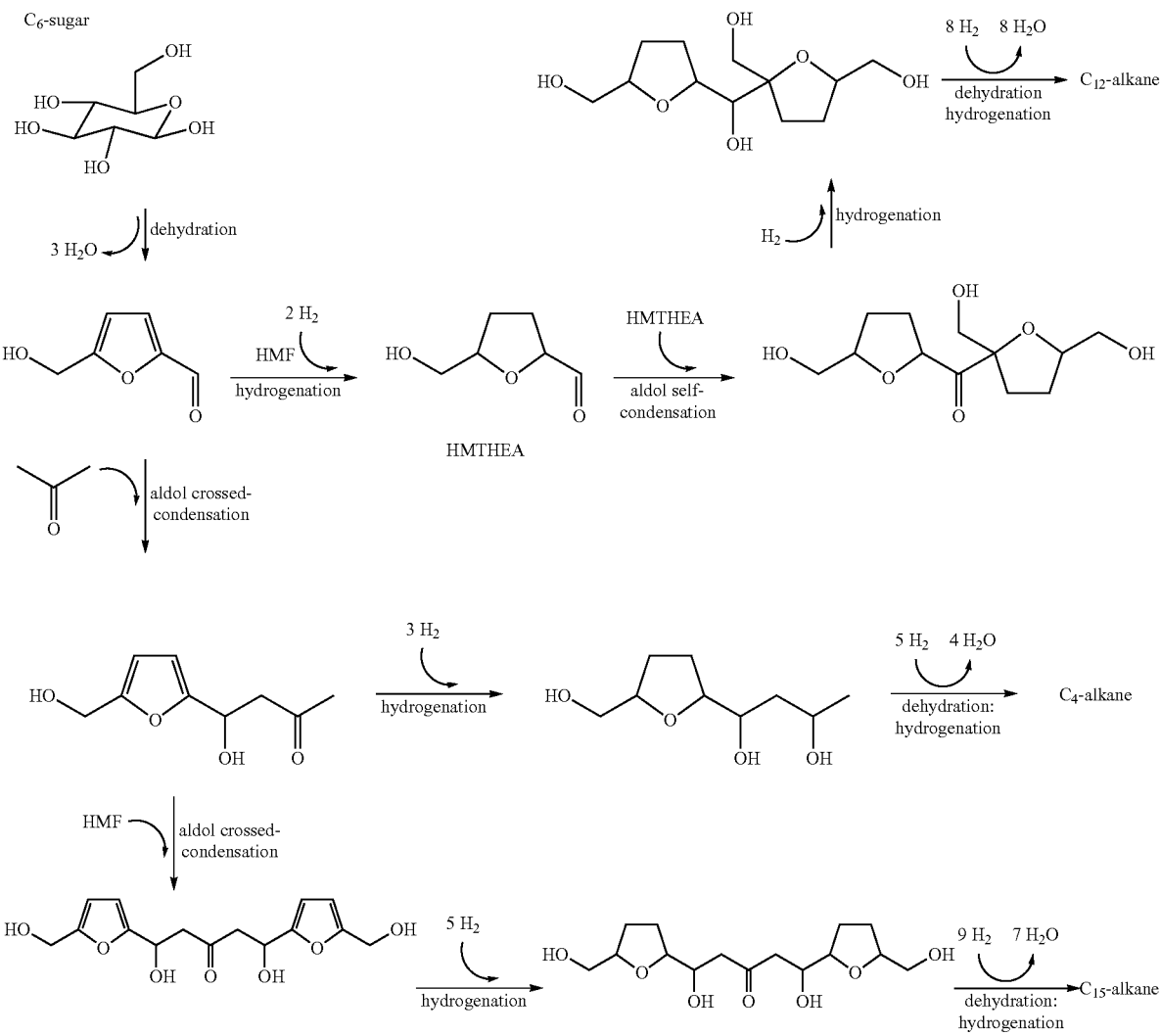

Crossed aldol condensation of HMF with acetone was carried out with HMF:acetone molar ratios of 1:1 and 1:10 using a mixed Mg—Al-oxide catalyst at room temperature (see Tables 4 and 5, entries 6 to 9). The Mg—Al-oxide catalyst was prepared by co-precipitation, similar to the method reported elsewhere. Sasaki, Goto, Tajima, Adschiri & Arai (2002) *Green Chem.* 4:285. Climent, Corma, Iborra, Epping, & Velty (2004) *J. Catal.* 225:316.

The condensed molecules were then hydrogenated in a batch reactor in a methanol/$H_2O$ solvent for the HMF:acetone (1:1)-1 and (1:1)-2 feeds, followed by conversion to alkanes in the four-phase D/H reactor. All other feeds described herein were batch-hydrogenated in $H_2O$. The condensed HMF:acetone feeds produced mainly $C_8$ to $C_{15}$ alkanes in the four-phase D/H reactor, depending on the HMF:acetone ratio used in the aldol condensation step. When the HMF:acetone ratio decreases, the alkane distribution shifts to lighter alkanes. The selectivity can also be shifted to heavier alkanes by increasing the extent of conversion for the aldol condensation step of HMF:acetone (see Table 5, entries 6 and 7).

Reaction Scheme 6

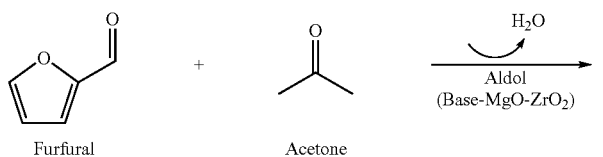

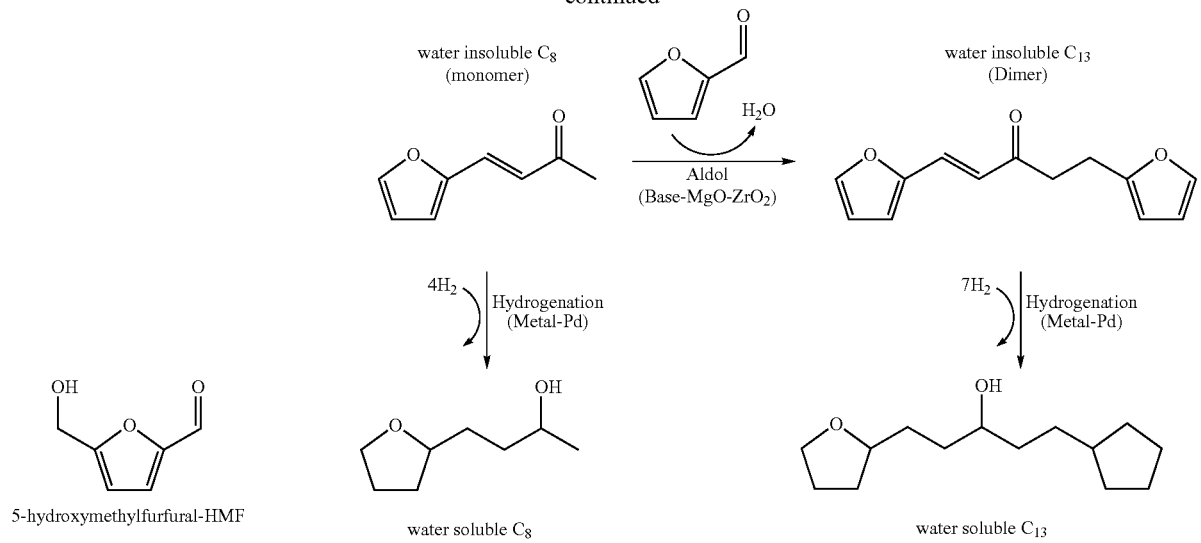

Reaction Scheme 6 shows the corresponding set of reactions wherein furfural and acetone are the reactants for the initial aldol condensation reaction (rather than hydroxymethylfurfural or hydroxymethyltetrahydrofurfural, as shown in Reaction Scheme 5).

TABLE 4

Values for conversion and process conditions for four-phase dehydration/hydrogenation (D/H) of biomass-derived molecules. (See the Examples for full experimental details.)

| | | Wt | WHSV | | % Carbon in Phase | | |
|---|---|---|---|---|---|---|---|
| Entry | Feed | (%) | (h$^{-1}$) | Org/Aq | Org | Gas | Aq |
| 1 | Furoin | 2.0 | 0.26 | 3.0 | 69.2 | 18.5 | 2.3 |
| 2 | Fur:Ace (1:1)-1 | 1.9 | 0.26 | 3.0 | 100.0 | 6.3 | 1.6 |
| 3 | Fur:Ace (1:1) org* | 5.0 | 0.51 | ∞ | 73.2 | 7.8 | NA |
| 4 | Fur:Ace (1:1)-3 | 12.5 | 0.29 | 3.0 | 91.2 | 4.1 | 0.7 |
| 5 | Fur:Ace (2:1) | 1.0 | 0.29 | 3.0 | 79.0 | 2.4 | 0.8 |
| 6 | HMF:Ace (1:1)-1 | 1.8 | 0.25 | 3.0 | 66.1 | 15.7 | 1.5 |
| 7 | HMF:Ace (1:1)-2† | 1.9 | 0.26 | 3.0 | 69.5 | 7.7 | 0.9 |
| 8 | HMF:Ace (1:1)-3 | 1.8 | 0.29 | 3.0 | 53.3 | 31.1 | 2.3 |
| 9 | HMF:Ace (1:10) | 9.5 | 0.35 | 0.7 | 77.2 | 10.3 | 20.0 |
| 10 | HMF:Fur:Ace (1:1:2) | 1.9 | 0.29 | 3.0 | 48.5 | 27.8 | 3.1 |
| 11 | SC THF3A | 5.0 | 0.35 | 0.7 | 53.2 | 44.1 | 4.2 |
| 12 | SC THF2A | 3.9 | 0.35 | 0.7 | 47.9 | 20.8 | 13.0 |

*Fur:Ace (1:1) org was added to the hexadecane feed and no aqueous flow was used for this feed.
†This feed was condensed with twice the amount of Mg—Al-oxide than the feed above it (Entry 6).
All four-phase D/H reactions were carried out at 523 to 538 K, 52 to 60 bar and $H_2$ gas hourly space velocity (v/v) of 1000 to 3000 h$^{-1}$. A 4 wt % Pt/$SiO_2$—$Al_2O_3$ catalyst was used for these reactions. Each experimental point was collected after 20 h time-on-stream. Condensed feeds were prepared by aldol condensation at room temperature using Mg—Al-oxide and NaOH catalysts.
Feed key:
SC = self condensed;
Fur = furfural;
Ace = acetone;
HMF = 5-hydroxymethylfurfural;
THF3A = tetrahydrofuran-3 carboxyaldehyde;
THF2A = tetrahydrofuran-2 carboxyaldehyde.
Numbers listed in parentheses indicate molar ratio of feeds.
All feeds were hydrogenated in a Parr reactor with a Pd/$Al_2O_3$ catalyst prior to conversion in the four-phase D/H reactor.
Entries 1 to 3 and 5 to 7 were hydrogenated in methanol or a methanol/water mixture, with all other feeds being hydrogenated in $H_2O$.
Abbreviations:
Wt (%) refers to weight percent organics in aqueous feed solution.
WHSV is weight hourly space velocity; mass of aqueous feed solution per mass of catalyst per hour.
Org/Aq is the organic (hexadecane)-to-aqueous volumetric feed ratio.

TABLE 5

Selected values for alkane and CO2 selectivities from four-phase dehydration/hydrogenation of biomass derived-molecules. (See the Examples for complete experimental details.)

| | | Alkane and $CO_2$ Selectivities (%) | | | | | | | | | | | | | | |
|---|---|---|---|---|---|---|---|---|---|---|---|---|---|---|---|---|
| Entry | Feed | $CO_2$ | $C_1$ | $C_2$ | $C_3$ | $C_4$ | $C_5$ | $C_6$ | $C_7$ | $C_8$ | $C_9$ | $C_{10}$ | $C_{11}$ | $C_{12}$ | $C_{13}$ | $C_{14}$ | $C_{15}$ |
| 1 | Furoin | 5.2 | 5.2 | 0.0 | 2.8 | 8.0 | 9.2 | 1.8 | 0.3 | 5.4 | 26.2 | 34.0 | 0.7 | 0.3 | 0.3 | 0.4 | 0.2 |
| 2 | Fur:Ace (1:1)-1 | 1.8 | 2.2 | 0.0 | 0.0 | 0.1 | 0.2 | 0.3 | 15.0 | 77.7 | 0.6 | 0.2 | 0.4 | 0.3 | 0.4 | 0.4 | 0.4 |
| 3 | Fur:Ace (1:1) org | 0.0 | 4.7 | 0.2 | 1.7 | 1.8 | 2.0 | 1.9 | 4.5 | 71.4 | 2.4 | 2.2 | 2.2 | 2.1 | 2.4 | 0.6 | 0.0 |
| 4 | Fur:Ace (1:1)-3 | 1.7 | 0.4 | 0.0 | 0.1 | 0.1 | 0.1 | 0.2 | 17.1 | 64.4 | 7.4 | 5.8 | 2.5 | 0.1 | 0.1 | 0.1 | 0.0 |

TABLE 5-continued

Selected values for alkane and CO2 selectivities from four-phase
dehydration/hydrogenation of biomass derived-molecules. (See the Examples for
complete experimental details.)

| | | Alkane and $CO_2$ Selectivities (%) | | | | | | | | | | | | | | |
|---|---|---|---|---|---|---|---|---|---|---|---|---|---|---|---|---|
| Entry | Feed | $CO_2$ | $C_1$ | $C_2$ | $C_3$ | $C_4$ | $C_5$ | $C_6$ | $C_7$ | $C_8$ | $C_9$ | $C_{10}$ | $C_{11}$ | $C_{12}$ | $C_{13}$ | $C_{14}$ | $C_{15}$ |
| 5 | Fur:Ace (2:1) | 0.0 | 3.0 | 0.0 | 0.0 | 0.0 | 0.4 | 0.7 | 1.0 | 2.1 | 0.8 | 0.5 | 2.1 | 19.7 | 68.6 | 0.6 | 0.5 |
| 6 | HMF:Ace (1:1)-1* | 6.8 | 3.3 | 0.0 | 0.0 | 6.0 | 14.6 | 9.3 | 0.4 | 6.8 | 9.5 | 0.0 | 0.0 | 0.7 | 8.5 | 19.5 | 14.5 |
| 7 | HMF:Ace (1:1)-2* | 5.0 | 4.0 | 0.0 | 0.0 | 1.5 | 3.2 | 2.2 | 0.4 | 2.9 | 4.6 | 0.2 | 0.4 | 1.5 | 13.5 | 32.9 | 27.6 |
| 8 | HMF:Ace (1:1)-3 | 5.7 | 3.5 | 0.0 | 23.5 | 3.8 | 10.0 | 7.0 | 0.7 | 5.9 | 6.9 | 0.1 | 0.3 | 1.0 | 6.2 | 14.5 | 10.9 |
| 9 | HMF:Ace (1:10)† | 6.0 | 0.9 | 0.0 | 0.0 | 2.6 | 4.8 | 1.1 | 3.9 | 27.4 | 41.2 | 1.9 | 0.2 | 0.5 | 5.1 | 3.6 | 0.8 |
| 10 | HMF:Fur:Ace (1:1:2) | 4.0 | 3.0 | 0.0 | 25.3 | 3.8 | 7.2 | 3.3 | 2.5 | 10.2 | 5.6 | 0.0 | 1.0 | 4.8 | 14.3 | 10.8 | 4.4 |
| 11 | SC THF3A‡ | 9.4 | 0.7 | 0.0 | 4.2 | 23.4 | 25.1 | 0.1 | 3.4 | 6.7 | 11.6 | 14.3 | 0.1 | 0.9 | 0.0 | 0.0 | 0.0 |
| 12 | SC THF2A§ | 11.4 | 1.3 | 0.0 | 5.1 | 15.1 | 9.9 | 0.5 | 5.2 | 13.0 | 17.7 | 19.4 | 0.3 | 0.9 | 0.3 | 0.0 | 0.0 |

*$C_3$ selectivity is zero because acetone was removed during separation of hydrogenated products from methanol-water solution.
†Propane is not included in the alkane selectivity calculation for this feed.
‡Liquid alkanes produced in this feed were mostly branched. The $C_{10}$ alkane was 3-methyl-5-dimethyl-heptane.
§Liquid alkanes produced in this feed were mostly branched. The $C_{10}$ alkane was 4-methylnonane.
Table 4 contains relevant process conditions, feed key and conversion data.
Selectivity = (moles product × number of carbon atoms in product)/(total moles of carbon atoms in products) × 100. The selectivity only takes into account the products in the organic and gas phases.
Alkane products are mostly straight chain, except for the SC THF3A and SC THF2A feeds. At lower conversions small amounts of alcohols (<10% of total products) are also observed in the organic phase.

To improve the potential practical utility of the invention, it was determined whether hydrogenation of the HMF:acetone adduct could be accomplished without using methanol as a solvent. In this instance, the aldol condensation of HMF:acetone (1:1) was carried out in water over the Mg—Al-oxide catalyst, and $Pd/Al_2O_3$ was added to the reaction slurry, followed by treatment with $H_2$ (55 bar) at 393 K in the Parr reactor. Similar to hydrogenation of furfural:acetone in water, it was discovered that hydrogenation of the HMF:acetone adduct increases its solubility in water, and the aqueous solution from this hydrogenation step produced significant amounts of $C_{14}$ and $C_{15}$ alkanes from the four-phase D/H reactor (Table 5, entry 8).

The results shown in Tables 4 and 5 also show that mixtures of HMF and furfural (Tables 4 and 5, entry 10) can be condensed with acetone to form alkanes ranging from $C_7$ to $C_{15}$. Unlike producing ethanol by fermentation, in the present invention cellulose and hemicellulose need not be separated to produce liquid alkanes by four-phase D/H processing.

Results for crossed aldol condensation of furfural and HMF with dihydroxyacetone and glyceraldehyde are summarized in entries S15 to S20 of Tables 14 and 15 (see the Examples). These condensation reactions over Mg—Al-oxide catalyst showed a large disappearance of furfural and HMF based on high-performance liquid chromatography ("HPLC") (Table 10); however, as shown in Table 13 less than 30% of the alkane products are heavier than the $C_5$ and $C_6$ reactants (for reactions of furfural and HMF, respectively). Condensing furfural with hydroxyacetone gave an alkane distribution similar to that produced from condensation of furfural with dihydroxyacetone (see Table 13, entry S18). Thus, making heavier liquid alkanes by crossed aldol condensation of furfural and HMF with dihydroxyacetone, hydroxyacetone, or glyceraldehydes is clearly within the scope of the present invention.

Another route to make large water-soluble organic compounds is to hydrogenate the C=C bonds of HMF and furfural selectively, thereby producing 5-hydroxymethyl-tetrahydrofurfural (HMTHFA) and tetrahydrofuran-2 carboxyaldehyde (THF2A), respectively. These species can form carbanion species and undergo self aldol condensation reactions (see Reaction Scheme 5). The results show that self aldol condensation of tetrahydrofuran-3 carboxyaldehyde and THF2A produced liquid hydrocarbons ranging from $C_8$-$C_{10}$ from the four-phase D/H reactor. THF2A was produced by dehydrogenation of tetrahydrofurfuryl alcohol in the gas phase over a $Cu/SiO_2$ catalyst.

Of particular note is that the conversion of carbohydrates to liquid alkanes involves the storage of a considerable amount of hydrogen in the fuel. In short, essentially one (1) molecule of $H_2$ is used to convert each carbon atom in the carbohydrate reactant to an alkane moiety. The liquid alkanes retain about 90% of the energy content of the carbohydrate and $H_2$ reactants. Thus, the carbon in the carbohydrates serves as an effective energy carrier for transportation vehicles, analogous to the role of carbohydrates as energy storage compounds for living organisms.

The experiments presented to this point demonstrate that liquid alkanes can be produced from biomass-derived compounds, without an expensive distillation step. However, the catalysts used in the initial work were not as robust as desired. Thus, investigations were undertaken to find an effective, robust, and recyclable solid base catalyst that exhibits long-term stability under the aqueous-phase reaction conditions used. After much work, it was found that a catalyst comprised of magnesium, zirconium, and oxygen was the preferred catalyst for use in the present invention.

The preferred solid base catalyst was prepared and characterized as described in the Examples. The preferred atomic ratio of Mg/Zr is about 11.6, although it can vary in the range from about 0.5 to about 50.

The preferred MgZrO catalyst is remarkably stable. Experiments were conducted comparing HMF disappearance versus time during an aldol condensation with acetone over a fresh, calcined, recycled mixed Mg—Al-oxide catalyst and the preferred MgO—$ZrO_2$ catalyst. The mixed Mg—Al-oxide runs were carried out at room temperature and pressure, while MgO—$ZrO_2$ runs were carried out at 323 K and atmospheric pressure. HMF:acetone molar ratio was equal to 1:10, with 11.2 wt % organics in the aqueous phase, and an organic/catalyst mass ratio equal to 6. While the mixed Mg—Al-oxide catalyst displayed highly desirable results in the first run, it displayed markedly diminished catalytic activity in each of runs 2 and 3, respectively. In contrast, the preferred MgO—ZrO$_2$ catalyst displayed consistently high (and essentially unchanged) catalytic activity through all three runs. (Data not shown.)

Adding a noble metal, such as palladium, to the MgZrO catalyst also has a marked impact on the extent of hydrogenation. Here, furfural and acetone were subjected to an aldol condensation followed by hydrogenation over a Pd/MgZrO catalyst. The data (not shown) clearly demonstrates that the extent of reaction can be beneficially controlled by modifying the loading of the catalyst.

Likewise, the preferred MgZrO catalyst can be regenerated via calcination. To test the regeneration capacity of the MgZrO catalyst, a furfural/acetone condensation/hydrogenation reaction was performed, as described earlier. The reaction was run three times in succession, without any calcination of the catalyst. The relative proportion of C$_5$ alkanes steadily increased from run 1 to run 3. At the same time, the relative proportion of the desired long-chain C$_8$ and C$_{13}$ alkanes gradually decreased from run 1 to run 3. After run 3, the catalyst was calcined, and the reaction was repeated a fourth time. In the fourth run, the catalytic activity returns essentially to the same point as in the first run. In short, the preferred catalyst for the aldol condensation reactions can be recycled, thereby making the process more economically feasible.

As in the reactions described previously, the product mixture using the MgZrO catalyst can be altered by judiciously controlling the feed stock ratios. A cross-condensation reaction of HMF and acetone at various concentrations was conducted, under the same conditions as described previously, with the exception that the MgZrO catalyst was used. Using a feedstock of 1:10, HMF:acetone, C$_8$ and C$_9$ alkanes dominate the product mix. Using a feedstock of 1:1, HMF:acetone, C$_{13}$ to C$_{15}$ alkanes dominate the product mix.

Similar results are shown when a 12.5 wt % solution of furfural and acetone is used as the feedstock. Using a feedstock of 1:1, furfural:acetone, C$_7$ and C$_8$ alkanes dominate the product mix. Using a feedstock of 2:1, furfural:acetone, C$_{12}$ and C$_{13}$ alkanes dominate the product mix. Of very considerable note is that a mixture of HMF and acetone can be condensed to yield C$_7$ to C$_{15}$ alkanes, indicating that separating cellulose from hemicellulose is not required in the present invention.

Based on these results, an overall organic feed concentration of up to about 50 wt % can be processed according to the present invention. Where cross-condensation reactions are performed, the molar ratio of the cross-condensing species preferably ranges from about 0.001 to about 30.

Self-condensation of tetrahydrofurfural (under the same conditions noted above) yielded a 55% percent selectivity for producing C$_7$ to C10 alkanes.

EXAMPLES

The following Examples are included solely to afford a more complete understanding of the process disclosed and claimed herein. The Examples do not limit the scope of the invention in any fashion.

The following series of Examples were performed to identify key processing variables for HMF and furfural production using the modified biphasic system described hereinabove. The overarching goal of the Examples was to improve the selectivity of the reaction when using less-reactive molecules as reactants, such as glucose, xylose, sucrose (a disaccharide of glucose and fructose), inulin (a polyfructan), starch (a polyglucan with α-1,4 glycoside linkages), cellobiose (a glucose dimer with β-1,4 glycoside linkages) and xylan (a polysaccharide with xylose monomer unit). These reactants are desirable because they are inexpensive and abundantly available. By directly processing these highly functionalized polysaccharides, the need to obtain simple carbohydrate molecules by acid hydrolysis as a separate processing step is eliminated. In short, the reaction can proceed directly, in the absence of an initial hydrolysis reaction of the raw carbohydrate feedstock.

Standard Operating Procedures for Examples 1-8:

Aqueous- and organic-phase components including carbohydrates (fructose, glucose, sucrose, etc.) DMSO, PVP (average M.W. 10,000), MIBK, butanol, NaCl, Na$_2$SO$_4$, HCl, H$_2$SO$_4$ and H$_3$PO$_4$ were obtained from Sigma-Aldrich Corp (St. Louis, Mo.). These reagents are also available from a large number of other national and international commercial suppliers. The ion-exchange resin, PK-216, was obtained from Mitsubishi Chemicals and was activated by mixing it with 5 bed volumes of 2 M HCl for 30 min, followed by extensive washing with de-ionized (DI) water and subsequent drying for 10 h at 343 K.

Batch catalytic experiments were carried out in 10 ml (Alltech), thick-walled glass reactors heated in a temperature controlled oil bath placed on top of a magnetic stirrer. The temperature in the oil bath was measured by a K-type thermocouple (Omega Engineering, Inc., Stamford, Conn.) and controlled using a series 16A temperature controller (Dwyer Instruments, Michigan City, Ind.) coupled with a 150 W heating cartridge (McMaster-Carr, Atlanta, Ga.). In a typical high-temperature experiment, 1.5 g of 0.25 M HCl aqueous phase solution and 1.5 g of organic phase solution were poured into the reactor (Runs 40-41 and 42-43 in Table 1 (above) used 0.5 M H$_2$SO$_4$ and 0.75 M H$_3$PO$_4$, respectively). The reaction was carried out in an oil bath set at reaction temperature and for the reaction times as indicated in Table 1 and 3. The reaction was stopped by rapidly cooling the reactor in an ethylene glycol bath set at 253 K. In a typical low-temperature experiment, 5 g of aqueous phase solution, 5 g of organic phase solution and ion exchange resin in a 1:1 w/w fructose:resin ratio were poured into a 25 ml glass reactor (Alltech). The reactor was then placed in an oil bath set at 353 K for 8-16 h to obtain fructose conversions close to 75%. In a typical run carried out with DCM, 7 g of aqueous phase solution and 7 g of DCM were filled in 23 ml Parr reactors with no catalyst added. Runs were carried out for 1-12 h of reaction times as indicated in Table 3.

After reaction, the reactors were cooled and the aqueous and organic phases were sampled and analyzed using HPLC. Sample analyses were performed by HPLC using a Waters 2690 system equipped with PDA 960 UV (320 nm) and RI—410 refractive index detectors. Fructose disappearance was monitored with an Aminex-brand HPX-87H column (Biorad, Hercules, Calif.), using MilliQ water (pH=2) as the mobile phase at a flow rate of 0.6 ml/min and a column temperature of 303 K. HMF was quantified in the aqueous and organic phases with a Zorbax SB-C18 reverse phase column (Agilent, Palo Alto, Calif.), using a 2:8 v/v Methanol: Water (pH=2) gradient at a flow rate of 0.7 ml/min and a column temperature of 303 K.

The experimental protocol for the Shimadzu GC/MS (GC-17A, QP-5000) with Restek RTX-5 crossbond 5% diphenyl, 95% dimethyl, polysiloxane was as follows: An initial oven temperature of 323 K was held for 3 minutes; next, temperature was ramped at 20 K/min until 598 K was reached. Column pressure started at 100 kPa, held for 3 minutes, ramped at 1 kPa/min until 113 kPa was reached, and then held at 113 kPa for 0.75 minutes. Column flow was 1.7 m/min.

The experimental protocol for HPLC with the Agilent Zorbax SB-C18 Column was as follows: Column temperature was set at 308 K and flow rate at 0.7 ml/min. Gradient Used: 0-2 min., 100% water pH=2; 2-3 min transition and hold from 3-10 min with 80% water, 20% methanol; 10-11 min mark transition and hold from 11-15 min mark with 20% water, 80% methanol; 15-16 min mark transition and hold until 35 min mark with 100% water.

To characterize the various compounds, mass spectroscopy was performed starting at 33 m/z. The mass spectra and the retention times matched those of commercially available compounds and literature values from the SDBS database run by the National Metrology Institute of Japan. For all the compounds described below, the retention times for the GC and the HPLC, as well as the UV signature in the HPLC (when available) matched those of the corresponding purchased compounds.

2,5-Dimethylfuran (CAS # 625-86-5), UV/vis: $\lambda_{max}$ 221.5 nm; {Actual MW 96.13} M.S.: m/z (% of max intensity) 39 (14), 41 (12), 43 (100), 51 (11), 53 (41), 67 (5), 81 (16), 95 (34), 96 (37), 97 (3). Retention time in GC/MS is 2.17 min and 19.3 min in HPLC using the methods noted herein.

5-Hydroxymethylfurfural (CAS # 67-47-0), UV/vis: $\lambda_{max}$ 226.2 & 282.8 nm; {Actual MW 126.11} M.S.: m/z (% of max intensity) 37 (10), 38 (18), 39 (56), 41 (100), 51 (12), 53 (14), 81 (3), 97 (43), 109 (4), 125 (4), 126 (22), 127 (2). Retention time in GC/MS is 8.5 min and 10.1 min in HPLC.

2,5-Dihydroxymethylfuran (CAS # 1883-75-6), UV/vis: $\lambda_{max}$ 221.5 nm; {Actual MW 128.13} M.S.: m/z (% of max intensity) 38 (14), 39 (68), 41 (100), 42 (12), 43 (14), 50 (12), 51 (18), 52 (13), 53 (27), 55 (28), 65 (11), 69 (39), 97 (81), 109 (11), 111 (10), 128 (35), 129 (2). Retention time in GC/MS is 8.46 min and 9.7 min in HPLC.

2-Methyl,5-hydroxymethylfuran (CAS # 3857-25-8), UV/vis: $\lambda_{max}$ 221.5 nm; {Actual MW 112.13} M.S.: m/z (% of max intensity) 39 (35), 41 (62), 43 (100), 50 (15), 51 (20), 52 (12), 53 (24), 55 (33), 67 (6), 69 (22), 84 (9), 95 (42), 97 (21), 111 (14), 112 (38), 113 (3). Retention time in GC/MS is 5.75 min and 16.0 min in HPLC.

2-Methylfuran (CAS # 534-22-5), UV/vis: $\lambda_{max}$ 216.8 nm; {Actual MW 82.10} M.S.: m/z (% of max intensity) 38 (15), 39 (100), 41 (11), 43 (18), 50 (16), 51 (18), 53 (79), 54 (13), 81 (47), 82 (72), 83 (4). Retention time in GC/MS is 1.52 min and 17.8 min in HPLC.

Furfural alcohol (CAS # 98-00-0), UV/vis: $\lambda_{max}$ 216.8 nm; {Actual MW 98.10} M.S.: m/z (% of max intensity) 37 (17), 38 (29), 39 (83), 41 (100), 42 (70), 43 (15), 50 (12), 51 (15), 52 (12), 53 (41), 55 (12), 69 (23), 70 (16), 81 (26), 97 (21), 98 (35), 99 (2). GC/MS ret. time 4.50 min. Retention time in GC/MS is 4.50 min and 11.7 min in HPLC.

2,5-Dimethyltetrahydrofuran (CAS # 1003-38-9), {Actual MW 100.16} M.S.: m/z (% of max intensity) 39 (25), 41 (100), 43 (74), 55 (14), 56 (55), 57 (12), 67 (10), 85 (27), 100 (1), 101 (0.1). GC/MS retention time 2.20 min.

1-Chlorobutane (CAS # 109-69-3): {Actual MW 92.57} M.S.: m/z (% of max intensity) 40 (9), 41 (100), 42 (11), 43 (42), 51 (2), 56 (73), 57 (4), 63 (3), 65 (0.7), 73 (0.3), 75 (0.3). GC/MS retention time 1.73 min.

Fructose conversion and HMF selectivity were calculated from the product of the aqueous and organic phase concentrations obtained in the HPLC and their corresponding measured volumes after reaction. Because the value of $V_{org}/V_{aq}$ changes after reaction, final volumes for each run had to be determined individually by measuring the weight and the density of each phase.

See the various Tables for a complete tabulation of the data discussed in the Examples.

Example 1

Dehydration of Glucose

Keto-hexoses produce higher yields of HMF compared to aldo-hexoses. Thus, most of the reported work described hereinabove focuses on fructose dehydration instead of glucose dehydration. Glucose, however, is more abundant and cheaper than fructose. This Example demonstrates that by optimizing the acid concentration and DMSO content in the reactive aqueous phase, glucose can be converted to HMF or furfural with improved selectivity (defined as moles of HMF or furfural produced divided by moles of carbohydrate consumed). This Example is significant because of the abundance of glucose in commercial markets. The ability to use glucose as a feedstock makes the present invention more attractive to large-scale commercialization.

The experiments with glucose (the least reactive of the monosaccharides tested) were run in a biphasic reactor as depicted in FIGS. 1 and 2, using HCl (pH 1.0) as the catalyst. The goal was to maximize the selectivity of the reaction for producing HMF and furfural at 443 K under autonomous pressure. The initial two-phase reaction configuration used pure water as the aqueous phase and MIBK as the organic phase. (In effect, this was the "control" reaction.) In pure water, HMF selectivity from glucose (see Table 6, entry 1) was very low and the reaction yielded insoluble byproducts. Adding an extracting solvent improved the selectivity by 17%, with an almost equal improvement for dehydration. The presence of an extracting solvent thus not only improves the selectivity (presumably by minimizing degradation reactions arising from extended HMF residence in the reactive aqueous phase) but also achieves efficient recovery by extracting 82% of HMF into the organic layer for subsequent isolation.

Adding DMSO to the aqueous reactive phase (60 wt %) with no extracting solvent resulted in dramatic improvement in rates for glucose dehydration along with concomitant increase of 16% in the selectivity of the reaction. Adding DMSO along with an extracting solvent almost doubled the positive effect by improving rates and increasing the selectivity by 42%. A small amount of DMSO (~8.7 wt % as detected by HPLC analysis) was transferred to the organic phase. In real-world industrial practice, the amount of acid added should be kept as low as possible to avoid corrosion effects and loss of HMF by rehydration to levulinic acid. The overall significance of this Example is that adding DMSO to the aqueous phase, and using an efficient extracting phase (MIBK/2-butanol in this Example) not only improves the dehydration rates and selectivity, but also provides a much simpler separation system for product purification and/or subsequent reactions.

Example 2

Effect of pH on Dehydration of Fructose, Glucose, and Xylose

This Example investigated the effects of varying the acid concentration on the dehydration reaction of the simple carbohydrates fructose, glucose, and xylose. These three sugars display a wide difference in their respective reactivities and selectivities toward the desired product. Again, the reactions were run in a biphasic reactor. The reactions were carried out at various pH's (1.0, 1.5, and 2.0) using an aqueous phase of a 5:5 mixture of water:DMSO (w/w) and an organic phase of a 7:3 mixture of MIBK:2-butanol (w/w), at a temperature of 443 K.

The reactivity of the processing conditions increases with increasing DMSO content and decreasing pH (i.e., increasing acidity). Fructose dehydration to HMF had maximum rates for dehydration among the three sugars tested, with selectivities higher than 85%, at high conversion (>90%), at all three levels of acidity. A small increase in both selectivity (about 5%) and rate was observed with a decrease in pH. Similar effects in selectivity and rate were observed for glucose dehydration as HMF selectivity improved by 7% and rate by 400% with a decrease in pH from 2.0 to 1.0. These results clearly indicate the inherent difference in dehydration rates and selectivities of keto-hexoses and aldo-hexoses in similar reacting environments. For xylose dehydration to furfural, a significant rise in the selectivity of up to about 91% (pH 1.0) from 54% (pH 2.0) was observed, along with a 6-fold improvement in dehydration rates when moving from pH 2.0 to pH 1.0.

Example 3

Effect of DMSO Concentration on Glucose Dehydration

In this Example, the effect of DMSO concentration on the dehydration of glucose was investigated. Here, the reactions were carried out at a constant pH (1.0), at 443 K. The aqueous phase reaction solution was then varied (pure water, a 5:5 mixture of water:DMSO (w/w), or a 4:6 mixture of water: DMSO). In each reaction, a 7:3 mixture of MIBK:2-butanol (w/w) was used as the organic phase. Increasing the DMSO content to 50 wt % improves the selectivity by about 18%, with a further increase of about 7% for an additional 10 wt % increase in DMSO content. It is important to note that simply increasing the DMSO content by 10 wt % (from 5:5, water: DMSO to 4:6 water:DMSO) doubles the dehydration rates. While not being bound to any underlying physical or chemical phenomenon, it appears that DMSO suppresses both the formation of condensation byproducts and HMF rehydration by lowering the overall water concentration. The effect, however, is not without certain drawbacks: increasing the DMSO content simultaneously decreases the extracting power of the organic phase as indicated by a decrease in value of R. Moving from a pure water aqueous phase to a 4:6 water:DMSO aqueous phase dropped the value of R from 1.58 to 0.8. This signifies that the water-DMSO mixture had a higher affinity for HMF as compared to pure water.

As pointed out in Example 1, a small fraction of DMSO is carried over to the organic phase, which is undesirable for purposes of recovering purified HMF from the organic phase. The potential problem of DMSO contamination in the HMF product can be minimized by decreasing the DMSO content. The carry-over of DMSO from the aqueous phase into the organic phase dropped by 4% as the DMSO fraction was decreased from 60 wt % to 50 wt % (data not shown). Thus, a balance can be struck by optimizing the DMSO concentration in the aqueous phase to maximize HMF selectivity and to minimize DMSO carry-over into the organic phase. In short, as shown by Examples 1, 2, and 3, by increasing the amount of DMSO content and the acidity, selectivity above 50% can be obtained for glucose dehydration to HMF.

Example 4

Dehydration of Other Carbohydrates

In Examples 1, 2, and 3, the dehydration of simple carbohydrates was optimized by adjusting the pH and DMSO content to achieve good selectivities and reaction rates. In summary, fructose gives an optimum selectivity of 88% at pH 1.5, while xylose achieves 91% selectivity at pH 1.0 with a 5:5 water:DMSO aqueous reacting phase.

For glucose, the least reactive of the monosaccharides tested, increased DMSO levels (up to 60%) and acidity (pH 1.0) is required to achieve a best selectivity of 53%.

Experiments were conducted on the precursor and the corresponding monomers for: (1) inulin and fructose; (2) sucrose, starch, cellobiose and glucose; and (3) xylan and xylose. Reactions were conducted in 5:5 water:DMSO aqueous phase and a 7:3 MIBK:2-butanol organic phase. Reactions were also conducted in a 3:7 (w/w) mixture of water: DMSO, but using dichloromethane as the organic phase.

Subjecting inulin, a fructose precursor molecule obtained from chicory, to dehydration in 5:5 water:DMSO at pH 1.5 gives a selectivity of 77% at high conversion. These values compare favorably (and consistently) with the results for fructose (assuming some loss due to hydrolysis of the polysaccharide to fructose).

Similarly subjecting sucrose (a disaccharide consisting of a fructose residue and a glucose residue) to dehydration in an aqueous phase of 4:6, water:DMSO at pH 1.0 achieves 77% selectivity at 65% sucrose conversion.

At these processing conditions, fructose would be completely converted to HMF. Assuming a glucose conversion of about 30% (a safe assumption based on the data shown in the earlier Examples) the expected selectivity for sucrose is about 81%. Thus, the reaction of sucrose according to the present invention closely follows the selectivity trends set by its monomer units (i.e. fructose at 90% selectivity and glucose at 53% selectivity).

Cellobiose, a glucose dimer connected by 0-1,4 glycoside linkages gave a similar selectivity (52%) as that of the glucose monomer unit.

Soluble starch also gave similar results. Soluble starch (which is a precursor for the glucose monomer) is linked by α-1,4 glycoside linkages and is readily obtained from corn, rice, etc. It is a commodity product. When processed at these same conditions, soluble starch yielded a selectivity for HMF of 43%.

Xylan is used in this Example as a representative polymer for hemi-cellulose. Xylan contains the monomer xylose. When subjected to dehydration in a 5:5 water:DMSO reaction solution, at pH 1.0, xylan gave a selectivity of 66% at high conversions. Thus, by optimizing the processing conditions for simple sugars, a variety of biomass feedstocks (which contain more complex carbohydrates, and which are inexpensive and abundantly available) can be processed with equivalent yields for furan derivates via the dehydration reaction disclosed herein.

Quite remarkably (and wholly unexpectedly), DCM is able to process all of the carbohydrate feed molecules described above at a temperature of 413 K with no acid catalyst at all. All the feedstock molecules matched up well in selectivity at high conversions using a 3:7 mixture of water:DMSO as reactive aqueous phase (without any acid present) and an equal amount of DCM as the extracting organic phase. The unexpected ability of this solvent combination to process a variety of biomass feed molecules with good selectivity and no catalyst required is extremely beneficial because it solves the corrosion problems inherent when conducting reactions at or below pH 2 using mineral acids. By eliminating the harsh acidic environment, the reactions can be carried out without encountering the corrosions problems inherent in low pH environments.

Additionally, the extracting power of the organic phase is higher for DCM (R=1.35) as compared to mixture of 7:3 MIBK:2-butanol (R=0.8). However, this advantage is offset, at least in part, by the significantly increased carry-over of DMSO into the DCM (up to 20 wt %) thereby increasing the subsequent cost of recovering the product.

It has been shown that DCM can undergo hydrolysis in presence water at high temperature (about 250° C.) to generate aqueous HCl (citation omitted). To investigate this phenomenon in the context of the present invention, water and DCM were subjected to 413 K for 3 h. A drop in pH to about 2.0 was noted. Subsequent GC-MS analysis of the aqueous phase showed the presence of a trace amount of HCl. A similar experiment with 3:7 water:DMSO-5 DCM with no sugar feed resulted in the pH dropping to about 1.5, but no trace of HCl was found. This could possibly be because the high fraction of DMSO is associated with water and hence water is not available for the DCM hydrolysis to HCl to take place. However, small traces of decomposition products from DMSO were noticed in GC-MS; these decomposition products may impart acidity to the solvent mixture. Nevertheless, the reaction process using DCM as the organic phase is highly useful because it can process insoluble solid biomass feedstocks, along with soluble carbohydrate moieties, and yield high concentrations of substituted furan compounds (all without requiring an added acid catalyst).

Example 5

Using Different Acids as Catalyst

Along with HCl, experiments were conducted with $H_2SO_4$ and $H_3PO_4$ at a controlled pH 1.5. The aqueous reaction phase was a 5:5 mixture of water:DMSO (w/w) and the organic phase was a 7:3 mixture of MIBK:2-butanol (w/w). Glucose was used as the reactant.

All of the acids tested showed different selectivities, with $H_3PO_4$ achieving a selectivity essentially identical to the selectivity of the 3:7 water:DMSO-DCM system. Sulphuric acid showed the least selectivity (34%) and HCl had a selectivity of 41%. It is important to note that even though the acidity level (pH 1.5) was constant for all of the systems run in this Example, the systems yielded different results for HMF selectivity. In short, at least in this brief Example, the results using the 3:7 DMSO-DCM system could not be emulated by replacing the 3:7 DMSO-DCM with a mineral acid and using MBIK:2-butanol.

Example 6

Adding Salts to the Aqueous Layer

The results from the above Examples show that, for a specific aqueous phase composition, the selectivity for producing HMF can be increased by increasing the value of the extracting ratio, R. This leads to more effective partitioning of the HMF into the organic layer and out of the reactive aqueous layer. Moving more of the HMF into the organic layer thus minimizes undesirable side-reactions of HMF within the aqueous layer. This Example shows that the extracting ratio R can be increased by adding a salt such as NaCl to the aqueous phase.

A first reaction was run at 180° C., with 30 wt % fructose in water, and using 7:3 MIBK:2-butanol as the extracting solvent. This reaction yielded an R value of 1.65. The selectivity for HMF production was equal to 70% at 68% conversion, using HCl as the catalyst (0.25 M), and using a volume of extracting solvent equal to 1.56 times the volume of the aqueous layer.

A second reaction using 30 wt % fructose in water saturated with NaCl, and all other variable identical to the first reaction, yielded an R value of 3.75, more than twice the value obtained without NaCl. HMF selectivity for the second reaction was 77% at 80% conversion. The presence of the metal salt thus enhances the partitioning of HMF into the organic phase by lowering the solubility of HMF in the aqueous phase, which in turn decreases HMF degradation in the aqueous medium.

Example 7

Adding Multiple Salts to the Aqueous Layer

The results from Example 6 show that the addition of a salt to the aqueous layer improves the partitioning of HMF into organic phase by lowering the solubility of HMF in the aqueous phase and thus improves HMF selectivity. Adding more than one salt to the aqueous layer can increase further the value of R. This Example shows that the extraction ratio R is further increased by adding a combination of salts such as NaCl and $NaSO_4$ to the aqueous phase.

A first reaction was run at 180° C., with 30 wt % fructose in water saturated with NaCl, and using 1-butanol as the extracting solvent. This reaction yielded an R value of 2.97. The selectivity for HMF production was equal to 81% at 80% conversion, using HCl as the catalyst (0.25 M), and using a volume of extracting solvent equal to 3.2 times the volume of the aqueous layer.

A second reaction using 30 wt % fructose in water saturated with both NaCl and $NaSO_4$, and all other variable identical to the first reaction, yielded an R value of 4.0. HMF selectivity for the second reaction was 85% at 80% conversion. The presence of both metal salt thus enhances the partitioning of HMF into the organic phase even further than just using NaCl.

TABLE 6

Results for acid catalyzed dehydration of various carbohydrate feedstock's.

| Run # | Sugar | Aqueous Phase Composition | Organic Phase Composition | pH | Time (h:min) | Conversion (%) | Selectivity (%) | HMF or Fur Organic Phase (%) | [HMF or Fur]$_{org}$ [g/cc] | [HMF or Fur]$_{aq}$ [g/cc] | R |
|---|---|---|---|---|---|---|---|---|---|---|---|
| 1 | Glucose | Water | — | 1.0 | 0:45 | 20 | 11 | 0 | 0 | 0.00152 | 0.00 |
| 2 | Glucose | Water | 7:3 MIBK:2-butanol | 1.0 | 0:50 | 17 | 28 | 82 | 0.00103 | 0.00065 | 1.58 |
| 3 | Glucose | 4:6 W:DMSO | — | 1.0 | 0:10 | 41 | 26 | 0 | 0 | 0.00826 | 0.00 |
| 4 | Glucose | 4:6 W:DMSO | 7:3 MIBK:2-butanol | 1.0 | 0 | 43 | 53 | 74 | 0.00434 | 0.00554 | 0.78 |
| 5 | Fructose | 5:5 W:DMSO | 7:3 MIBK:2-butanol | 1.0 | 0:04 | 95 | 89 | 74 | 0.01668 | 0.01901 | 0.88 |
| 6 | Fructose | 5:5 W:DMSO | 7:3 MIBK:2-butanol | 1.5 | 0:06 | 94 | 88 | 76 | 0.01625 | 0.01803 | 0.90 |
| 7 | Fructose | 5:5 W:DMSO | 7:3 MIBK:2-butanol | 2.0 | 0:08 | 95 | 86 | 77 | 0.01616 | 0.01686 | 0.96 |
| 8 | Glucose | 5:5 W:DMSO | 7:3 MIBK:2-butanol | 1.0 | 0:17 | 50 | 47 | 76 | 0.00471 | 0.00504 | 0.94 |
| 9 | Glucose | 5:5 W:DMSO | 7:3 MIBK:2-butanol | 1.5 | 0:42 | 47 | 41 | 76 | 0.00378 | 0.00419 | 0.90 |
| 10 | Glucose | 5:5 W:DMSO | 7:3 MIBK:2-butanol | 2.0 | 1:40 | 48 | 40 | 76 | 0.00367 | 0.00417 | 0.88 |
| 11 | Xylose | 5:5 W:DMSO | 7:3 MIBK:2-butanol | 1.0 | 0:12 | 71 | 91 | 91 | 0.01414 | 0.00474 | 2.98 |
| 12 | Xylose | 5:5 W:DMSO | 7:3 MIBK:2-butanol | 1.5 | 0:27 | 82 | 68 | 92 | 0.01205 | 0.00360 | 3.35 |
| 13 | Xylose | 5:5 W:DMSO | 7:3 MIBK:2-butanol | 2.0 | 0:55 | 53 | 54 | 92 | 0.00618 | 0.00198 | 3.12 |
| 14 | Glucose | 5:5 W:DMSO | 7:3 MIBK:2-butanol | 1.5 | 1:00 | 48 | 34 | 77 | 0.00322 | 0.00354 | 0.91 |
| 15 | Glucose | 5:5 W:DMSO | 7:3 MIBK:2-butanol | 1.5 | 1:00 | 36 | 48 | 75 | 0.00350 | 0.00369 | 0.95 |
| 16 | Inulin | 5:5 W:DMSO | 7:3 MIBK:2-butanol | 1.5 | 0:05 | 98 | 77 | 76 | 0.0163 | 0.0180 | 0.90 |
| 17 | Sucrose | 4:6 W:DMSO | 7:3 MIBK:2-butanol | 1.0 | 0:05 | 65 | 77 | 75 | 0.0101 | 0.0124 | 0.82 |
| 18 | Starch | 4:6 W:DMSO | 7:3 MIBK:2-butanol | 1.0 | 0:11 | 61 | 43 | 74 | 0.0055 | 0.0069 | 0.79 |
| 19 | Cellobiose | 4:6 W:DMSO | 7:3 MIBK:2-butanol | 1.0 | 0:10 | 52 | 52 | 74 | 0.0056 | 0.0070 | 0.79 |
| 20 | Xylan | 5:5 W:DMSO | 7:3 MIBK:2-butanol | 1.0 | 0:25 | 100 | 66 | 91 | 0.0123 | 0.0041 | 2.98 |
| 21 | Fructose | 3:7 W:DMSO | DCM | — | 2:00 | 100 | 87 | 61 | 0.0384 | 0.0315 | 1.22 |
| 22 | Inulin | 3:7 W:DMSO | DCM | — | 2:30 | 100 | 70 | 62 | 0.0344 | 0.0274 | 1.26 |
| 23 | Glucose | 3:7 W:DMSO | DCM | — | 4:30 | 62 | 48 | 63 | 0.0136 | 0.0100 | 1.36 |
| 24 | Sucrose | 3:7 W:DMSO | DCM | — | 4:30 | 82 | 62 | 64 | 0.0245 | 0.0176 | 1.39 |
| 25 | Starch | 3:7 W:DMSO | DCM | — | 11:00 | 91 | 40 | 65 | 0.0189 | 0.0129 | 1.47 |
| 26 | Cellobiose | 3:7 W:DMSO | DCM | — | 9:30 | 85 | 45 | 68 | 0.0206 | 0.0125 | 1.64 |
| 27 | Xylose | 3:7 W:DMSO | DCM | — | 3:00 | 72 | 79 | 87 | 0.0327 | 0.0063 | 5.2 |
| 28 | Xylan | 3:7 W:DMSO | DCM | — | 3:00 | 100 | 76 | 85 | 0.0362 | 0.0084 | 4.3 |

Runs 1-20, except 14 and 15, were carried out in 10 wt % initial concentration of carbohydrate in presence of HCl as catalyst at 443 K.
Runs 14 and 15 were carried out in presence of $H_2SO_4$ and $H_3PO_4$ acid as catalyst respectively.
Run 1-20 used twice the amount of organic solvent by weight with respect to aqueous phase.
Runs 21-28 were carried out with 10 wt % initial concentration of carbohydrate with no catalyst at 413 K in presence of equal amount by weight of dichloromethane (DCM) as solvent.
Aqueous phase and Organic phase composition are based on w/w ratios.
Conversion is defined as ratio of carbohydrate consumed to carbohydrate added initially.
Selectivity is defined as ratio of HMF or Furfural produced to carbohydrate consumed.
R = [HMF or Fur]$_{org}$/[HMF or Fur]$_{aq}$.

TABLE 7

Fructose Dehydration Using Other Inorganic Salts

| Aqueous Phase | Salt | Organic phase | Conversion (%) | Selectivity HMF (%) | R |
|---|---|---|---|---|---|
| 30 wt % fructose | NaBr | 2-butanol | 83 | 78 | 2.0 |
| | KCl | | 89 | 82 | 2.6 |
| | KBr | | 86 | 76 | 1.7 |
| | CaCl$_2$ | | 70 | 78 | 2.7 |
| | CsCl | | 72 | 76 | 2.0 |
| | MgCl$_2$ | | 78 | 77 | 2.8 |
| | NaNO$_3$ | | LOW REACTIVITY AND SOLID FORMATION | | |
| | Na$_2$HPO$_4$ | | | | |
| | NaH$_2$PO$_4$ | | | | |

All dehydration reactions using the salts in the table above were carried out under the same conditions as the experiments reported in Table 1 using salt-saturated aqueous phases and an initial $V_{org}/V_{aq}$=3.2.

Example 8

Estimation for the Energy Consumption in a Distillation Process for DMF and Ethanol In bioethanol production, a typical stream following sugar fermentation contains ~6 wt % ethanol in water. Cardona and Sanchez calculated that the distillation and dehydration of this stream would require approximately 27.4 MJ/(L of EtOH) to produce fuel-grade ethanol. The majority of this energy is associated with phase change of water and ethanol from liquid to vapor. On the same basis, evaporating a stream containing 6 wt % DMF in 1-butanol would require approximately 8.8 MJ/L of DMF. This value represents roughly 33% of the energy required in the ethanol process.

Example 9

Catalyst Preparation and Characterization

Supported Pd and Pt catalysts were prepared by incipient wetness impregnation of Al$_2$O$_3$ ("Catapal B"-brand, Sasol, Houston, Tex.) and SiO$_2$—Al$_2$O$_3$ (MS-25-brand, Al$_2$O$_3$ content 25 wt %, Grace Davison, Columbia, Md.), using tetra-amine platinum (IV) nitrate (Strem Chemicals, Newburyport, Mass.) and tetra-amine palladium (II) nitrate (Strem Chemicals) as the precursor salts. Following impregnation, catalysts were dried in air at 393 K for 12 h and then calcined in a flowing 20% O$_2$/He gas mixture (GHSV~1000 h$^{-1}$) to 533 K (at 1.3 K/min) and held at this temperature for 2 h. Prior to collecting reaction kinetics data and CO chemisorption measurements, each catalyst was reduced in flowing H$_2$ (GHSV~250-1000 h$^{-1}$) at a temperature of 723 K for Pt/SiO$_2$—Al$_2$O$_3$, and at a temperature of 533 K for the Pd/Al$_2$O$_3$ and Pt/Al$_2$O$_3$ catalysts. The temperature was ramped from room temperature to the desired reduction temperature over a period of 8 h and held at the final temperature for 2 h. The irreversible CO uptakes at 300 K (measured on a standard gas adsorption apparatus, see Spiewak, Shen & Dumesic (1995) *J. Phys. Chem.* 99:17640) were 101, 151 and 141 μmoles/g$^{-1}$ of catalyst for the 3 wt % Pt/Al$_2$O$_3$, 3 wt % Pd/Al$_2$O$_3$ and 4 wt % Pt/SiO$_2$—Al$_2$O$_3$ catalysts, respectively.

A mixed Mg—Al-oxide catalyst with Mg/Al atomic ratio=2 was prepared by adding Mg(NO$_3$)$_2$.6H$_2$O (0.188 mol) and Al(NO$_3$)$_3$.9H$_2$O (0.093 mol) to 200 g of H$_2$O. A second solution containing NaOH (0.438 mol) and Na$_2$CO$_3$ (0.113 mol) in 200 g of H$_2$O was slowly added to the Mg/Al aqueous solution in a 1000 ml flask with constant stirring over a period of 3 h. All chemicals were purchased from Aldrich. The pH of the solution was maintained at 11.0 by adding additional NaOH solution (25 wt %) when required. This solution was then heated to 338 K for 18 h. A precipitate formed which was subsequently filtered and washed with DI water until the sodium (Na) content of the filtrate was below 10 ppm as measured by inductively coupled plasma ("ICP") analysis. The precipitate was dried in an oven at 353 K for 12 h to obtain the hydrotalcite. Calcination of the hydrotalcite was carried out in flowing O$_2$ (GHSV~400 h$^{-1}$), during which the temperature was ramped from room temperature to 723 K over 2 h and then held at 723 K for 8 h. The Mg—Al oxide catalyst thus formed was used to carry out aldol condensation reactions, as described below.

The preferred magnesia-zirconia (MgO—ZrO$_2$) catalyst was synthesized using the sol-gel technique described by Aramendia et al. (2004) *J. Mol. Catal. A: Chem.* 218:81 and Aramendia et al. (2004) *Colloids Surf., A* 234:17, starting with magnesium nitrate (Mg(NO$_3$)$_2$.6H$_2$O, Aldrich) and zirconyl nitrate (ZrO(NO$_3$)$_2$, Aldrich). The catalyst was prepared by dissolving 50.9 g of magnesium nitrate and 4.04 g of zirconyl nitrate in 1 liter of deionized (DI) water. The mixture was stirred at room temperature, and NaOH (25 wt %) solution was added until the pH was equal to 10. The gel was aged for 72 h and subsequently vacuum filtered. The precipitate formed was washed with DI water until the Na ion concentration in the filtrate was below 10 ppm, as measured by ICP analysis (PerkinElmer Plasma 400 ICP Emission Spectrometer, PerkinElmer, Fremont, Calif.). The filtrate was then dried in an oven at 393 K from 16 to 24 h. Calcination of the catalyst was carried out in O$_2$ (~100 cm$^3$ (NTP) min$^{-1}$) with a 3 h ramp and a 3 h hold to 873 K. The catalyst thus obtained was used for the initial activity runs for aldol condensation of HMF with acetone, using a HMF: acetone molar ratio of 1:10.

A 5 wt % Pd/MgO—ZrO$_2$ catalyst was prepared by incipient wetness impregnation of Pd (using 5 wt % Pd in tetraaminepalladium (II) nitrate solution from Strem Chemicals) onto the above-mentioned MgO—ZrO$_2$ support. The impregnated catalyst was then calcined in flowing O$_2$ (~120 cm$^3$ (NTP) min$^{-1}$) with a 2 h ramp and a 2 h hold to 723 K. The catalyst so obtained was used for all the aldol condensation and sequential hydrogenation runs described herein.

The irreversible uptakes of CO and CO$_2$ on catalysts at 300 K were measured using a standard gas adsorption apparatus as described in Spiewak, Shen & Dumesic (1995) *J. Phys. Chem.* 99:17640). Prior to CO or CO$_2$ adsorption measurements, the catalyst was reduced in flowing H$_2$, with an 8 h ramp and 2 h hold at 393 K. After reduction, the temperature was ramped to 573 K for 30 min and held for 30 min, while evacuating the cell. The cell was cooled to room temperature, and the adsorbant was then dosed onto the catalyst in 10 to 15 doses until the equilibrium pressure was approximately 5 Torr. Gas in the cell was then evacuated for 30 min at room temperature to a pressure of 10$^{-6}$ Torr, and the adsorbant was again dosed on the sample to determine the amount of reversibly adsorbed CO or CO$_2$. Irreversible uptake was determined by subtracting the second isotherm from the first. Brunauer-Emmett-Teller ("BET") surface areas were measured by N$_2$ adsorption at 77 K on this same system. (Regarding BET surface area measurements, see Brunauer, Emmett and Teller (1938) *J. Am. Chem. Soc.* 60:309.)

X-ray diffraction data were collected with a Cu Kα source using a Scintag PADV diffractometer operating at 40.0 mA and 35.0 kV. Diffraction patterns were collected in continuous scan mode with steps of 0.02 deg sec$^{-1}$. The Scherrer equation was used to estimate crystal size.

A thermo-gravimetric analyzer from Netzsch Thermal Analysis (model TG 209 with a TASC 414/3 temperature controller) was used to analyze the amount of coke formed on the catalyst surface. Approximately 4.5 mg of spent catalyst was weighed and heated to 423 K in 13 min in the presence of flowing O$_2$. The temperature was held at that point for an additional 30 min and ramped to 723 K at a rate of 10 K min$^{-1}$. The amount of carbon on the catalyst was obtained by comparing thermogravimetric analysis ("TGA") data for fresh versus spent catalyst samples.

As shown in Table 8, metal sites (~50±2 μmol/g), surface area (~300±30 m$^2$/g), and average particle size (~11±2 nm) for before and after reaction did not change appreciably, while the phases found (MgO (200, 220), ZrO$_2$ (111, 220)) remained constant. Hence X-ray diffraction (XRD), CO chemisorption and BET surface area measurements show that the catalyst has excellent recycling ability and hydrothermal stability. Base catalyst sites were found to be ~103 μmol/g.

TABLE 8

Characterization of 5 wt % Pd/MgO—ZrO$_2$. All catalysts were calcined and reduced before chemisorption, BET, and XRD analysis. Mean diameter by XRD was estimated by line broadening of powder XRD peaks using the Scherrer equation (±1 nm).

| Chemisorption & BET | Catalyst Before Reaction | After Fur:Ace Reaction | After HMF:Ace Reaction |
|---|---|---|---|
| Metal Sites, μmol/g | 49.0 | 51.7 | 48.8 |
| Base Sites, μmol/g | 103 | — | — |
| Surface Area, m$^2$/g | 292 | 329 | 299 |

| XRD, Identified Phase, Miller Indice, & 2θ | Average Particle Size, Before Reaction/nm | Average Particle Size, After Fur:Ace (run 1)/nm | Average Particle Size, After HMF:Ace (run 15)/nm |
|---|---|---|---|
| MgO (200), 2θ = 30.65° | 9 | 10 | 9 |
| MgO (220), 2θ = 42.79° | 10 | 12 | 11 |
| ZrO$_2$ (111), 2θ = 51.08° | 10 | 13 | 12 |
| ZrO$_2$ (220), 2θ = 62.05° | 10 | 10 | 13 |

Example 10

Dehydration/Hydrogenation Reaction Kinetic Studies

Pelletized catalyst was loaded into a ½ or ¼" outside diameter tubular stainless steel reactor. The catalyst bed was contained in the tubular reactor between two end-plugs of quartz wool (Alltech, a division of Grace Davison Discovery Sciences, Deerfield, Ill.). Type-K thermocouples (Omega) attached to the outside of the reactor were used to measure the reactor temperature, which was controlled with a series 16A type temperature controller (Dwyer Instruments). Prior to reaction kinetics studies, the calcined catalyst was reduced in flowing $H_2$ as outlined above in Example 10. The flow rate of $H_2$ was controlled with mass-flow meters (5850 Brooks Instruments). An HPLC pump (Model 301, Alltech) was used to introduce the aqueous feed solution into the upflow reactor. The hexadecane feed was also introduced to the reactor with an HPLC pump (Model 301, Alltech). The effluent from the reactor was water-cooled in a double-pipe heat exchanger. The effluent liquid was drained periodically for total organic carbon (TOC) analysis (Shimadzu TOC-6001 with autosampler) (Shimadzu Corporation, Kyoto, Japan) of the aqueous phase and for GC analysis of the organic phase (Shimadzu GC-2010 with an flame ionization detector ("FID" detector) and a DB-5 column from Alltech). Each feed was tested for at least 20 h time-on-stream.

The effluent gas stream passed through a back-pressure regulator (GO Regulator, Spartanburg, S.C., Model BP-60) which controlled the system pressure. This off-gas stream was analyzed with two different gas chromatographs: a) the $H_2$ and $CH_4$ were analyzed with a Carle GC (Carle Instruments, Inc., Fullerton, Calif., Series 400 AGC) using a TCD detector and a Porapak Q packed column (Alltech); and b) the $CO_2$ and alkanes heavier than methane were analyzed in a Varian GC-MS (model Saturn 3; Varian, Inc., Palo Alto, Calif.) using a FID detector and a GS-Q capillary column (J&W Scientific, now Agilent Technologies, Santa Clara, Calif.).

Example 11

Tetrahydrofurfural Preparation

Tetrahydrofurfural-2-aldehyde (THF2A) was prepared by selective dehydrogenation of tetrahydrofurfural alcohol (Aldrich) in a gas-phase fixed-bed reactor using a 10 Wt % $Cu/SiO_2$ catalyst (Cab-o-sil), prepared by incipient wetness impregnation as described in Cortright, Sanchez-Castillo & Dumesic (2002) *Appl. Catal. B* 39:353. The feed was introduced to the reactor by an HPLC pump (Model 301, Alltech) at a LHSV=0.67 $h^{-1}$ (LHSV defined as $g_{feed}/(h\ g_{catayst})$), and a helium sweep gas (GHSV=~2500 $h^{-1}$) was used to dilute the feed. The catalyst deactivated continuously during reaction because of coke formation; therefore, to maintain high catalytic activity the temperature of the reaction was increased from 573 to 673 K in 50 K increments every 45 min. Condensable species were separated from the sweep gas in an ice-bath glass condenser. The catalyst was regenerated in an air stream at a GHSV of 2500 $h^{-1}$ for 30 min at 673 K after every 2.25 h of operation. Hydrogen at a GHSV of ~2500 $h^{-1}$ was then fed to the reactor to re-reduce the catalyst.

Example 12

Aldol Condensation Reactions

Aldol condensation reactions were carried out in batch mode at room temperature with the catalysts described above. Different feed solutions were prepared with appropriate molar ratios of the co-reactants, as given in Table 10. The weight ratio of organics to catalyst ranged from 2 to 10. Reactant disappearance was traced versus time using HPLC analysis (Waters 2690 system (Waters Corporation, Milford, Mass.) with a Zorbax SB-C18 5 µm column from Agilent and PDA 960 and RI410 detectors).

Aldol condensation reactions were carried out over the catalyst in the aqueous phase and stopped by filtering the catalyst from the reaction mixture at different times ranging from 2 to 48 h, except for the HMF:Ace (1:1)-3 and HMF:Fur:Ace (1:1:2) feeds in which filtration was done after hydrogenation. The pH of the filtered solutions was approximately 10, and further experiments indicated that the condensation reactions continued to occur in the filtered solution at a rate 10 times slower than with the solid base catalyst present. In addition, the mixed Mg—Al-oxide catalyst lost significant activity upon recycling in sequential batch reactor runs.

In contrast, it was found that a Mg—Zr-oxide catalyst has considerably better stability for aqueous-phase aldol condensation reactions than the Mg—Al-oxide catalyst, with negligible loss of catalytic activity upon recycling. Also, when the Mg—Zr-oxide catalyst was used, the pH of the filtered solution was the same as the pH of the feed solution (pH of 6), thereby minimizing the contribution of aldol condensation reactions occurring homogeneously in the aqueous phase. Similar alkane selectivities were obtained for feeds condensed with Mg—Zr-oxide and Mg—Al-oxide catalysts.

Aldol condensation reactions of HMF:Ace (1:1)-1 and HMF:Ace (1:1)-2 were carried out initially in water, resulting in formation of insoluble products. The precipitate thus formed was dissolved in excess methanol (a methanol to water weight ratio of 2 to 1), and then hydrogenated to form the water-soluble feed to the D/H reactor. Fur:Ace (2:1) was prepared by condensing furfural-acetone (Aldrich) with furfural. The reaction was carried out by mixing 2.1 g furfural, 3.0 g furfural-acetone, 0.6 g NaOH pellets, 80 g water and 80 g methanol in a well-stirred glass reactor at room temperature for 10 h. The solution was then neutralized with HCl and the solvent was evaporated. The resulting solid product was washed with $H_2O$ to remove NaCl.

Example 13

Hydrogenation of Feeds

Aqueous solutions of the condensed feeds were hydrogenated in a batch Parr Reactor (Model # 4566) prior to being fed into the D/H reactor. Feeds were hydrogenated using a 3 wt % $Pd/Al_2O_3$ catalyst at 393 K, 55 bar and a stirring speed of 570 rpm. The amount of catalyst, solvent and reaction time of hydrogenation reactions are listed in Table 11.

Example 14

Reaction System and Analysis Method

All reactions (see Table 9) were carried out in a Parr batch reactor (Model # 4566) with an external temperature and stirring controller (Model # 4836). The reactor was initially loaded with the reaction mixture and air was purged by adding helium up to 55 bar three times before starting the condensation reaction. The reactor was then pressurized to 8 bar with He, heated to the reaction temperature, and stirred at 1000 rpm. After reaching the reaction temperature, the reactor was pressurized to 10 bar. Aldol condensation was stopped after 24 to 26 h of reaction time, and the reactor was then cooled to room temperature. The hydrogenation reaction was started by a similar purging procedure with $H_2$ and pressurizing the reactor to 44 bar before heating. The stirring speed was maintained at 1000 rpm and the reactor was heated to 393 K at which time $H_2$ was added to reach a pressure of 55 bar.

Hydrogenation of the furfural:acetone 1:1 system was complete in 4-6 h at 393 K, and this temperature was employed for all hydrogenation runs with no further optimization. Hydrogenation was stopped after a constant carbon yield in the aqueous phase was reached, which was ensured for all runs by allowing the reaction to proceed for 24 h with monitoring. For Table 9, run 13, after condensation was complete, the aqueous layer was evaporated, leaving catalyst, precipitated monomer, and dimer in the reactor. At this point, hexadecane was added in a volume equal to that of the evaporated aqueous layer and the subsequent hydrogenation reaction was conducted.

Samples were withdrawn from the sampling port during the condensation and hydrogenation reaction. Samples were filtered (using a 0.2 μm polyethersulfone ("PES") syringe membrane filter) before being analyzed by GC (Shimadzu GC-2010 with a FID detector and a DB-5 column from Alltech). For catalyst recycle experiments without calcination (Table 4, runs 2 & 3), the reaction mixture was filtered after the hydrogenation run and the catalyst was dried in an oven at 393 K for 12 to 16 h before reuse. Additionally for the recycle run with catalyst calcination (Table 9, run 4), the catalyst was calcined after use as described above for Pd/MgO—$ZrO_2$. The ICP analysis for Na, Mg and Pd in the final reaction mixture showed negligible leaching of the catalyst components. Total organic carbon (TOC) analysis (Shimadzu TOC-6001 with autosampler) was performed on final reaction mixtures to quantify the total carbon present and to calibrate the GC for reaction products. Furfural:acetone dehydrated monomer (4-(2-furyl)-3-buten-2-one) was hydrogenated for calibration purposes. The self-condensation product of acetone was not identified in HPLC during the condensation runs as confirmed by running standards of diacetone alcohol (4-hydroxy-4-methyl-2-pentanone). Both chemicals were purchased from Aldrich.

The initial studies of aldol condensation with HMF: acetone (molar ratio of 1:10) were carried out in 50 ml glass reactor vessels using an oil bath to control the reaction temperature. Regular samples were withdrawn, filtered (using 0.2 μm PES syringe membrane filter) and the HMF disappearance was monitored using HPLC (Waters 2695 system with a Zorbax SB-C18 5 μm column from Agilent and PDA 960 and RI 410 detectors).

Overall carbon yield and selectivity were calculated based on $C_5$ (for furfural) or $C_6$ (for HMF) units. For furfural: acetone reactions:

$$\text{Overall Carbon Yield \%} = \frac{3*\text{moles } C_3 + 5*\text{moles } C_5 + 8*\text{moles } C_8 + 13*\text{moles } C_{13}}{3*\text{moles } C_3 \text{ fed} + 5*\text{moles } C_5 \text{ fed}} *100$$

$$C_5 \text{ Selectivity \%} = \frac{\text{moles } C_5}{\text{moles } C_5 + \text{moles } C_8 + 2*\text{moles } C_{13}} *100$$

An analogous definition applies for HMF:acetone reactions on a $C_6$ basis.

TABLE 9

Experimental data for aldol condensation and hydrogenation batch reactions.

| Run # | Feed | Molar Ratio | Org/Cat[a] | Time [h][b] | Temperature [K][c] | Volume [ml] | Disappearance [%] Furfural | Selectivity $C_5$ units [%] $C_5$ | $C_8$ | $C_{13}$ | Overall Carbon Yield [%] |
|---|---|---|---|---|---|---|---|---|---|---|---|
| 1 | Fur:Ace [1st] | 1:1 | 6 | 26 | 326 | 250 | 79 | 23 | 34 | 43 | 91 |
| 2 | Fur:Ace [2nd] | 1:1 | 6 | 26 | 326 | 200 | 58 | 43 | 31 | 26 | 93 |
| 3 | Fur:Ace [3rd] | 1:1 | 6 | 26 | 326 | 125 | 58 | 45 | 31 | 24 | 90 |
| 4 | Fur:Ace [4th] | 1:1 | 9 | 26 | 326 | 90 | 76 | 25 | 32 | 43 | 91 |
| 5 | Fur:Ace | 1:1 | 6 | 24 | 353 | 100 | 95 | 5 | 35 | 60 | 88 |
| 6 | Fur:Ace | 1:1 | 6 | 26 | 393 | 100 | 98 | 3 | 35 | 62 | 80 |
| 7 | Fur:Ace | 1:9 | 6 | 24 | 353 | 100 | 96 | 4 | 67 | 29 | 76 |
| 8 | Fur:Ace | 2:1 | 6 | 24 | 353 | 100 | 66 | 37 | 15 | 48 | 91 |
| 9 | Fur:Ace | 2:1 | 6 | 56 | 353 | 100 | 86 | 16 | 12 | 72 | 85 |
| 10 | Fur:Ace | 1:1 | 18 | 25 | 393 | 100 | 90 | 11 | 30 | 59 | 85 |
| 11 | Fur:Ace | 1:1 | 36 | 26 | 393 | 100 | 88 | 14 | 32 | 54 | 82 |
| 12 | Fur:Ace - 0.5% Pd[d] | 1:1 | 6 | 25 | 393 | 112 | 98 | 2 | 33 | 65 | 82 |
| 13 | Fur:Ace - hexadec[e] | 1:1 | 6 | 24 | 353 | 100 | 100 | 0 | 15 | 85 | 71 |

| | | | | | | | HMF | $C_6$ units [%] $C_6$ | $C_9$ | $C_{15}$ | |
|---|---|---|---|---|---|---|---|---|---|---|---|
| 14 | HMF:Ace | 1:1 | 6 | 26 | 298 | 70 | 51 | 42 | 20 | 38 | 100 |
| 15 | HMF:Ace | 1:1 | 6 | 26 | 326 | 100 | 79 | 21 | 18 | 61 | 94 |
| 16 | HMF:Ace | 1:1 | 6 | 26 | 353 | 100 | 88 | 14 | 21 | 65 | 84 |
| 17 | HMF:Ace | 1:1 | 6 | 26 | 393 | 100 | 93 | 11 | 38 | 51 | 67 |

[a]Organic to catalyst ratio by mass
[b]Time for aldol condensation
[c]Reaction temperature for aldol condensation
[d]Reaction carried out over 0.5 wt % Pd/MgO—$ZrO_2$
[e]Aldol condensation carried out in water and hydrogenation conducted in hexadecane solvent at 393 K, 55 bar.

All the runs were carried out in a Parr batch reactor over 5 wt % Pd/MgO—$ZrO_2$, 5 wt % organics in the aqueous solution, condensation pressure of 10 bar, hydrogenation time of 24 h, temperature of 393 K, and pressure of 55 bar (except run 12 using 0.5 wt % Pd and hydrogenated for 40 h).
Recycle runs (Run 1-4) were carried out using the same catalyst, 1st run with fresh catalyst, 2nd and 3rd runs with recycled catalyst without calcinations, and 4th run with calcination.

Example 15

Sample Energy Calculations for Corn to Alkanes

The energy required to produce ethanol from corn (including corn production, corn transportation, ethanol conversion and ethanol transportation) has been reported to be 77,228 BTU/gal$_{ethanol}$. See Shapouri, Duffield & Wang, "The Energy Balance of Corn: An Update," No. 814, U.S. Department of Agriculture, Office of the Chief Economist, 2002. The total energy required (taking into account the EPA's efficiency factor for the energy used to mine and transport coal) for the ethanol conversion plant is 51,779 BTU/gal$_{ethanol}$ (Id.) of which the actual thermal energy is 36,000 BTU/gal$_{ethanol}$. The actual thermal energy required for the distillation process is reported to be 18,000 to 19,800 BTU/gal$_{ethanol}$. See R. Katzen et al. in "Fuels from Biomass and Wastes," Klass & Emert, Eds. (Ann Arbor Science, Ann Arbor, ©1981) pp. 393-402. In short, over half of the energy in the ethanol conversion process is used to distill ethanol from water. Eliminating the distillation process in ethanol production, and assuming that the distillation process accounts for 50% of the energy in the ethanol conversion process, then the energy required to produce ethanol from corn would be 51,000 BTU/gal$_{ethanol}$. Using the ethanol (328 L$_{ethanol}$/ton$_{biomass}$, 1 ton=2,000 lb$_m$) and sugar yields (0.82 ton$_{sugar}$/ton$_{biomass}$) as reported by Klass (see D. L. Klass, "Biomass for Renewable Energy, Fuels and Chemicals," Academic Press, San Diego, © 1998), it is estimated that the energy required for conversion of corn to ethanol (excluding distillation) is equal to 5,400,000 BTU/ton$_{sugar}$, and it is assumed that this value is also equal to the energy required to convert corn to alkanes. Using a value of 2,540 kJ/mole for the heat of combustion of glucose and assuming that sugars are converted to alkanes as given by a stoichiometry analogous to equation 3, then approximately 96% of the energy of the sugar would be retained in the alkane product, giving a heating value for the alkanes of 11,600,000 BTU/ton$_{sugar}$. The overall energy efficiency for conversion of alkanes to corn can now be calculated to be 2.2 by dividing the heating value of the alkanes (11,600,000 BTU/ton$_{sugar}$) by the energy required to produce alkanes (5,400,000 BTU/ton$_{sugar}$). The overall energy efficiency for both conversion of corn to ethanol or corn to alkanes can be increased further by using co-product energy credits. See Shapouri, Duffield & Wang, "The Energy Balance of Corn: An Update," No. 814, U.S. Department of Agriculture, Office of the Chief Economist, 2002.

TABLE 10

Aldol condensation of biomass derived molecules.

| Feed | Wt (%) | Org/cat | Time (h) | Diss (%) | $C_{out}/C_{in}$ (TOC) |
|---|---|---|---|---|---|
| HMF:Ace (1:10) | 11.2 | 6.5 | 5.0 | 100 | 0.90 |
| HMF:Ace (1:1)-1 | 5 | 6 | 9.0 | 80 | N.A. |
| HMF:Ace (1:1)-2 | 5 | 3 | 9.0 | 100 | N.A. |
| HMF:Ace (1:1)-3 | 5 | 6 | 20.9 | N.A. | 0.89 |
| HMF:Fur:Ace (1:1:2) | 5 | 6 | 31.0 | N.A. | 0.93 |
| Fur:DHA (2:1) | 5 | 6 | 4.5 | 58 | 0.90 |
| Fur:DHA (1:1) | 5 | 6 | 2.5 | 68 | 1.00 |
| Fur:DHA (1:3) | 5 | 6 | 2.0 | 89 | 0.98 |
| Fur:HA (1:3) | 5 | 6 | 4.5 | 100 | 1.00 |
| Fur:GHA (1:1) | 5 | 6 | 2.5 | 82 | 0.83 |
| HMF:DHA (1:1) | 5 | 6 | 2.2 | 89 | 0.97 |
| SC DHA | 5 | 6 | 20.0 | 100 | 1.03 |
| SC THF3A | 25 | 10 | 9.0 | 71 | 0.96 |
| SC THF2A | 10 | 2 | 48.0 | 84 | 0.80 |

Aldol condensation reactions were carried out at room temperature with Mg—Al-oxide catalysts.
All feed molecules were purchased from Aldrich, except for THF2A which was prepared from tetrahydrofurfuryl alcohol (Aldrich).
All reactions, except for HMF:Ace (1:1)-1 and HMF:Ace (1:1)-2, were conducted in aqueous solutions.
Feed key:
SC = self condensed;
Fur = furfural;
Ace = acetone;
HMF = 5-hydroxymethylfurfural;
DHA = dihydroxyacetone;
HA = hydroxyacetone;
GHA = glyceraldehyde;
THF3A = tetrahydrofuran-3 carboxyaldehyde;
THF2A = tetrahydrofuran-2 carboxyaldehyde.
Numbers listed in parentheses indicate molar ratio of feeds.
Wt (%) is weight percent organics in aqueous feed solution.
Org/cat is organic to catalyst weight ratio.
Diss (%) is disappearance of HMF, furfural or self condensed feeds tracked by HPLC.
$C_{out}/C_{in}$ is outlet carbon divided by inlet carbon as measured by TOC.
For reactions carried out with methanol this measurement could not be made.
For HMF:Ace (1:1)-3 and HMF:Fur:Ace (1:1:2) feeds the outlet carbon in the aqueous feed was measured after hydrogenation.

TABLE 11

Hydrogenation of biomass derived molecules. (All hydrogenation reactions carried out with a Pd/Al$_2$O$_3$ catalyst at 393 K and 55 bar in a stainless steel batch reactor. See Table 10 for feed key.)

| Feed | Solvent | Wt (%) | Catalyst/Feed Weight Ratio | Reaction Time (h) |
|---|---|---|---|---|
| Furoin | MeOH | 3.2 | 0.45 | 2 |
| Fur:Ace (1:1)-1 | MeOH | 3.8 | 0.40 | 1 |
| Fur:Ace (1:1) org | MeOH | 5.3 | 0.45 | 22 |
| Fur:Ace (1:1)-3 | H$_2$O | 14.0 | 0.09 | 25 |
| Fur:Ace (2:1) | MeOH/H$_2$O | 2.3 | 0.40 | 1 |
| HMF:Ace (1:1)-1 | MeOH/H$_2$O | 2.0 | 0.56 | 1 |
| HMF:Ace (1:1)-2 | MeOH/H$_2$O | 1.8 | 0.65 | 1 |
| HMF:Ace (1:1)-3 | H$_2$O | 1.8 | 0.24 | 8 |
| HMF:Ace (1:10) | H$_2$O | 9.5 | 0.45 | 22 |
| HMF:Fur:Ace (1:1:2) | H$_2$O | 1.9 | 0.33 | 14 |
| Fur:DHA (2:1) | H$_2$O | 1.8 | 0.45 | 22 |
| Fur:DHA (1:1) | H$_2$O | 2.0 | 0.45 | 22 |
| Fur:DHA (1:3) | H$_2$O | 1.7 | 0.45 | 22 |
| Fur:HA (1:3) | H$_2$O | 2.0 | 0.45 | 22 |
| Fur:GHA (1:1) | H$_2$O | 1.6 | 0.45 | 22 |
| HMF:DHA (1:1) | H$_2$O | 2.0 | 0.45 | 22 |
| SC DHA | H$_2$O | 5.0 | 0.45 | 22 |
| SC THF3A | H$_2$O | 5.0 | 0.45 | 22 |
| SC THF2A | H$_2$O | 3.9 | 0.45 | 22 |

TABLE 12

Conversion and process conditions for 4-phase dehydration/hydrogenation of biomass-derived molecules.

| Entry | Feed | Wt (%) | WHSV (h$^{-1}$) | Org/Aq | % Carbon in Phase Org | Gas | Aq |
|---|---|---|---|---|---|---|---|
| S1 | Sorbitol | 5.0 | 1.26 | 0.0 | — | 86.8 | 18.6 |
| S2 | | 5.0 | 1.26 | 1.0 | 41.3 | 41.0 | 11.9 |
| S3 | | 5.0 | 1.26 | 3.0 | 38.5 | 31.2 | 15.5 |
| S4 | | 1.0 | 1.26 | 3.0 | 35.7 | 46.4 | 10.3 |
| S5 | Furoin | 2.0 | 0.26 | 3.0 | 69.2 | 18.5 | 2.3 |
| S6 | Fur:Ace (1:1)-1 | 1.9 | 0.26 | 3.0 | 100.0 | 6.3 | 1.6 |

TABLE 12-continued

Conversion and process conditions for 4-phase dehydration/hydrogenation of biomass-derived molecules.

| Entry | Feed | Wt (%) | WHSV ($h^{-1}$) | Org/Aq | % Carbon in Phase Org | Gas | Aq |
|---|---|---|---|---|---|---|---|
| S7 | Fur:Ace (1:1) org* | 5.0 | 0.51 | ∞ | 73.2 | 7.8 | NA |
| S8 | Fur:Ace (1:1)-3 | 12.5 | 0.29 | 3.0 | 91.2 | 4.1 | 0.7 |
| S9 | Fur:Ace (2:1) | 1.0 | 0.29 | 3.0 | 79.0 | 2.4 | 0.8 |
| S10 | HMF:Ace (1:1)-1 | 1.8 | 0.25 | 3.0 | 66.1 | 15.7 | 1.5 |
| S11 | HMF:Ace (1:1)-2† | 1.9 | 0.26 | 3.0 | 69.5 | 7.7 | 0.9 |
| S12 | HMF:Ace (1:1)-3 | 1.8 | 0.29 | 3.0 | 53.3 | 31.1 | 2.3 |
| S13 | HMF:Ace (1:10) | 9.5 | 0.35 | 0.7 | 77.2 | 10.3 | 20.0 |
| S14 | HMF:Fur:Ace (1:1:2) | 1.9 | 0.29 | 3.0 | 48.5 | 27.8 | 3.1 |
| S15 | Fur:DHA (2:1) | 1.8 | 0.20 | 3.0 | 46.6 | 47.9 | 5.2 |
| S16 | Fur:DHA (1:1) | 2.0 | 0.20 | 3.0 | 43.9 | 47.7 | 5.3 |
| S17 | Fur:DHA (1:3) | 1.7 | 0.20 | 3.0 | 35.9 | 58.9 | 10.5 |
| S18 | Fur:HA (1:3) | 2.0 | 0.25 | 3.0 | 29.6 | 55.6 | 16.7 |
| S19 | Fur:GHA (1:1) | 1.6 | 0.25 | 3.0 | 48.6 | 47.0 | 8.7 |
| S20 | HMF:DHA (1:1) | 2.0 | 0.20 | 3.0 | 44.0 | 41.8 | 5.3 |
| S21 | SC DHA | 5.0 | 0.27 | 3.0 | 19.1 | 59.5 | 11.0 |
| S22 | SC THF3A | 5.0 | 0.35 | 0.7 | 53.2 | 44.1 | 4.2 |
| S23 | SC THF2A | 3.9 | 0.35 | 0.7 | 47.9 | 20.8 | 13.0 |

*Fur:Ace (1:1) org was added to the hexadecane feed and no aqueous flow was used for this feed.
†This feed was condensed with twice the amount of Mg—Al-oxide than the feed above it (Entry S10).
All four-phase D/H reactions were carried out at 523 to 538 K, 52 to 60 bar and $H_2$ gas hourly space velocity (v/v) of 1000 to 3000 $h^{-1}$.
For the sorbitol feed, a physical mixture of 1.5 g USY zeolite and 2.9 g 3 wt % $Pt/Al_2O_3$ catalyst was used, which had similar activity and selectivity to a 4 wt % $Pt/SiO_2$—$Al_2O_3$ catalyst.
For all other feeds, a 4 wt % $Pt/SiO_2$—$Al_2O_3$ catalysts was used.
Each experimental point was collected after 20 h time-on-stream.
Condensed feeds were prepared by aldol condensation at room temperature using Mg—Al-oxide and NaOH catalysts.
See Table 10 for feed key.
Numbers listed in parentheses indicate molar ratio of feeds.
All feeds (except sorbitol) were hydrogenated in a Parr reactor with a $Pd/Al_2O_3$ catalyst prior to conversion in the four-phase D/H reactor.
Entries S5 to S7 and S9 to S11 were hydrogenated in methanol or a methanol/water mixture, with all other feeds being hydrogenated in $H_2O$.
Abbreviations:
Wt (%) refers to weight percent organics in aqueous feed solution.
WHSV is weight hourly space velocity; mass of aqueous feed solution per mass of catalyst per hour.
Org/Aq is the organic (hexadecane) to aqueous volumetric feed ratio.

TABLE 13

Alkane and $CO_2$ selectivities from 4-phase dehydration/hydrogenation of biomass derived-molecules.

| Entry | Feed | $CO_2$ | $C_1$ | $C_2$ | $C_3$ | $C_4$ | $C_5$ | $C_6$ | $C_7$ | $C_8$ | $C_9$ | $C_{10}$ | $C_{11}$ | $C_{12}$ | $C_{13}$ | $C_{14}$ | $C_{15}$ |
|---|---|---|---|---|---|---|---|---|---|---|---|---|---|---|---|---|---|
| S1 | Sorbitol | 14.6 | 3.6 | 4.7 | 8.5 | 11.6 | 20.5 | 36.6 | 0.0 | 0.0 | 0.0 | 0.0 | 0.0 | 0.0 | 0.0 | 0.0 | 0.0 |
| S2 | | 15.0 | 2.2 | 4.7 | 8.8 | 12.3 | 19.4 | 37.7 | 0.0 | 0.0 | 0.0 | 0.0 | 0.0 | 0.0 | 0.0 | 0.0 | 0.0 |
| S3 | | 15.3 | 2.1 | 5.4 | 8.4 | 8.7 | 23.4 | 36.5 | 0.0 | 0.0 | 0.1 | 0.0 | 0.0 | 0.0 | 0.0 | 0.0 | 0.0 |
| S4 | | 20.4 | 3.1 | 9.1 | 10.1 | 10.3 | 21.3 | 25.3 | 0.0 | 0.0 | 0.4 | 0.0 | 0.0 | 0.0 | 0.0 | 0.0 | 0.0 |
| S5 | Furoin | 5.2 | 5.2 | 0.0 | 2.8 | 8.0 | 9.2 | 1.8 | 0.3 | 5.4 | 26.2 | 34.0 | 0.7 | 0.3 | 0.3 | 0.4 | 0.2 |
| S6 | Fur:Ace (1:1)-1 | 1.8 | 2.2 | 0.0 | 0.0 | 0.1 | 0.2 | 0.3 | 15.0 | 77.7 | 0.6 | 0.2 | 0.4 | 0.3 | 0.4 | 0.4 | 0.4 |
| S7 | Fur:Ace (1:1) org | 0.0 | 4.7 | 0.2 | 1.7 | 1.8 | 2.0 | 1.9 | 4.5 | 71.4 | 2.4 | 2.2 | 2.2 | 2.1 | 2.4 | 0.6 | 0.0 |
| S8 | Fur:Ace (1:1)-3 | 1.7 | 0.4 | 0.0 | 0.1 | 0.1 | 0.1 | 0.2 | 17.1 | 64.4 | 7.4 | 5.8 | 2.5 | 0.1 | 0.1 | 0.1 | 0.0 |
| S9 | Fur:Ace (2:1) | 0.0 | 3.0 | 0.0 | 0.0 | 0.0 | 0.4 | 0.7 | 1.0 | 2.1 | 0.8 | 0.5 | 2.1 | 19.7 | 68.6 | 0.6 | 0.5 |
| S10 | HMF:Ace (1:1)-1* | 6.8 | 3.3 | 0.0 | 0.0 | 6.0 | 14.6 | 9.3 | 0.4 | 6.8 | 9.5 | 0.0 | 0.0 | 0.7 | 8.5 | 19.5 | 14.5 |
| S11 | HMF:Ace (1:1)-2* | 5.0 | 4.0 | 0.0 | 0.0 | 1.5 | 3.2 | 2.2 | 0.4 | 2.9 | 4.6 | 0.2 | 0.4 | 1.5 | 13.5 | 32.9 | 27.6 |
| S12 | HMF:Ace (1:1)-3 | 5.7 | 3.5 | 0.0 | 23.5 | 3.8 | 10.0 | 7.0 | 0.7 | 5.9 | 6.9 | 0.1 | 0.3 | 1.0 | 6.2 | 14.5 | 10.9 |
| S13 | HMF:Ace (1:10)† | 6.0 | 0.9 | 0.0 | 0.0 | 2.6 | 4.8 | 1.1 | 3.9 | 27.4 | 41.2 | 1.9 | 0.2 | 0.5 | 4.1 | 3.6 | 0.8 |
| S14 | HMF:Fur:Ace (1:1:2) | 4.0 | 3.0 | 0.0 | 25.3 | 3.8 | 7.2 | 3.3 | 2.5 | 10.2 | 5.6 | 0.0 | 1.0 | 4.8 | 14.3 | 10.8 | 4.4 |
| S15 | Fur:DHA (2:1) | 10.8 | 3.4 | 5.0 | 9.6 | 22.7 | 22.6 | 5.7 | 6.8 | 7.3 | 0.8 | 0.8 | 1.0 | 2.0 | 1.5 | 0.0 | 0.0 |
| S16 | Fur:DHA (1:1) | 9.6 | 3.7 | 10.1 | 10.7 | 18.3 | 21.0 | 6.6 | 8.0 | 7.4 | 1.5 | 0.8 | 0.5 | 1.3 | 0.4 | 0.2 | 0.0 |
| S17 | Fur:DHA (1:3) | 13.8 | 5.7 | 17.5 | 18.9 | 7.6 | 9.5 | 5.1 | 7.9 | 11.0 | 0.8 | 0.7 | 0.3 | 0.7 | 0.4 | 0.0 | 0.0 |
| S18 | Fur:HA (1:3) | 9.3 | 7.4 | 18.8 | 23.8 | 8.1 | 7.7 | 3.0 | 5.5 | 11.0 | 1.2 | 2.1 | 0.3 | 0.4 | 1.1 | 0.2 | 0.2 |
| S19 | Fur:GHA (1:1) | 10.4 | 4.8 | 5.6 | 9.3 | 18.5 | 22.0 | 8.5 | 5.7 | 9.6 | 1.7 | 0.9 | 0.6 | 0.4 | 0.3 | 1.4 | 0.3 |
| S20 | HMF:DHA (1:1) | 12.5 | 3.7 | 8.5 | 10.0 | 9.3 | 22.1 | 17.1 | 4.6 | 5.0 | 3.1 | 1.1 | 1.1 | 1.1 | 0.3 | 0.2 | 0.0 |
| S21 | SC DHA | 16.5 | 11.1 | 19.8 | 27.5 | 3.6 | 6.9 | 10.7 | 1.3 | 0.5 | 0.6 | 0.6 | 0.3 | 0.4 | 0.0 | 0.3 | 0.0 |
| S22 | SC THF3A‡ | 9.4 | 0.7 | 0.0 | 4.2 | 23.4 | 25.1 | 0.1 | 3.4 | 6.7 | 11.6 | 14.3 | 0.1 | 0.9 | 0.0 | 0.0 | 0.0 |
| S23 | SC THF2A§ | 11.4 | 1.3 | 0.0 | 5.1 | 15.1 | 9.9 | 0.5 | 5.2 | 13.0 | 17.7 | 19.4 | 0.3 | 0.9 | 0.3 | 0.0 | 0.0 |

*$C_3$ selectivity is zero because acetone was removed during separation of hydrogenated products from methanol-water solution.
†Propane is not included in the alkane selectivity calculation for this feed.
‡Liquid alkanes produced in this feed were mostly branched. The $C_{10}$ alkane was 3-methyl-5-dimethyl-heptane.
§Liquid alkanes produced in this feed were mostly branched. The $C_{10}$ alkane was 4-methylnonane.
(Table 12 contains relevant process conditions and conversion data.
Table 10 contains feed key.
Selectivity = (moles product × number of carbon atoms in product)/(total moles of carbon atoms in products) × 100.
The selectivity only takes into account the products in the organic and gas phases.
Alkane products are mostly straight chain, except for the SC THF3A and SC THF2A feeds.
At lower conversions small amounts of alcohols (<10% of total products) are also observed in the organic phase.)

An experiment was performed to measure the aqueous phase concentration of carbon (normalized to the initial concentration of carbon in the batch reactor) versus time during aldol condensation over a bifunctional Pd/MgO—$ZrO_2$ catalyst at various temperatures, followed by sequential hydrogenation in the same batch reactor at 393 K. The results show that as the aldol condensation proceeds, monomer and dimer species form and precipitate out of the aqueous solution, and the amount of carbon in the aqueous phase decreases accordingly. It is important to note that during this reaction the Pd on the catalyst is inert, because the performance of the Pd/MgO—$ZrO_2$ catalyst is identical to the performance of MgO—$ZrO_2$ during aldol condensation. Approximately 80% of the furfural has disappeared after a period of 24 h under these reaction conditions. The reactor was then pressurized to about 55 bar with hydrogen to initiate subsequent hydrogenation of the furan rings and thereby increase the solubility of monomer and dimer species in the aqueous phase. This hydrogenation step leads to an increase in the concentration of carbon in the liquid phase. For example, while the carbon concentration in the aqueous phase after aldol condensation at 326 K decreases to about 44% of the initial carbon concentration, this value increases to about 94% after the hydrogenation step. These results illustrates the ability of the bifunctional Pd/MgO—$ZrO_2$ catalyst to facilitate a single-reactor, aqueous phase process that combines aldol condensation with sequential hydrogenation (as shown schematically in FIG. 1), in which the aqueous phase carbon lost during the aldol condensation step is returned to the aqueous phase during the hydrogenation step. Table 9 shows the details of various runs conducted. TGA experiments identified 48%, 21% and 95% of the carbon missing from the carbon balance to be located on the catalyst for runs 1, 7 and 15 in Table 9, respectively. For run 7, furfural:acetone 1:9, roughly 63% of the missing carbon is caused by the initial purging of gas from the reactor (because of the high concentration and volatility of acetone), leading to an overall carbon yield equal to 96%.

As noted above, experiments were conducted to study the stability and recyclability of the bifunctional 5 wt % Pd/MgO—$ZrO_2$ for aldol condensation of acetone with furfural (molar ratio 1:1) at 326 K, followed by hydrogenation at 393 K. The catalyst was recycled for use in runs 2 and 3 without any intermediate regeneration, whereas the catalyst was subjected to a calcination treatment prior to run 4. Table 9, runs 1-4, show that selectivity for the formation of the dimer adduct decreases by about 18% for recycle runs 2 and 3, while still maintaining good overall carbon yield (>90%), and returns to original levels for run 4. This result shows that the catalyst retains most of its activity and selectivity for at least three runs without requiring regeneration and can be completely regenerated through calcination. As shown in Table 10, metal sites (~50±2 μmol/g), surface area (~300±30 $m^2/g$), and average particle size (~11±2 nm) for before and after reaction did not change appreciably, while the phases found (MgO (200, 220), $ZrO_2$ (111, 220)) remained constant. Hence XRD, CO chemisorption and BET measurements show that the catalyst has excellent recycling ability and hydrothermal stability. Aldol condensation does not take place homogeneously in the aqueous phase by dissolved basic species because the rate of aldol condensation was negligible after the MgO—$ZrO_2$ catalyst was removed from the aqueous solution. This further shows that the catalyst is stable.

Table 9, runs 1, 5, 6, show experimental results obtained at reaction temperatures from 298 to 393 K for aldol condensations of furfural with acetone at a molar ratio of 1:1. The rate of reaction increases with temperature; however, the overall carbon yield in the aqueous solution after aldol condensation (followed by hydrogenation) decreases at temperatures above 353 K, probably caused by the formation of coke on the catalyst during aldol condensation. As the temperature is increased from 326 to 353 K, the selectivity for dimer increases by 17% with no significant change in the overall carbon yield. In contrast, as the temperature is increased further from 353 to 393 K, the dimer selectivity remains the same but the overall carbon yield decreases by 8%. Thus, it appears that the optimum temperature for aldol condensation of furfural is about 353 K, with this temperature providing a compromise between the selectivity for heavier product and overall carbon yield.

In the case of aldol condensation between HMF and acetone (Table 9, runs 14-17), the overall yield of carbon is 67% at 393 K. At lower temperatures, there is a marked increase in selectivity for dimer (increased by 23%) as temperature increased from 298 to 326 K. There was also seen a 10% decrease in overall carbon yield as temperature was increased further from 326 to 353 K. Thus, the temperature trends for HMF and furfural are similar. Accordingly, the optimum temperature for aldol condensation of HMF with acetone is about 326 K. This example shows that the aldol condensation temperature has a significant effect on the selectivity of the reaction and the overall yield of the process, with the optimum temperature for condensation with acetone being higher for furfural compared to HMF. At these optimum temperatures, the furfural:acetone reaction achieves a higher final conversion (by 16%) but a lower dimer-to-monomer ratio (1.8 versus 3.4) as compared to the HMF:acetone reaction.

The results presented in Table 9, runs 5 and 7-9 show that the molar ratio of reactants for aldol condensation plays a significant role in controlling the reaction selectivity. The presence of excess acetone (furfural:acetone molar ratio of 1:9) leads primarily to the formation of monomer, because it is more probable that a furfural molecule will react with an acetone molecule in contrast to reacting with a monomer species. When the molar ratio of furfural:acetone was increased from 1:9 to 1:1, the selectivity for the formation of dimer species was increased by 31%, and this selectivity increased a further 12% when the furfural:acetone ratio was increased from 1:1 to 2:1. As the furfural:acetone ratio is increased the condensation step requires additional time as shown by an increase in dimer selectivity by 24% when the condensation step is carried out for 56 h instead of 24 h.

Experiments were carried out to study the effects of varying the organic/catalyst ratio, the palladium loading, and of performing the hydrogenation step in hexadecane instead of water. Increasing the organic/catalyst mass ratio from 6 to 36 (Table 9, runs 6, 10, 11) does not have an effect on the selectivity and the overall carbon yield of the process. Decreasing the amount of Pd on the MgO—$ZrO_2$ catalyst from 5 to 0.5 wt % (Table 9, runs 6, 12) increased by about an order of magnitude the time required to reach high overall yields of carbon in the aqueous phase at 393 K (i.e., from about 5 to about 40 h). In Table 9, run 13, the aqueous solution was removed at the end of the aldol condensation step, leaving the insoluble monomer and dimer species on the catalyst surface; and the reactor was then filled with hexadecane, followed by hydrogenation at 393 K. This treatment led to the formation of hydrogenated monomer and dimer species in the hexadecane solvent, with an overall carbon yield of around 71%, indicating that the hydrogenated form of monomer and dimer can be blended with diesel fuel without the need to convert these species into alkanes, thereby eliminating the need for the further APD/H processing step.

The Examples demonstrate that the Pd/MgO—ZrO$_2$ catalyst tested here is an active, selective, and hydrothermally stable catalyst for aldol condensation over basic sites (MgO—ZrO$_2$) followed by sequential hydrogenation over metal sites (Pd). This bifunctional catalytic system thus allows carbohydrate-derived compounds, such as furfural and HMF, to be converted in a single reactor to large water-soluble intermediates for further aqueous phase processing to produce liquid alkanes. The selectivity and overall yield of the process can be controlled by the reaction temperature and the molar ratio of the aldol condensation reactants.

What is claimed is:

1. A method for making a composition comprising alkanes, the method comprising:
   (a) dehydrating a feedstock solution comprising a carbohydrate, in the presence of an acid catalyst, to yield at least one furan derivative compound, in a reaction vessel containing a biphasic reaction medium comprising an aqueous reaction solution and a substantially immiscible organic extraction solution, wherein the aqueous reaction solution, the organic extraction solution, or both the aqueous reaction solution and the organic extraction solution contain at least one modifier to improve selectivity of the dehydration to yield the furan derivative compound; then
   (b) subjecting the furan derivative compound of step (a) to at least one self-aldol condensation reaction or a crossed-aldol condensation reaction in an aqueous monophasic or an aqueous/organic biphasic reaction medium with another carbonyl compound to yield a beta-hydroxy carbonyl compound and/or an alpha-beta unsaturated carbonyl compound; then
   (c) hydrogenating the beta-hydroxy carbonyl and/or alpha-beta unsaturated compounds of step (a) to yield a saturated or partially saturated compound; and then
   (d) hydrodeoxygenating the saturated or partially saturated compound of step (c) to yield a C$_6$ to C$_{15}$ alkane.

2. The method of claim 1, wherein step (b) further comprises running the self-aldol condensation reaction or the crossed-aldol condensation reaction, in the presence of a mineral base catalyst or a solid base catalyst comprising magnesium, zirconium, and oxygen.

3. The method of claim 1, wherein step (b) comprises running the self-aldol condensation reaction or the crossed-aldol condensation reaction in a biphasic reaction medium comprising an aqueous reaction solution comprising a salt, a substantially immiscible organic extraction solution, and NaOH as a mineral base catalyst.

4. The method of claim 1, wherein in step (a), in step (b), or in both steps (a) and (b), the reaction medium further comprises at least one salt, thereby yielding a saline aqueous reaction solution.

5. The method of claim 4, wherein the at least one salt comprises a cation and an anion selected from the group consisting of acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate, and bis-trifluorsulfonimide.

6. The method of claim 1, wherein the acid catalyst is a mineral acid.

7. The method of claim 1, wherein the acid catalyst is a zeolite.

8. The method of claim 1, wherein the acid catalyst is selected from the group consisting of silica-, silica-alumina, and titania-based supports functionalized by acid groups.

9. The method of claim 1, wherein the acid catalyst is a cation exchange resin.

10. The method of claim 1, wherein the acid catalyst is a Lewis acid.

11. The method of claim 1, wherein the acid catalyst is selected from the group consisting of heteropolyacids, HCl, HNO$_3$, H$_2$SO$_4$, H$_3$PO$_4$, H$_3$BO$_3$, oxalic acid, levulinic acid, citric acid, NbOPO$_4$, and vanadium phosphate.

12. The method of claim 1, wherein the aqueous reaction solution contains the modifier, and the modifier comprises a dipolar, aprotic additive.

13. The method of claim 1, wherein the aqueous reaction solution contains the modifier and the modifier is selected from the group consisting of water-miscible alcohols, water-miscible ketones, and water-soluble polymers.

14. The method of claim 1, wherein the organic extraction solution contains the modifier and the modifier is selected from the group consisting of a primary, secondary, linear, branched, or cyclic C$_1$- to C$_{12}$-alcohols.

15. The method of claim 1, wherein the organic extraction solution comprises a solvent selected from the group consisting of water-immiscible, linear, branched, or cyclic alcohols, ethers, and ketones.

16. The method of claim 1, wherein the organic extraction solution comprises a solvent selected from the group consisting of unsubstituted aliphatic and aromatic hydrocarbons and halo-substituted aliphatic and aromatic hydrocarbons.

17. A method for making alkanes comprising:
   (a) converting a carbohydrate reactant to yield at least one carbonyl compound having an alpha-position hydrogen, in the presence of an acid catalyst, in a reaction vessel containing a biphasic reaction medium comprising an aqueous reaction solution and a substantially immiscible organic extraction solution, wherein the aqueous reaction solution, the organic extraction solution, or both the aqueous reaction solution and the organic extraction solution contain at least one modifier to improve selectivity of the process to yield the carbonyl compound having an alpha-position hydrogen; then
   (b) subjecting the carbonyl compound of step (a) to at least one self-aldol condensation reaction or a crossed-aldol condensation reaction in an aqueous monophasic or an aqueous/organic biphasic reaction medium with another carbonyl compound to yield a beta-hydroxy carbonyl compound and/or an alpha-beta unsaturated carbonyl compound; then
   (c) hydrogenating the beta-hydroxy carbonyl and/or the alpha-beta unsaturated carbonyl compounds of step (b) to yield a saturated or partially saturated compound; and then
   (d) hydrodeoxygenating the saturated or partially saturated compound of step (c) to yield an alkane.

18. The method of claim 17, wherein step (b) comprises running the self-aldol condensation reaction or the crossed-aldol condensation reaction in the presence of a mineral base catalyst or a solid base catalyst comprising magnesium, zirconium, and oxygen.

19. The method of claim 17, wherein step (b) comprises running the self-aldol condensation reaction or the crossed-aldol condensation reaction in a biphasic reaction medium comprising an aqueous reaction solution comprising a salt, a substantially immiscible organic extraction solution, and NaOH as a mineral base catalyst.

20. The method of claim 17, wherein in step (a), step (b), or both steps (a) and (b), the reaction medium further comprises at least one salt, thereby yielding a saline aqueous reaction solution.

21. The method of claim 17, wherein in step (a) the acid catalyst is a mineral acid.

22. The method of claim 17, wherein the acid catalyst is selected from the group consisting of heteropolyacids, HCl, $HNO_3$, $H_2SO_4$, $H_3PO_4$, $H_3BO_3$, oxalic acid, levulinic acid, citric acid, $NbOPO_4$, and vanadium phosphate.

23. The method of claim 17, wherein the aqueous reaction solution contains the modifier, and the modifier comprises a dipolar, aprotic additive.

24. The method of claim 17, wherein the aqueous reaction solution contains the modifier and the modifier is selected from the group consisting of water-miscible alcohols, water-miscible ketones, and water-soluble polymers.

25. The method of claim 17, wherein the organic extraction solution contains the modifier and the modifier is selected from the group consisting of a primary, secondary, linear, branched, or cyclic $C_1$- to $C_{12}$-alcohols.

26. The method of claim 17, wherein the organic extraction solution comprises a solvent selected from the group consisting of water-immiscible, linear, branched, or cyclic alcohols, ethers, and ketones.

27. The method of claim 17, wherein the organic extraction solution comprises a solvent selected from the group consisting of unsubstituted aliphatic and aromatic hydrocarbons and halo-substituted aliphatic and aromatic hydrocarbons.

28. A method for making alkanes comprising:
(a) dehydrating a $C_6$ sugar to yield hydroxymethylfurfural, in the presence of an acid catalyst, in a reaction vessel containing a biphasic reaction medium comprising an aqueous reaction solution and a substantially immiscible organic extraction solution, wherein the aqueous reaction solution, the organic extraction solution, or both the aqueous reaction solution and the organic extraction solution contain at least one modifier to improve selectivity of the dehydration to yield hydroxymethylfurfural; then
(b) subjecting the hydroxymethylfurfural to at least one crossed-aldol condensation reaction in an aqueous monophasic or an aqueous/organic biphasic reaction medium with an aldehyde or a ketone to yield a beta-hydroxy carbonyl and/or an alpha-beta unsaturated carbonyl having at least seven (7) carbon atoms; then
(c) hydrogenating the beta-hydroxy carbonyl and/or alpha-beta unsaturated carbonyl to yield a saturated or partially saturated compound; and then
(d) hydrodeoxygenating the saturated or partially saturated compound to yield an alkane having at least seven (7) carbon atoms.

29. The method of claim 28, wherein step (b) yields a beta-hydroxy carbonyl and/or an alpha-beta unsaturated carbonyl having at least nine (9) carbon atoms; and step (d) yields an alkane having at least nine (9) carbon atoms.

30. The method of claim 28, wherein step (b) yields a beta-hydroxy carbonyl and/or an alpha-beta unsaturated carbonyl having at least eleven (11) carbon atoms; and step (d) yields an alkane having at least eleven (11) carbon atoms.

31. The method of claim 28, wherein step (b) yields a beta-hydroxy carbonyl and/or an alpha-beta unsaturated carbonyl having at least thirteen (13) carbon atoms; and step (d) yields an alkane having at least thirteen (13) carbon atoms.

32. The method of claim 28, wherein step (b) yields a beta-hydroxy carbonyl and/or an alpha-beta unsaturated carbonyl having at least fifteen (15) carbon atoms; and step (d) yields an alkane having at least fifteen (15) carbon atoms.

33. The method of claim 28, wherein step (b) comprises running the self-aldol condensation reaction or the crossed-aldol condensation reaction in the presence of a mineral base catalyst or a solid base catalyst comprising magnesium, zirconium, and oxygen.

34. The method of claim 28, wherein in step (a), step (b), or both steps (a) and (b), the aqueous reaction solution further comprises at least one salt, thereby yielding a saline aqueous reaction solution.

35. The method of claim 28, wherein step (b) comprises running the self-aldol condensation reaction or the crossed-aldol condensation reaction in a biphasic reaction medium comprising an aqueous reaction solution comprising a salt, a substantially immiscible organic extraction solution, and NaOH as a mineral base catalyst.

36. The method of claim 28, wherein in step (a) the acid catalyst is a mineral acid.

37. A method for making a liquid transportation fuel, the method comprising:
(a) dehydrating a feedstock solution comprising a carbohydrate, in the presence of an acid catalyst, to yield at least one carbonyl compound, in a reaction vessel containing a biphasic reaction medium comprising an aqueous reaction solution and a substantially immiscible organic extraction solution, wherein the aqueous reaction solution, the organic extraction solution, or both the aqueous reaction solution and the organic extraction solution contain at least one modifier to improve selectivity of the dehydration to yield the carbonyl compound; then
(b) subjecting a carbonyl compound of step (a) to at least one self-aldol condensation reaction or a crossed-aldol condensation reaction in an aqueous monophasic or an aqueous/organic biphasic reaction medium with another carbonyl compound to yield a beta-hydroxy carbonyl compound and/or an alpha-beta unsaturated carbonyl compound; then
(c) hydrogenating the beta-hydroxy carbonyl and/or alpha-beta unsaturated compounds of step (b) to yield a saturated or partially saturated compound; and then
(d) hydrodeoxygenating the saturated or partially saturated compound to yield a composition of matter comprising alkanes, wherein the composition of matter is dimensioned and configured for use as a liquid transportation fuel.

38. The method of claim 37, wherein in step (d) the composition of matter is dimensioned and configured for use as a jet fuel.

39. The method of claim 37, wherein step (b) further comprises running the self-aldol condensation reaction or the crossed-aldol condensation reaction in the presence of a mineral base catalyst or a solid base catalyst comprising magnesium, zirconium, and oxygen.

40. The method of claim 37, wherein step (b) comprises running the self-aldol condensation reaction or the crossed-aldol condensation reaction in a biphasic reaction medium comprising an aqueous reaction solution comprising a salt, a substantially immiscible organic extraction solution, and NaOH as a mineral base catalyst.

41. The method of claim 37, wherein in step (a), step (b) or in both steps (a) and (b) the aqueous reaction medium further comprises at least one salt, thereby yielding a saline aqueous reaction solution.

42. The method of claim 41, wherein the at least one salt comprises a cation and an anion selected from the group consisting of acetate, alkylphosphate, alkylsulfate, carbonate, chromate, citrate, cyanide, formate, glycolate, halide, hexafluorophosphate, nitrate, nitrite, oxide, phosphate, sulfate, tetrafluoroborate, tosylate, triflate, and bis-trifluorsulfonimide.

43. The method of claim 37, wherein the acid catalyst is a mineral acid.

44. The method of claim 37, wherein the acid catalyst is a zeolite.

45. The method of claim 37, wherein the acid catalyst is selected from the group consisting of silica-, silica-alumina, and titania-based supports functionalized by acid groups.

46. The method of claim 37, wherein the acid catalyst is a cation exchange resin.

47. The method of claim 37, wherein the acid catalyst is a Lewis acid.

48. The method of claim 37, wherein the acid catalyst is selected from the group consisting of heteropolyacids, HCl, $HNO_3$, $H_2SO_4$, $H_3PO_4$, $H_3BO_3$, oxalic acid, levulinic acid, citric acid, $NbOPO_4$, and vanadium phosphate.

49. The method of claim 37, wherein the aqueous reaction solution contains the modifier, and the modifier comprises a dipolar, aprotic additive.

50. The method of claim 37, wherein the aqueous reaction solution contains the modifier and the modifier is selected from the group consisting of water-miscible alcohols, water-miscible ketones, and water-soluble polymers.

51. The method of claim 37, wherein the organic extraction solution contains the modifier and the modifier is selected from the group consisting of a primary, secondary, linear, branched, or cyclic $C_1$- to $C_{12}$-alcohols.

52. The method of claim 37, wherein the organic extraction solution comprises a solvent selected from the group consisting of water-immiscible, linear, branched, or cyclic alcohols, ethers, and ketones.

53. The method of claim 37, wherein the organic extraction solution comprises a solvent selected from the group consisting of unsubstituted aliphatic and aromatic hydrocarbons and halo-substituted aliphatic and aromatic hydrocarbons.

* * * * *

UNITED STATES PATENT AND TRADEMARK OFFICE
CERTIFICATE OF CORRECTION

| | | |
|---|---|---|
| PATENT NO. | : 7,880,049 B2 | |
| APPLICATION NO. | : 11/758963 | |
| DATED | : February 1, 2011 | |
| INVENTOR(S) | : James A. Dumesic et al. | |

It is certified that error appears in the above-identified patent and that said Letters Patent is hereby corrected as shown below:

Col. 1, Line 13, just prior to FIELD OF THE INVENTION please insert the following paragraph:

--STATEMENT REGARDING FEDERAL FUNDING
This invention was made with government support under 0520527 awarded by the National Science Foundation and 2003-35504-13752 awarded by the USDA/CSREES. The government has certain rights in the invention.--

Signed and Sealed this
Nineteenth Day of April, 2011

David J. Kappos
*Director of the United States Patent and Trademark Office*